United States Patent
Hill et al.

(10) Patent No.: US 6,219,144 B1
(45) Date of Patent: *Apr. 17, 2001

(54) APPARATUS AND METHOD FOR MEASURING THE REFRACTIVE INDEX AND OPTICAL PATH LENGTH EFFECTS OF AIR USING MULTIPLE-PASS INTERFEROMETRY

(75) Inventors: Henry Allen Hill, Tucson, AZ (US); Peter de Groot; Frank C. Demarest, both of Middletown, CT (US)

(73) Assignee: Zygo Corporation, Middlefield, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/252,440

(22) Filed: Feb. 18, 1999

Related U.S. Application Data

(63) Continuation-in-part of application No. 09/078,163, filed on May 13, 1998, and a continuation-in-part of application No. 08/942,848, filed on Oct. 2, 1997.
(60) Provisional application No. 60/075,566, filed on Feb. 23, 1998.

(51) Int. Cl.$^7$ ...................................................... G01B 9/02
(52) U.S. Cl. ............................................. 356/487; 356/317
(58) Field of Search .................................... 356/349, 351, 356/358, 361, 363, 486, 487, 490, 500, 509, 517

(56) References Cited

U.S. PATENT DOCUMENTS

| | | |
|---|---|---|
| 3,647,302 | 3/1972 | Zipin et al. . |
| 4,005,936 | 2/1977 | Redman et al. . |

(List continued on next page.)

FOREIGN PATENT DOCUMENTS 0 094 836    11/1983  (EP) .

WO 91/03729    3/1991  (WO) .

OTHER PUBLICATIONS

Erikson, Kent E., *Long–Path Interferometry through an Uncontrolled Atmosphere*, Journal of the Optical Society of America, vol. 52, No. 7 (Jul. 1962), pp. 781–787.

(List continued on next page.)

Primary Examiner—Samuel A. Turner
(74) Attorney, Agent, or Firm—Francis J. Caufield

(57) ABSTRACT

Apparatus and methods particularly suitable for use in electro-optical metrology and other applications to measure and monitor the refractive index of a gas in at least one measurement path and/or the change in optical path length of the measurement path due to the gas while the refractive index of the gas may be fluctuating due to turbulence or the like and/or the physical length of the measuring path may be changing. More specifically, the invention employs multiple pass interferometry to provide measurements of dispersion of the refractive index, the dispersion being substantially proportional to the density of the gas, and/or measurements of dispersion of the optical path length, the dispersion of the optical path length being related to the dispersion of the refractive index and the physical length of the measurement path. The refractive index of the gas and/or the optical path length effects of the gas are subsequently computed from the measured dispersion of the refractive index and/or the measured dispersion of the optical path length, respectively. The information generated by the inventive apparatus is particularly suitable for use in interferometric distance measuring instruments (DMI) to compensate for errors related to refractive index of gas in a measurement path brought about by environmental effects and turbulence induced by rapid stage slew rates. In preferred embodiments, differential plane mirror interferometer architectures are utilized, the operating wavelengths are approximately harmonically related and may be monitored and/or controlled to meet precision requirements, heterodyne and superheterodyne processing are beneficially used, and phase redundancy is resolved.

100 Claims, 29 Drawing Sheets

U.S. PATENT DOCUMENTS

| | | |
|---|---|---|
| 4,215,938 | 8/1980 | Farrand et al. . |
| 4,685,803 | 8/1987 | Sommargren . |
| 4,688,940 | 8/1987 | Sommargren et al. . |
| 4,733,967 | 3/1988 | Sommargren . |
| 4,802,764 * | 2/1989 | Young et al. ......................... 356/349 |
| 4,813,783 | 3/1989 | Torge . |
| 4,948,254 | 8/1990 | Ishida . |
| 5,218,426 | 6/1993 | Hall et al. . |
| 5,404,222 | 4/1995 | Lis ...................................... 356/349 |
| 5,483,343 | 1/1996 | Iwamato et al. . |
| 5,537,209 | 7/1996 | Lis . |
| 5,663,793 | 9/1997 | de Groot . |
| 5,764,362 * | 6/1998 | Hill et al. .............................. 356/361 |
| 5,838,485 * | 11/1998 | De Groot et al. .................... 356/361 |

OTHER PUBLICATIONS

Bender, Peter L. and Owens, James C., *Correction Of Optical Distance Measurements for the Fluctuating Atmospheric Index of Refraction*, Journal of Geophysical Research, vol. 70, No. 10 (May 15, 1965), pp. 2461–2462.

Edlen, Bengt, *The Refractive Index of Air, Metrologia*, vol. 2, No. 2 (1966). pp. 71–80.

Earnshaw, K. B. and Hernandez, E. Norman, *Two–Laser Optical Distance–Measuring Instrument That Corrects For The Atmospheric Index Of Refraction*, Applied Optics, vol. 11, No. 4 (Apr. 1972), pp. 749–754.

Hernandez, E. N. and Earhshaw, K. B., *Field Tests of a Two–Laser (4416A and 6328A) Optical Distance–Measuring Instrument Correcting for the Atmospheric Index of Refraction*, Journal of Geophysical Research, vol. 77, No. 35, (Dec. 10, 1972), pp. 6994–6998.

Slater, L. E. and Huggett, G. R., *A Multiwavelength Distance–Measuring Instrument for Geophysical Experiments*, Journal of Geophysical Research, vol. 81, No. 35 (Dec. 10, 1976), pp. 6299–6306.

Berg, Eduard and Carter, Jerry A., *Distance Corrections for Single–and Dual–Color Lasers by Ray Tracing*, Journal of Geophysical Research, vol. 85, No. B11, (Nov. 10, 1980), pp. 6513–6520.

Jones, Frank E., *The Refractivity of Air*, Journal of Research of the National Bureau of STandards, vol. 86, No. 1, (Jan.–Feb. 1981), pp 27–32.

Matsumoto, Hirokazu and Tsukahara, Koichi, *Effects of the atmospheric phase fluctuation on long–distance measurement*, Applied Optics, vol. 23, No. 19, (Oct. 1, 1984), pp 3388–3394.

Gibson, G. N.; Heyman, J. , Lugten, J. , Fitelson, W., and Townes, C. H., *Optical path length fluctuations in the atmosphere*, App. Optics, vol. 23, No. 23, (Dec. 1, 1984), pp 4383–4389.

Estler, W. Tyler, *High–accuracy displacement interferometry in air*, Applied Optics, vol. 24, (Mar. 15, 1985), pp. 808–815.

Bobroff, Norman, *Residual errors in laser interferometry form air turbulence and nonlinearity*, Applied Optics, vol. 26, No. 13, (Jul. 1, 1987), pp. 2676–2682.

Ishida, Akira, *Two–Wavelength Displacement–Measuring Interferometer Using Second–Harmonic Light to Eliminate Air–Turbulence–Induced Errors*, Japanese Journal of Applied Physics, vol. 28(3), (Mar. 1989), pp. L473–L475.

Birch, K. P. and Downs, M. J., *Error sources in the determination of the refractive index of air*, Applied Optics, vol. 28, No. 5, (Mar. 1, 1989), pp. 825–826.

Howe, Uwe and Kerl, Klaus, *Interferometric measurements of the dipole polarizability [alpha] of molecules between 300K and 1100K*, Molercular Physics, vol. 69 (1990), pp. 803–817.

Zhu, Yucong; Matsumoto, Hirokazu; and O'ishi, Tadanao, *Long–arm two–color interferometer for measuring the change of air refractive index*, SPIE, vol. 1319, Optics in Complex Systems (1990), pp 538–539.

Achtermann, H. J. and Magnus, G., *Refractivity virial coefficients of gaseous CH4, C2H4, C2H6, CO2, SF6, H2, N2, He, and Ar*, J. Chem. Phys., 94(8), (Apr. 15, 1991), pp. 5669–5684.

Beers, J. and Doiron, T., *Verification of Revised Water Vapour Correction to the Index of Refraction of Air*, Metrologia, 29 (1992), pp. 315–316.

Bobroff, Norman, *Recent advances in displacement measuring interferometry*, Measurement Science and Technology, vol. 4. No. 9 (Sep. 1993), pp. 907–926.

Lis, Steven A., *An Air Turbulence Compensated Interferometer For IC Manufacturing*, SPIE, Conf. 2440 (Feb. 24, 1995).

Dandliker, Rene, et al. *Two–Wavelength Laser Interferometry Using Superheterodyne Detection*, Optics Letters, vol. 13, No. 5, May 1988, pp 339–341.

Dandliker, Rene, et al. *High–Accuracy Diatance Measurements With Multiple–Wavelength Interferometry*, Optical Engineering, vol. 34, No. 8, Aug. 1995, pp 2407–2412.

Sodnik, Zoran, et al., *Two–Wavelength Double Heterdyne Interferometry Using A Matched Grating Technique*, Applied Optics, vol. 30, No. 22, Aug. 1, 1991, pp 3139–3144.

Manhart, S., et al., *Diode Laser and Fiber Optics for Dual–Wavelength Heterdyne Interferometry*, SPIE , Optics in Complex Systems, vol. 1319, 1990, pp 214–216.

* cited by examiner

APPARATUS AND METHOD FOR MEASURING THE REFRACTIVE INDEX AND OPTICAL PATH LENGTH EFFECTS OF AIR USING MULTIPLE-PASS INTERFEROMETRY

CROSS REFERENCE TO RELATED APPLICATIONS

This application relates to U.S. Pat. No. 5,764,362, claims priority from United States provisional patent application No. 60/075,566 filed on Feb. 23, 1998 and entitled "APPARATUS AND METHOD FOR MEASURING THE REFRACTIVE INDEX AND OPTICAL PATH EFFECTS OF AIR USING INTERFEROMETRY", and is also a continuation-in-part of U.S. patent application Ser. No. 09/078,163 filed on May 13, 1998 and entitled "APPARATUS AND METHODS USING MULTIPLE-PASS INTERFEROMETRY FOR MEASURING AND COMPENSATING FOR REFRACTIVE INDEX EFFECTS IN AN OPTICAL PATH", and a continuation-in-part of Ser. No. 08/942,848, filed Oct. 2, 1997, both of said applications being commonly owned herewith and incorporated herein by reference.

FIELD OF THE INVENTION

The present invention relates to optical instruments for measuring distance and refractive index. The invention relates in particular to interferometric distance measurement independent of the optical path length effects of the refractive index of a gas in a measurement path including the effects of refractive index fluctuations.

BACKGROUND AND PRIOR ART

A frequently-encountered problem in metrology is the measurement of the refractive index of a column of air. Several techniques exist for measuring the index under highly controlled circumstances, such as when the air column is contained in a sample cell and is monitored for temperature, pressure, and physical dimension. See for example, an article entitled "An air refractometer for interference length metrology," by J. Terrien, *Metrologia* 1(3), 80–83 (1965).

Perhaps the most difficult measurement related to the refractive index of air is the measurement of refractive index fluctuations over a measurement path of unknown or variable length, with uncontrolled temperature and pressure. Such circumstances arise frequently in geophysical and meteorological surveying, for which the atmosphere is obviously uncontrolled and the refractive index is changing dramatically because of variations in air density and composition. The problem is described in an article entitled "Effects of the atmospheric phase fluctuation on long-distance measurement," by H. Matsumoto and K. Tsukahara, *Appl. Opt.* 23(19), 3388–3394 (1984), and in an article entitled "Optical path length fluctuation in the atmosphere," by G. N. Gibson et al., *Appl. Opt.* 23(23), 4383–4389 (1984).

Another example situation is high-precision distance measuring interferometry, such as is employed in microlithographic fabrication of integrated circuits. See for example an article entitled "Residual errors in laser interferometry from air turbulence and non-linearity," by N. Bobroff, *Appl. Opt.* 26(13), 2676–2682 (1987), and an article entitled "Recent advances in displacement measuring interferometry," also by N. Bobroff, *Measurement Science & Tech.* 4(9), 907–926 (1993). As noted in the aforementioned cited references, interferometric displacement measurements in air are subject to environmental uncertainties, particularly to changes in air pressure and temperature; to uncertainties in air composition such as resulting from changes in humidity; and to the effects of turbulence in the air. Such factors alter the wavelength of the light used to measure the displacement. Under normal conditions the refractive index of air is approximately 1.0003 with a variation of the order of $1\times10^{-5}$ to $1\times10^{-4}$. In many applications the refractive index of air must be known with a relative precision of less than 0.1 ppm (parts per million) to 0.003 ppm, these two relative precisions corresponding to a displacement measurement accuracy of 100 nm and 3 nm, respectively, for a one meter interferometric displacement measurement.

There are frequent references in the art to heterodyne methods of phase estimation, in which the phase varies with time in a controlled way. For example, in a known form of prior-art heterodyne distance-measuring interferometer, the source emits two orthogonally polarized beams having slightly different optical frequencies (e.g. 2 MHz). The interferometric receiver in this case is typically comprised of a linear polarizer and a photodetector to measure a time-varying interference signal. The signal oscillates at the beat frequency and the phase of the signal corresponds to the relative phase difference. A further representative example of the prior art in heterodyne distance-measuring interferometry is taught in commonly-owned U.S. Pat. No. 4,688,940 issued to G. E. Sommargren and M. Schaham (1987). However, these known forms of interferometric metrology are limited by fluctuations in refractive index, and by themselves are unsuited to the next generation of microlithography instruments.

Another known form of interferometer for distance measurement is disclosed in U.S. Pat. No. 4,005,936 entitled "Interferometric Methods And Apparatus For Measuring Distance To A Surface" issued to J. D. Redman and M. R. Wall (1977). The method taught by Redman and Wall consists of employing laser beams of two different wavelengths, each of which is split into two parts. Frequency shifts are introduced into one part of the respective beams. One part of each beam reflects from an object and recombines with the other part on a photodetector. From the interference signal at the detector, a phase at a difference frequency is derived which is a measure of the distance to the surface. The equivalent wavelength of the phase associated with the difference frequency is equal to the product of the two laser wavelengths divided by the difference of the two wavelengths. This two-wavelength technique of Redman and Wall reduces measurement ambiguities, but is at least as sensitive to the deleterious effects of refractive index fluctuations of the air as single-wavelength techniques.

Another example of a two-wavelength interferometer similar to that of Redman and Wall is disclosed in U.S. Pat. No. 4,907,886 entitled "Method And Apparatus For Two-Wavelength Interferometry With Optical Heterodyne Processes And Use For Position Or Range Finding," issued to R. Dändliker and W. Heerburgg (1990). This system is also described in an article entitled "Two-Wavelength Laser Interferometry Using Superheterodyne Detection," by R. Dändliker, R. Thalmann, and D. Prongué, *Opt. Let.* 13(5), 339–341 (1988), and in an article entitled "High-Accuracy Distance Measurements With Multiple-Wavelength Interferometry," by R. Dändliker, K. Hug, J. Politch, and E. Zimmermann. The system of Dändliker et al., as taught in U.S. Pat. No. 4,907,886, employs laser beams of two wavelengths, each of the beams comprising two polarization components separated in frequency by means of acousto-optic modulation. After passing these beams collinearly through a Michelson interferometer, the polarization components are mixed, resulting in an interference signal, i.e. a heterodyne signal. In that the heterodyne signal has a different frequency for each of the two wavelengths, a so-called superheterodyne signal results therefrom having a frequency equal to the difference in the heterodyne frequencies and a phase associated with an equivalent wavelength equal to the product of the two laser wavelengths divided by the difference of the two wavelengths. According to U.S. Pat. No. 4,907,886 (cited above), the phase of the superheterodyne signal is assumed to be dependent only on the position of a measurement object and the equivalent wavelength. Therefore, this system is also not designed to measure or compensate for the fluctuations in the refractive index of air.

Further examples of the two-wavelength superheterodyne technique developed by Redman and Wall and by Dändliker and Heerburgg (cited above) are found in an article entitled "Two-wavelength double heterodyne interferometry using a matched grating technique," by Z. Sodnik, E. Fischer, T. Ittner, and H. J. Tiziani, *Appl. Opt.* 30(22), 3139–3144 (1991), and in an article entitled "Diode laser and fiber optics for dual-wavelength heterodyne interferometry," by S. Manhart and R. Maurer, *SPIE* 1319, 214–216 (1990). However, neither one of these examples addresses the problem of refractive index fluctuations.

It may be concluded from the foregoing that the prior art in heterodyne and superheterodyne interferometry does not provide a high speed method and corresponding means for measuring and compensating the optical path length effects of air in a measuring path, particularly effects due to fluctuations in the refractive index of air. This deficiency in the prior art results in significant measurement uncertainty, thus seriously affecting the precision of systems employing such interferometers as found for example in micro-lithographic fabrication of integrated circuits. Future interferometers will necessarily incorporate an inventive, new method and means for measuring and compensating a fluctuating refractive index in a measurement path comprised of a changing physical length.

One way to detect refractive index fluctuations is to measure changes in pressure and temperature along a measurement path and calculate the effect on the optical path length of the measurement path. Mathematical equations for effecting this calculation are disclosed in an article entitled "The Refractivity Of Air," by F. E. Jones, *J. Res. NBS* 86(1), 27–32 (1981). An implementation of the technique is described in an article entitled "High-Accuracy Displacement Interferometry In Air," by W. T. Estler, *Appl. Opt.* 24(6), 808–815 (1985). Unfortunately, this technique provides only approximate values, is cumbersome, and corrects only for slow, global fluctuations in air density.

Another, more direct way to detect the effects of a fluctuating refractive index over a measurement path is by multiple-wavelength distance measurement. The basic principle may be understood as follows. Interferometers and laser radar measure the optical path length between a reference and an object, most often in open air. The optical path length is the integrated product of the refractive index and the physical path traversed by a measurement beam. In that the refractive index varies with wavelength, but the physical path is independent of wavelength, it is generally possible to determine the physical path length from the optical path length, particularly the contributions of fluctuations in refractive index, provided that the instrument employs at least two wavelengths. The variation of refractive index with wavelength is known in the art as dispersion, therefore this technique will be referred to hereinafter as the dispersion technique.

The dispersion technique for refractive index measurement has a long history, and predates the introduction of the laser. An article entitled "Long-Path Interferometry Through An Uncontrolled Atmosphere," by K. E. Erickson, *JOSA* 52(7), 781–787 (1962), describes the basic principles and provides an analysis of the feasibility of the technique for geophysical measurements. Additional theoretical proposals are found in an article entitled "Correction Of Optical Distance Measurements For The Fluctuating Atmospheric Index Of Refraction," by P. L. Bender and J. C. Owens, *J. Geo. Res.* 70(10), 2461–2462 (1965).

Commercial distance-measuring laser radar based on the dispersion technique for refractive index compensation appeared in the 1970's. An article entitled "Two-Laser Optical Distance-Measuring Instrument That Corrects For The Atmospheric Index Of Refraction," by K. B. Earnshaw and E. N. Hernandez, *Appl. Opt.* 11(4), 749–754 (1972), discloses an instrument employing microwave-modulated HeNe and HeCd lasers for operation over a 5 to 10 km measurement path. Further details of this instrument are found in an article entitled "Field Tests Of A Two-Laser (4416A and 6328A) Optical Distance-Measuring Instrument Correcting For The Atmospheric Index Of Refraction," by E. N. Hernandez and K. B. Earnshaw, *J. Geo. Res.* 77(35), 6994–6998 (1972). Further examples of applications of the dispersion technique are discussed in an article entitled "Distance Corrections For Single- And Dual-Color Lasers By Ray Tracing," by E. Berg and J. A. Carter, *J. Geo. Res.* 85(B11), 6513–6520 (1980), and in an article entitled "A Multi-Wavelength Distance-Measuring Instrument For Geophysical Experiments," by L. E. Slater and G. R. Huggett, *J. Geo. Res.* 81(35), 6299–6306 (1976).

Although instrumentation for geophysical measurements typically employs intensity-modulation laser radar, it is understood in the art that optical interference phase detection is more advantageous for shorter distances. In U.S. Pat. No. 3,647,302 issued in 1972 to R. B. Zipin and J. T. Zalusky, entitled "Apparatus For And Method Of Obtaining Precision Dimensional Measurements," there is disclosed an interferometric displacement-measuring system employing multiple wavelengths to compensate for variations in ambient conditions such as temperature, pressure, and humidity. The instrument is specifically designed for operation with a movable object, that is, with a variable physical path length. However, the phase-detection means of Zipin and Zalusky is insufficiently accurate for high-precision measurement.

A more modern and detailed example is the system described in an article by Y. Zhu, H. Matsumoto, T. O'ishi, *SPIE* 1319, Optics in Complex Systems, 538–539 (1990), entitled "Long-Arm Two-Color Interferometer For Measuring The Change Of Air Refractive Index." The system of Zhu et al. employs a 1064 nm wavelength YAG laser and an 632 nm HeNe laser together with quadrature phase detection. Substantially the same instrument is described in Japanese in an earlier article by Zhu et al. entitled "Measurement Of Atmospheric Phase And Intensity Turbulence For Long-Path Distance Interferometer," *Proc. 3rd Meeting On Lightwave Sensing Technology, Appl. Phys. Soc. of Japan*, 39 (1989). However, the interferometer of Zhu et al. has insufficient resolution for all applications, e.g. sub-micron interferometry for micro-lithography.

A recent attempt at high-precision interferometry for micro-lithography is represented by U.S. Pat. No. 4,948,254 issued to A. Ishida (1990). A similar device is described by Ishida in an article entitled "Two Wavelength Displacement-Measuring Interferometer Using Second-Harmonic Light To Eliminate Air-Turbulence-Induced Errors," *Jpn. J. Appl. Phys.* 28(3), L473–475 (1989). In the article, a displacement-measuring interferometer is disclosed which eliminates errors caused by fluctuations in the refractive index by means of two-wavelength dispersion detection. An Ar+ laser source provides both wavelengths simultaneously by means of a frequency-doubling crystal known in the art as BBO. The use of a BBO doubling crystal results in two wavelengths that are fundamentally phase locked, thus greatly improving the stability and accuracy of the refractive index measurement. However, the phase detection means, which employ simple homodyne quadrature detection, are insufficient for high resolution phase measurement. Further, the phase detection and signal processing means are not suitable for dynamic measurements, in which the motion of the object results in rapid variations in phase that are difficult to detect accurately.

In U.S. Pat. No. 5,404,222 entitled "Interferometric Measuring System With Air Turbulence Compensation," issued to S. A. Lis (1995), there is disclosed a two-wavelength interferometer employing the dispersion technique for detecting and compensating refractive index fluctuations. A similar device is described by Lis in an article entitled "An Air Turbulence Compensated Interferometer For IC Manufacturing," *SPIE* 2440 (1995). Improvement on U.S. Pat. No. 5,404,222 by S. A. Lis is disclosed in U.S. Pat. No. 5,537,209, issued July 1996. The principal innovation of this system with respect to that taught by Ishida in *Jpn. J. Appl. Phys.* (cited above) is the addition of a second BBO doubling crystal to improve the precision of the phase detection means. The additional BBO crystal makes it possible to optically interfere two beams having wavelengths that are exactly a factor of two different. The resultant interference has a phase that is directly dependent on the refractive index but is substantially independent of stage motion. However, the system taught by Lis has the disadvantage that it is complicated and requires an additional BBO crystal for every measurement path. In that micro-lithography stages frequently involve six or more measurement paths, and that BBO can be relatively expensive, the additional crystals are a significant cost burden. An additional disadvantage of Lis' system is that it employs a low-speed (32-Hz) phase detection system based on the physical displacement of a PZT transducer.

It is clear from the foregoing, that the prior art does not provide a practical, high-speed, high-precision method and corresponding means for measuring refractive index of air and measuring and compensating for the optical path length effects of the air in a measuring path, particularly the effects due to fluctuations in the refractive index of the air. The limitations in the prior art arise principally from the following, unresolved technical difficulties: (1) Prior-art heterodyne and superheterodyne interferometers are limited in accuracy by fluctuations in the refractive index of air; (2) Prior-art dispersion techniques for measuring index fluctuations require extremely high accuracy in interference phase measurement, typically exceeding by an order of magnitude the typical accuracy of high-precision distance-measuring interferometers; (3) Obvious modifications to prior-art interferometers to improve phase-measuring accuracy would increase the measurement time to an extent incompatible with the rapidity of stage motion in modern micro-lithography equipment; (4) Prior-art dispersion techniques require at least two extremely stable laser sources, or a single source emitting multiple, phase-locked wavelengths; (5) Prior-art dispersion techniques in micro-lithography applications are sensitive to stage motion during the measurement, resulting in systematic errors; and (6) Prior-art dispersion techniques that employ doubling crystals (e.g. U.S. Pat. No. 5,404,222 to Lis) as part of the detection system are expensive and complicated.

These deficiencies in the prior art have led to the absence of any practical interferometric system for performing displacement measurement for micro-lithography in the presence of a gas in a measurement path where there are typically refractive index fluctuations and the measurement path is comprised of a changing physical length.

Accordingly, it is an object of the invention to provide a method and apparatus for rapidly and accurately measuring and monitoring the refractive index of a gas in a measurement path and/or the optical path length effects of the gas wherein the refractive index may be fluctuating and/or the physical length of the measurement path may be changing.

It is another object of the invention to provide a method and apparatus for rapidly and accurately measuring and monitoring the refractive index of a gas in a measurement path and/or the optical path length effects of the gas wherein the accuracy of measurements and monitoring of the refractive index of the gas and/or of the optical path length effects of the gas are substantially not compromised by a rapid change in physical length of measurement path.

It is another object of the invention to provide a method and apparatus for rapidly and accurately measuring and monitoring the refractive index of a gas in a measurement path and/or the optical path length effects of the gas wherein the method and apparatus does not require measurement and monitoring of environmental conditions such as temperature and pressure.

It is another object of the invention to provide a method and apparatus for rapidly and accurately measuring and monitoring the refractive index of a gas in a measurement path and/or the optical path length effects of the gas wherein the method and apparatus may use but does not require the use of two or more optical beams of differing wavelengths which are phase locked.

It is another object of the invention to provide a method and apparatus for rapidly and accurately measuring and monitoring the optical path length effects of a gas in a measurement path wherein the lengths of measuring paths in an interferometric measurement are substantially not used in a computation of the optical path length effects of the gas.

It is another object of the invention to provide a method and apparatus for rapidly and accurately measuring and monitoring the refractive index of a gas in a measurement path and/or the optical path length effects of the gas wherein the frequencies of the optical beams used in an interferometric measurement and monitoring of the refractive index of a gas in a measurement path and/or the optical path length effects of the gas are substantially not used in a computation of the relative contribution of the optical path length effects of the gas.

Other objects of the invention will, in part, be obvious and will, in part, appear hereinafter. The invention accordingly comprises methods and apparatus possessing the construction, steps, combination of elements, and arrangement of parts exemplified in the detailed description to follow when read in connection with the drawings.

SUMMARY OF THE INVENTION

The present invention generally relates to apparatus and methods for measuring and monitoring the refractive index of a gas in a measurement path and/or the change in optical path length of the measurement path due to the gas wherein the refractive index of the gas may be fluctuating, e.g. the gas is turbulent, and/or the physical length of the measuring path may be changing. The present invention also relates to apparatus and methods for use in electro-optical metrology and other applications. More specifically, the invention operates to provide measurements of dispersion of the refractive index, the dispersion being substantially proportional to the density of the gas, and/or measurements of dispersion of the optical path length, the dispersion of the optical path length being related to the dispersion of the refractive index and the physical length of the measurement path. The refractive index of the gas and/or the optical path length effects of the gas are subsequently computed from the measured dispersion of the refractive index and/or the measured dispersion of the optical path length, respectively. The information generated by the inventive apparatus is particularly suitable for use in interferometric distance measuring instruments (DMI) to compensate for errors related to refractive index of gas in at least one measurement path brought about by environmental effects and turbulence induced by rapid stage slew rates.

Several embodiments of the invention have been made and these fall broadly into two categories that address the need for more or less precision in final measurements. While the various embodiments share common features, they differ in some details to achieve individual goals.

In general, the inventive apparatus comprises interferometer means having first and second measurement legs at least one of which has a variable length and at least one of which is at least in part occupied by the gas. In preferred embodiments one of the measurement legs is a reference leg and the other a measurement leg. The constituent legs are preferably configured and arranged so that the measurement leg has a portion of its optical path length substantially the same as the optical path length of the reference leg. The gas in the remaining portion of the optical path of the measurement leg in a typical interferometric DMI application is air.

Means for generating at least two light beams having different wavelengths are included. In preferred embodiments, a source generates a set of light beams, the set of light beams being comprised of at least two light beams, each beam of the set of light beams having a different wavelength. The relationship between the wavelengths of the beams of the set of light beams, the approximate relationship, is known.

A set of frequency-shifted light beams is generated from the set of light beams by introducing at least one frequency difference between two orthogonally polarized components of each beam of the set of light beams. In certain of the embodiments, no two beams of the set of frequency-shifted light beams have the same frequency difference while in certain other of the embodiments, at least two of the beams of the set of frequency-shifted beams have the same frequency difference. For a given embodiment, the ratios of the wavelengths are the same as the known approximate relationship to relative precisions, which depend on chosen operating wavelengths and the corresponding known approximate relationship. Because of this wavelength dependence, these relative precisions are referred to as the respective relative precisions of the ratios of the wavelengths. In a number of embodiments, the respective relative precisions of the ratios of wavelengths are of an order of magnitude less than the respective dispersions of the gas times the relative precision required for the measurement of the respective refractive indices of the gas and/9or for the measurement of the respective changes in the optical path length of the measurement leg due to the gas.

In certain ones of the embodiments, the approximate relationship is expressed as a sequence of ratios, each ratio comprising a ratio of low order non-zero integers, e.g. 2/1, to respective relative precisions, the respective relative precisions of the sequence of ratios, wherein a respective relative precision of the respective relative precisions of the sequence of ratios is of an order of magnitude less than the respective dispersion of the gas times the respective relative precision required for the measurement of the respective refractive index of the gas and/or for the measurement of the respective change in the optical path length of the measurement leg due to the gas.

In other embodiments, where the respective relative precisions of the ratios of the wavelengths is inappropriate with respect to the desired value, means are provided for monitoring the ratios of the wavelengths and either providing feedback to control the respective relative precisions of the ratios of the wavelengths, information to correct subsequent calculations influenced by undesirable departures of the respective relative precisions of the ratios of the wavelengths from the desired respective relative precisions of the ratios of the wavelengths, or some combination of both. Means are also provided for monitoring the wavelength used in the primary objective of DMI, i.e., the determination of a change in a length of the measurement path.

At least a portion of each of the frequency-shifted light beams is introduced into the interferometer means by suitable optical means so that a first portion of at least a portion of each frequency-shifted light beam travels through the reference leg along predetermined paths of the reference leg and a second portion of at least a portion of each frequency-shifted light beam travels through the measurement leg along predetermined paths of the measurement leg, the first and second portions of at least a portion of each frequency-shifted light beam being different. Afterwards, the first and second portions of at least a portion of each frequency-shifted light beam emerge from the interferometer means as exit beams containing information about the optical path length through the predetermined paths in the reference leg and the optical path length through the predetermined paths in the measurement leg. In one of the embodiments, three sets of first and second portions of at least a portion of each frequency-shifted light beam are generated, one set at one wavelength and two sets at another wavelength.

In yet another embodiment, the optical means are configured to cause certain ones of the at least a portion of each of the frequency-shifted light beams to undergo multiple passes as they travel through the reference and measurement legs and to cause additional certain ones of the at least a portion of each of the frequency-shifted light beams to undergo multiple passes as they travel through the reference and measurement legs, the number of multiple passes for the certain ones being different from the number of multiple passes for the additional certain ones.

More generally, first and second predetermined portions of the light beams travel through a first and second measurement legs along predetermined optical paths a different number of passes to compensate for the relative rates at which the physical path lengths of the first and second measurement legs are changing Combining means are provided for receiving the exit beams to produce mixed optical signals which contain information corresponding to the phase differences between the exit beams of the first and second portions of at least a portion of each frequency-shifted light beam. The mixed optical signals are then sensed by a photodetector, preferably by photoelectric detection, which operates to generate electrical interference signals that contain information corresponding to the refractive index of the gas at the different beam wavelengths and to the optical path length in the measurement leg due to the refractive index of the gas at the different beam wavelengths.

The electrical interference signals are then analyzed by electronic means that operate to determine the dispersion of the optical path length of the measurement leg substantially due to the dispersion of the refractive index of the gas and/or the dispersion $(n_i-n_j)$ of the gas where i and j are integers corresponding to wavelengths and different from one another. From this information and the reciprocal dispersive power of the gas, the refractivity of the gas, $(n_r-1)$ where r is an integer corresponding to a wavelength, and/or the contribution to the optical path length of the measurement leg due to the refractive index of the gas can also be determined by the electronic means. The value of r may be different from i and j or equal to either i or j. The electronic means can comprise electronic means in the form of a microprocessor or a general purpose computer suitably programmed in well-known ways to perform the needed calculations.

In preferred form, the electrical interference signals comprise heterodyne signals containing phase information corresponding to the refractive index of the gas and to the optical path length of the measurement leg and the apparatus further comprises means to determine the phases of the heterodyne signals to generate phase information corresponding to the dispersion of the refractive index of the gas and to the dispersion of the optical path length of the measurement leg due to the dispersion of the refractive index of the gas. In certain of the embodiments, the apparatus further comprises means for mixing, i.e. multiplying, the heterodyne signals to generate at least one superheterodyne signal containing phase corresponding to the dispersion of the refractive index of the gas and to the dispersion of the optical path length of the measurement leg due to the dispersion of the refractive index of the gas. Means are also included for resolving phase ambiguities of the heterodyne signals and the superheterodyne signals generated in certain of the embodiments. Depending on the details of the optical paths experienced by the light beam portions as they travel through the interferometer means of the various embodiments, additional or different electronics are provided. In the foregoing manner, the electronic means operates to ameliorate any effects on calculations due to the rate at which the physical path length of the measurement leg occupied by the gas is changing.

While the inventive method disclosed may be carried out using the preferred apparatus described, it will be evident that it may also be practiced using other well-known apparatus. In addition, it is shown that apparatus may be employed which uses homodyne signals.

BRIEF DESCRIPTION OF THE DRAWINGS

The structure and operation of the invention, together with other objects and advantages thereof, may best be understood by reading the detailed description in conjunction with the drawings wherein the invention's parts have an assigned reference numeral that is used to identify them in all of the drawings in which they appear and wherein:

FIG. 1b illustrates differential plane mirror interferometer 69;

FIG. 1c illustrates differential plane mirror interferometer group 70;

FIG. 1d illustrates external mirror system 90, furnishing the external mirrors for differential plane mirror interferometer 69, and stage translator 67;

FIG. 1e illustrates external mirror system 90, furnishing the external mirrors for differential plane mirror interferometer group 70, and stage translator 67;

FIG. 1f is a drawing showing a block diagram of the processing electronics 109;

FIG. 2b illustrates differential plane mirror interferometer 170;

FIG. 2c is a drawing showing a block diagram of the processing electronics 209;

FIG. 3b illustrates differential plane mirror interferometer 369 for the case of light beam 9 entering differential plane mirror interferometer 369;

FIG. 3c illustrates differential plane mirror interferometer 369 for the case of light beam 445 exiting differential plane mirror interferometer 369;

FIG. 3d illustrates differential plane mirror interferometer 270;

FIG. 3e illustrates external mirror system 90, furnishing the external mirrors for differential plane mirror interferometer 369, and stage translator 67;

FIG. 3f illustrates external mirror system 90, furnishing the external mirrors for differential plane mirror interferometer group 270, and stage translator 67;

FIG. 3g is a drawing showing a block diagram of the processing electronics 309;

FIG. 4b illustrates the external mirror system 90b, furnishing the external mirrors for differential plane mirror interferometer 69b;

FIG. 4c illustrates the external mirror system 90b furnishing the external mirrors for differential plane mirror interferometer group 70b;

FIG. 4d is a drawing showing a block diagram of the processing electronics 109b;

FIGS. 6a–6c relate to lithography and its application to manufacturing integrated circuits wherein FIG. 6a is a schematic drawing of a lithography exposure system employing the interferometry system.

FIGS. 6b and 6c are flow charts describing steps in manufacturing integrated circuits.

DETAILED DESCRIPTION OF THE INVENTION

Figure 1A:
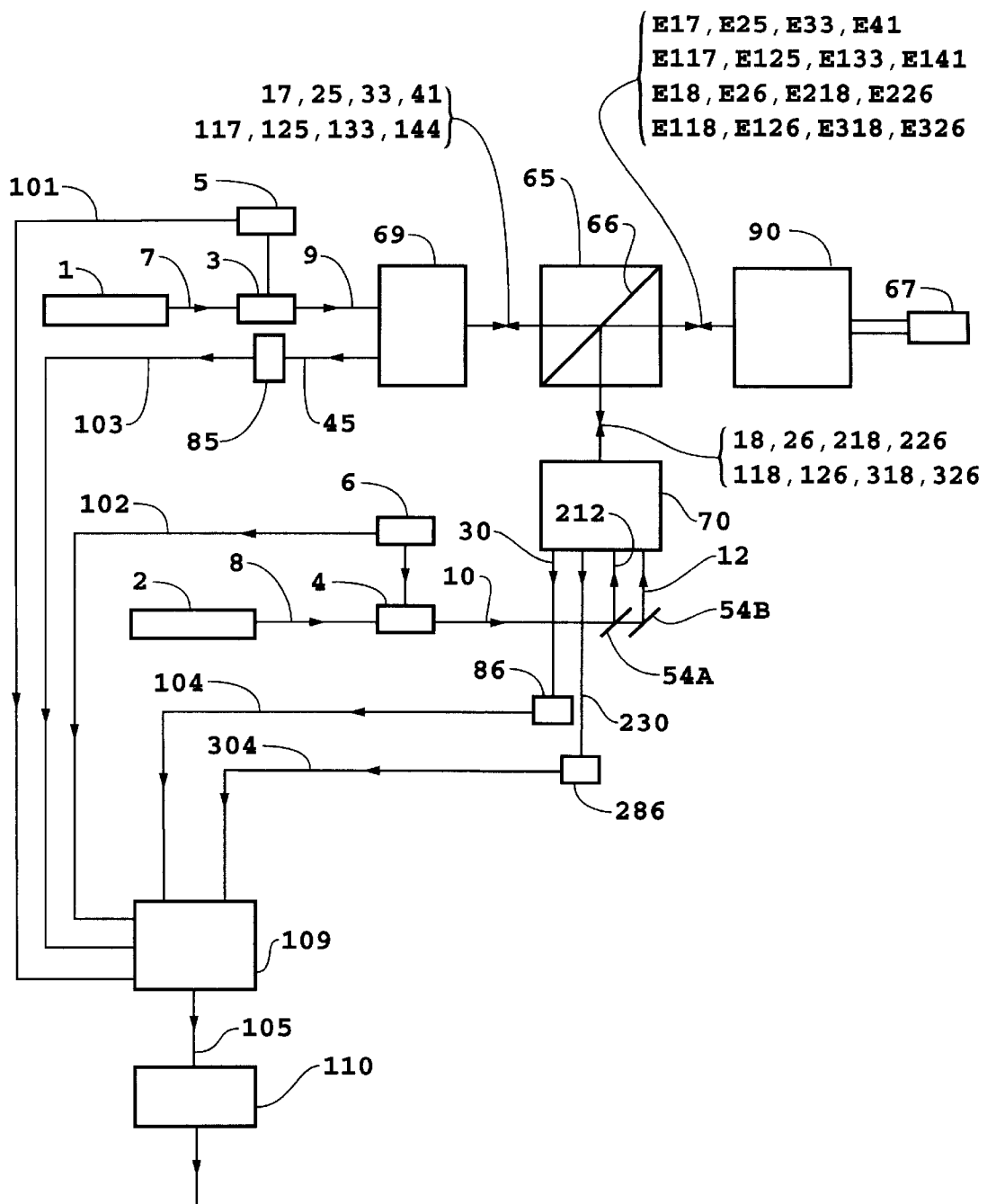
FIGS. 1a–1f taken together illustrate, in diagrammatic form, the presently preferred first embodiment of the present invention with FIG. 1a showing optical paths between source 1, modulator 3, source 2, modulator 4, differential plane mirror interferometer 69, differential plane mirror interferometer group 70, beam splitter 65, external mirror system 90, and detectors 85, 86, and 286 and the paths of electrical signals between driver 5, modulator 3, driver 6, modulator 4, detectors 85, 86, and 286, electronic processor 109, and computer 110.

The present invention relates to apparatus and methods by which the refractivity of a gas in at least one measurement path and/or the change in the optical path length of the measurement path due to the gas may be quickly measured and used in subsequent downstream or contemporaneous applications wherein either or both the refractive index of the gas and the physical length of the measurement path may be changing. An example of a contemporaneous application is in an interferometric distance measuring instrument to enhance accuracy by compensating for the effects of the refractive index of the gas in the measurement path, especially changes in the optical path length that take place during the measuring period because of changing environmental conditions or air turbulence induced in the measurement path by rapid stage slew rates.

A number of different embodiments of the apparatus of the invention are shown and described. While they differ in some details, the disclosed embodiments otherwise share many common elements and naturally fall into two categories depending on the degree of control demanded of their light sources. As will be seen, the disclosed embodiments within each category also differ in the details of how their interferometric optical paths are implemented and/or how certain information signals are handled electronically.

The first group of embodiments to be described comprise three embodiments and variants thereof. This group is intended for applications where the stability of the adopted light sources is sufficient and the ratio of the wavelengths of the light beams generated by the adopted light sources is matched to a sequence of known ratio values with respective relative precisions sufficient to meet the required precision imposed on the output data by the final end use application.

The second group of embodiments also comprise three embodiments and variants thereof, and these are particularly suitable for use where it is necessary to monitor the stability of the light sources and measure the ratios of the wavelengths of the light beams generated by the adopted light sources to meet performance requirements on accuracy. For both groups, apparatus is disclosed for dealing with phase ambiguities and phase and group delays that may arise in analyzing homodyne, heterodyne, and/or superheterodyne signals, and methods are disclosed for implementing the steps of the invention.

An unusual and inventive characteristic of the different variants of the embodiments of the apparatus of the present invention is displayed in an example wherein the beam of one wavelength $\lambda_1$ effectively experiences a phase shift proportional to 2p times the round-trip physical length of a measurement path times the index of refraction $n_1$ at $\lambda_1$, p being an integer, whereas a second beam of wavelength $\lambda_2$ effectively experiences a phase shift proportional to p times the round-trip physical length of the measurement path times the index of refraction $n_2$ at $\lambda_2$, the first wavelength being approximately twice that of the second wavelength. As a consequence of the first beam effectively experiencing a multiple pass of 2p passes through the measurement path and the second beam effectively experiencing a multiple pass of p passes through the measurement path, the optical path lengths for the two beams are approximately the same thereby enhancing the relative effect of differences due to the refractivity of the gas. Moreover, the Doppler shifts for the two beams are approximately the same thereby reducing the effects of differences in group delays experienced by interference signals. Multiple-pass interferometers are known in the art as a means of improving measurement resolution, for example, as described in an article entitled "Double-passed two-beam interferometers" by P. Hariharan and D. Sen, *J. Opt. Soc. Am.* 50, 357–361 (1960); however, the inventive combination of a p-pass and 2p-pass interferometer in the same system for the purpose of measuring the amount of gas and compensation for gas in the measurement path is not known to the applicants and is taught herein for the first time in the art. Apparatus for achieving such an inventive combination are described in the following paragraphs. While the preferred embodiments are set forth in terms of a reference path and a measurement path, it will be apparent that both paths may be measurement paths of variable length where at least one of them is at least in part occupied by a gas.

FIGS. 1a–1f depict in schematic form one preferred embodiment of the present invention for measuring and monitoring the refractivity of a gas in a measurement path and/or the change in the optical path length of the measurement path due to the gas wherein either or both the refractive index of the gas and the physical length of the measurement path may be changing, where the stability of the adopted light sources is sufficient, and the ratio of the wavelengths of the light beams generated by the adopted light sources is matched to a known ratio value with a relative precision sufficient to meet the required precision imposed on the output data by the final end use application. While the apparatus has application for a wide range of radiation sources, the following description is taken by way of example with respect to an optical measuring system.

Referring to FIG. 1a and in accordance with the preferred apparatus and method of the first preferred embodiment of the present invention, a light beam 7 emitted from source 1 passes through a modulator 3 becoming light beam 9. Modulator 3 is excited by a driver 5. Source 1 is preferably a laser or like source of coherent radiation, preferably polarized, and having a wavelength $\lambda_1$. Modulator 3 may for example be an acousto-optical device or a combination of acousto-optical devices with additional optics for selectively modulating polarization components of beam 7. Modulator 3 preferably shifts the oscillation frequency of one linearly polarized component of beam 7 an amount $f_1$ with respect to an orthogonally linearly polarized component, the directions of polarizations of the components denoted herein as x and y. In the following description of the first embodiment, it will be assumed that the x polarization component of beam 9 has an oscillation frequency shifted an amount $f_1$ with respect to the y polarization component of beam 9 without departing from the spirit or scope of the present invention. The oscillation frequency $f_1$ is determined by the driver 5.

In a next step, a light beam 8 emitted from a source 2 passes through a modulator 4 becoming light beam 10. Modulator 4 is excited by a driver 6, similar to modulator 3 and driver 5, respectively. Source 2, similar to source 1, is preferably a laser or like source of polarized, coherent radiation, but preferably at a different wavelength, $\lambda_2$, wherein the ratio of the wavelengths $(\lambda_1/\lambda_2)$ has a known approximate ratio value $l_1/l_2$, i.e.

$$(\lambda_1/\lambda_2) \cong (l_1/l_2) \tag{1}$$

where $l_1$ and $l_2$ may assume integer and non-integer values, and the ratio of the wavelengths $(\lambda_1/\lambda_2)$ is the same as the ratio value $l_1/l_2$ to a relative precision of an order of magnitude or more less than the dispersion of the refractive index of the gas, $(n_2-n_1)$, times the relative precision $\epsilon$ desired for the measurement of the refractivity of the gas or of the change in the optical path length of the measurement leg due to the gas. The x polarized component of beam 10 has an oscillation frequency shifted an amount $f_2$ with respect to the y polarized component of beam 10. The oscillation frequency $f_2$ is determined by the driver 6. In addition, the directions of the frequency shifts of the x components of beams 9 and 10 are the same.

It will be appreciated by those skilled in the art that beams 7 and 8 may be provided alternatively by a single laser source emitting more than one wavelength, by a single laser source combined with optical frequency doubling means to achieve frequency doubling, tripling, quadrupling, etc., two laser sources of differing wavelengths combined with sum-frequency generation or difference-frequency generation, or any equivalent source configuration capable of generating light beams of two or more wavelengths.

A laser source, for example, can be a gas laser, e.g. a HeNe, stabilized in any of a variety of conventional techniques known to those skilled in the art, see for example, T. Baer et al., "Frequency Stabilization of a 0.633 µm He—Ne-longitudinal Zeeman Laser," *Applied Optics*, 19, 3173–3177 (1980); Burgwald et al., U.S. Pat. No. 3,889,207, issued Jun. 10, 1975; and Sandstrom et al., U.S. Pat. No. 3,662,279, issued May 9, 1972. Alternatively, the laser can be a diode laser frequency stabilized by one of a variety of conventional techniques known to those skilled in the art, see, for example, T. Okoshi and K. Kikuchi, "Frequency Stabilization of Semiconductor Lasers for Heterodyne-type Optical Communication Systems," *Electronic Letters*, 16, 179–181 (1980) and S. Yamaqguchi and M. Suzuki, "Simultaneous Stabilization of the Frequency and Power of an AlGaAs Semiconductor Laser by Use of the Optogalvanic Effect of Krypton," *IEEE J. Quantum Electronics*, QE-19, 1514–1519 (1983).

It will also be appreciated by those skilled in the art that the two optical frequencies of beam 9 and of beam 10 may be produced by any of a variety of frequency modulation apparatus and/or lasers: (1) use of a Zeeman split laser, see for example, Bagley et al., U.S. Pat. No. 3,458,259, issued Jul. 29, 1969; G. Bouwhuis, "Interferometrie Mit Gaslasers," Ned. T. Natuurk, 34, 225–232 (August 1968); Bagley et al., U.S. Pat. No. 3,656,853, issued Apr. 18, 1972; and H. Matsumoto, "Recent interferometric measurements using stabilized lasers," *Precision Engineering*, 6(2), 87–94 (1984); (2) use of a pair of acousto-optical Bragg cells, see for example, Y. Ohtsuka and K. Itoh, "Two-frequency Laser Interferometer for Small Displacement Measurements in a Low Frequency Range," *Applied Optics*, 18(2), 219–224 (1979); N. Massie et al., "Measuring Laser Flow Fields With a 64-Channel Heterodyne Interferometer," *Applied Optics*, 22(14), 2141–2151 (1983); Y. Ohtsuka and M. Tsubokawa, "Dynamic Two-frequency Interferometry for Small Displacement Measurements," *Optics and Laser Technology*, 16, 25–29 (1984); H. Matsumoto, ibid.; P. Dirksen, et al., U.S. Pat. No. 5,485,272, issued Jan. 16, 1996; N. A. Riza and M. M. K. Howlader, "Acousto-optic system for the generation and control of tunable low-frequency signals," *Opt. Eng.*, 35(4), 920–925 (1996); (3) use of a single acousto-optic Bragg cell, see for example, G. E. Sommargren, commonly owned U.S. Pat. No. 4,684,828, issued Aug. 4, 1987; G. E. Sommargren, commonly owned U.S. Pat. No. 4,687,958, issued Aug. 18, 1987; P. Dirksen, et al., ibid.; (4) use of two longitudinal modes of a randomly polarized HeNe laser, see for example, J. B. Ferguson and R. H. Morris, "Single Mode Collapse in 6328 Å HeNe Lasers," *Applied Optics*, 17(18), 2924–2929 (1978); or (5) use of birefringent elements or the like internal to the laser, see for example, V. Evtuhov and A. E. Siegman, "A 'Twisted-Mode' Technique for Obtaining Axially Uniform Energy Density in a Laser Cavity," *Applied Optics*, 4(1), 142–143 (1965).

The specific device used for the sources of beams 7 and 8 will determine the diameter and divergence of beams 7 and 8, respectively. For some sources, e.g., a diode laser, it will likely be necessary to use conventional beam shaping optics, e.g., a conventional microscope objective, to provide beams 7 and 8 with a suitable diameter and divergence for the elements that follow. When the source is a HeNe laser, for example, beam shaping optics may not be required.

It will be further appreciated by those skilled in the art that both the x and y polarization components of beam 9 and/or of beam 10 may be frequency shifted without departing from the scope and spirit of the invention, $f_1$ remaining the difference in frequencies of the x and y polarization components of beam 9 and $f_2$ remaining the difference in frequencies of the x and y polarization components of beam 10. Improved isolation of an interferometer and a laser source is generally possible by frequency shifting both x and y polarization components of a beam, the degree of improved isolation depending on the means used for generating the frequency shifts.

In a next step, a portion of beam 10 is reflected by a beam splitter 54A, preferably a nonpolarizing type, as beam 212, and a second portion of beam 10 is transmitted by beam splitter 54A and subsequently reflected by mirror 54B becoming beam 12. Beam 9 is incident on differential plane mirror interferometer 69 and beams 12 and 212 are incident on differential plane mirror interferometer group 70 comprising two differential plane mirror interferometers. Differential plane mirror interferometer 69 and differential plane mirror interferometer group 70 with beam splitter 65 and external mirrors furnished by external mirror system 90 comprise means for introducing a phase shift $\phi_1$ between the x and y components of beam 9, a phase shift $\phi_2$ between the x and y components of beam 12, and a phase shift $\phi_3$ between the x and y components of beam 212. External plane mirror system 90 may be connected to a photolithographic apparatus 67 of one of the types described hereinafter or other downstream application.

Figure 1B:
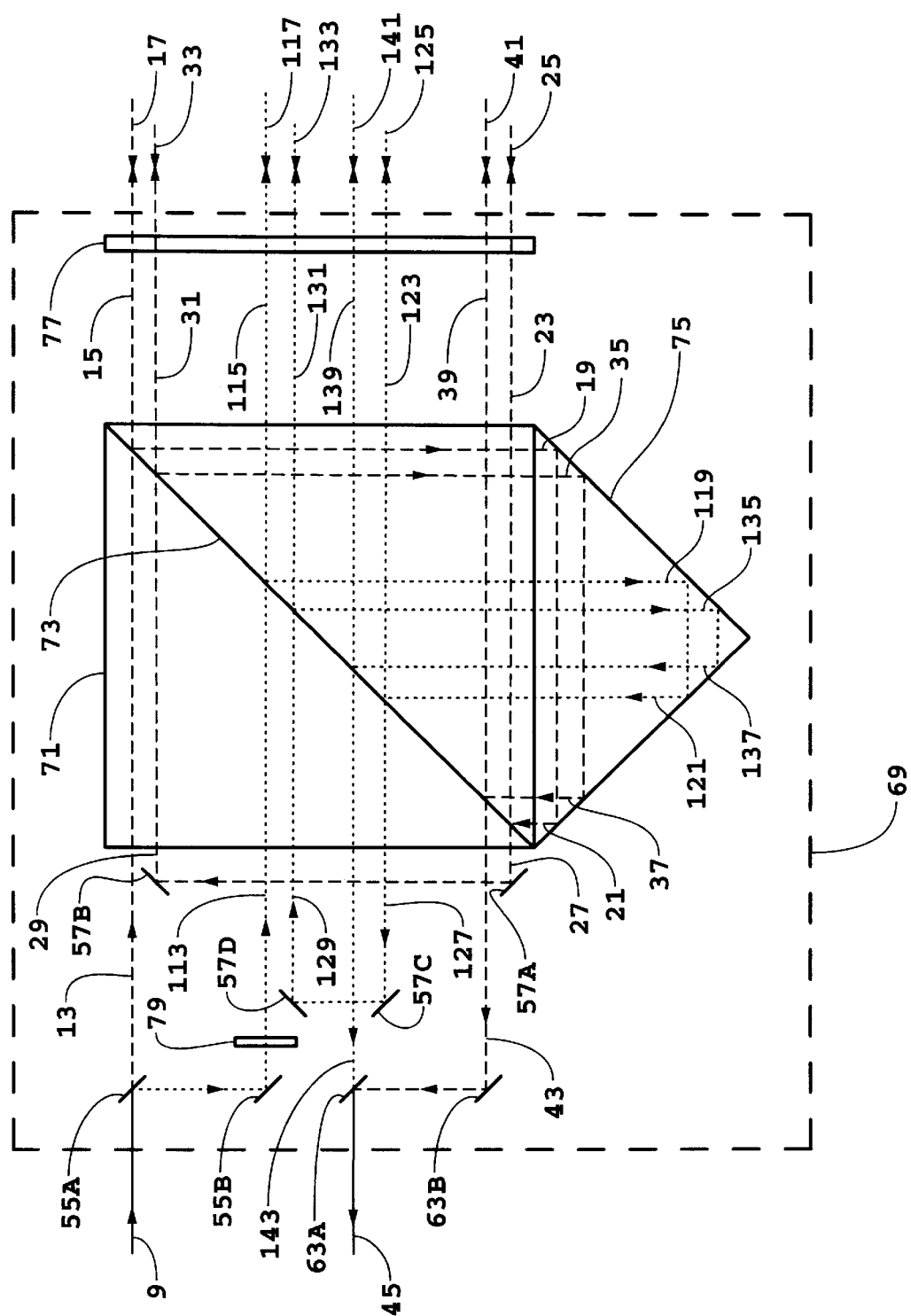

A differential plane mirror interferometer measures the optical path changes between two external plane mirrors. In addition, it is insensitive to thermal and mechanical disturbances that may occur in the interferometer beam splitting cube and associated optical components. Differential plane mirror interferometer 69 as shown in FIG. 1b has eight exit/return beams 17, 25, 33, 41, 117, 125, 133, and 141. Beams 17, 25, 33, and 41 originating from one frequency component of beam 9, the first frequency component, comprise beams for a reference leg and beams 117, 125, 133, and 141 originating from a second frequency component of beam 9 comprise beams for a measurement leg. Beams for which the first frequency component of beam 9 is the sole progenitor are indicated in FIG. 1b by dashed lines and beams for which the second frequency component of beam 9 is the sole progenitor are indicated in FIG. 1b by dotted lines.

Figure 1C:
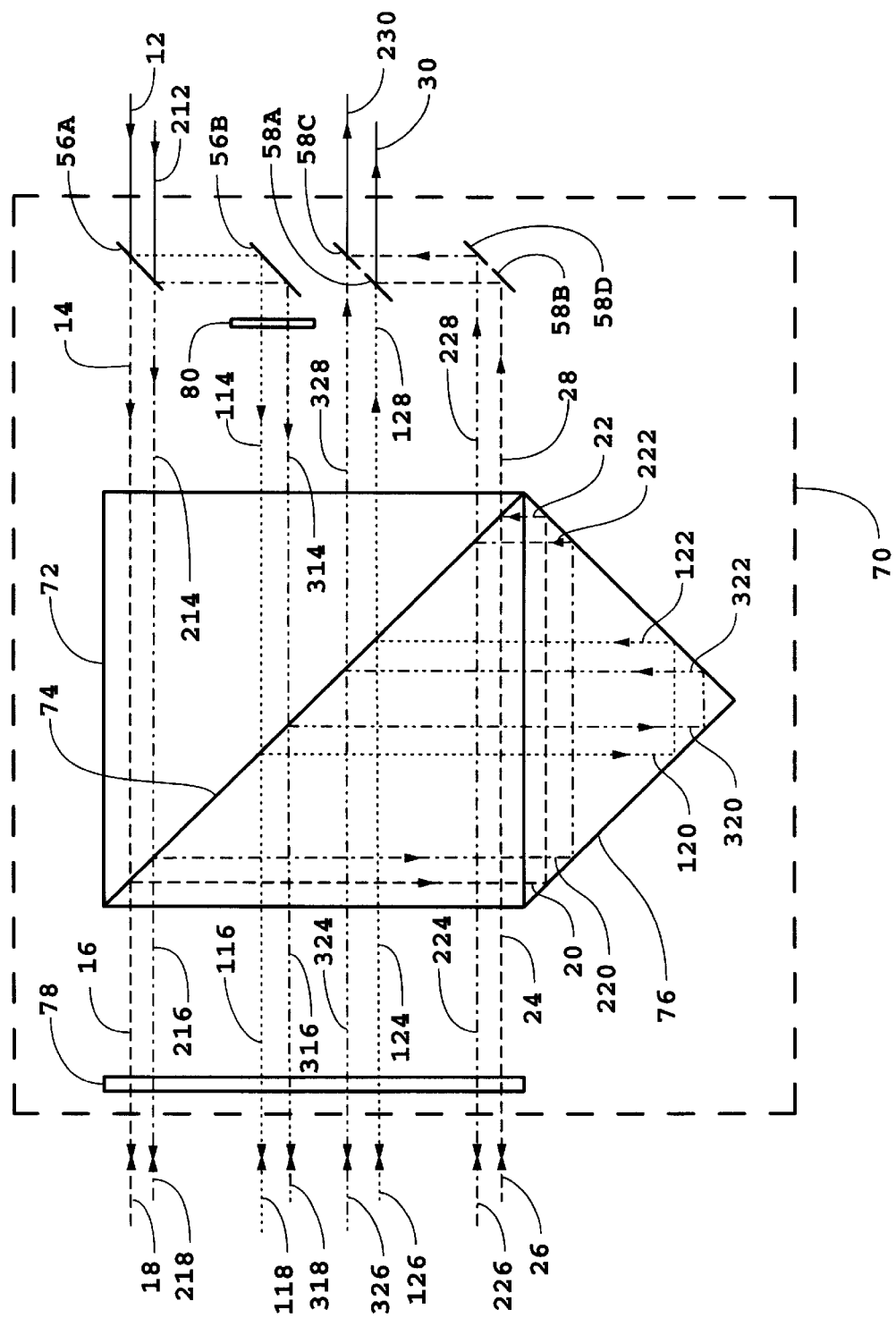

One differential plane mirror interferometer of differential plane mirror interferometer group 70 has four exit/return beams 18, 26, 118, and 126 (See FIG. 1c). Beams 18 and 26 originating from one frequency component, a first frequency component, of beam 12 comprise beams for a reference leg and beams 118 and 126 originating from a second frequency component of beam 12 comprise beams for a measurement leg. Beams for which the first frequency component of beam 12 is the sole progenitor are indicated in FIG. 1c by dashed lines and beams for which the second frequency component of beam 12 is the sole progenitor are indicated in FIG. 1c by dotted lines. A second differential plane mirror interferometer of differential plane mirror interferometer group 70 has four exit/return beams 218, 226, 318, and 326. Beams 218 and 226 originating from one frequency component, a first frequency component, of beam 212 comprise beams for a reference leg and beams 318 and 326 originating from a second frequency component of beam 212 comprise beams for a measurement leg. Beams for which the first frequency component of beam 212 is the sole progenitor are indicated in FIG. 1c by lines comprised of alternating dots and dashes and beams for which the second frequency component of beam 212 is the sole progenitor are indicated in FIG. 1c by lines comprised of alternating dot pairs and dashes.

Beams 17, 25, 33, 41, 117, 125, 133, and 141 are incident on beam splitter 65 (FIG. 1a) and are transmitted by coating 66, preferably a dichroic coating, as beams E17, E25, E33, E41, E117, E125, E133, and E141, respectively. Beams E17, E25, E33, E41, E117, E125, E133, and E141 are incident on external mirror system 90, illustrated in detail in FIG. 1d, which results in beams 43 and 143 (FIG. 1b). Beams 143 and 43 contain information at wavelength $\lambda_1$ about the optical path length through the gas in measuring path of external mirror system 90 and about the optical path length through a reference path, respectively.

Likewise, beams 18, 26, 118, 126, 218, 226, 318, and 326 are incident on beam splitter 65 and are reflected by dichroic coating 66 as beams E18, E26, E118, E126, E218, E226, E318, and E326, respectively. Beams E18, E26, E118, E126, E218, E226, E318, and E326 are incident on external mirror system 90, illustrated in FIG. 1e, which results in beams 28, 128, 228, and 328, respectively (FIG. 1c). Beams 128 and 328 contain information at wavelength $\lambda_2$ about optical path lengths through the gas in the measuring path of external mirror system 90, and beams 28 and 128 contain information at wavelength $\lambda_2$ about optical path lengths through a reference path.

Beam 43 is reflected by mirror 63B, a portion of which is reflected by beam splitter 63A, preferably a nonpolarizing type, to become one component of beam 45 (FIG. 1b). A portion of beam 143 is transmitted by beam splitter 63A to become a second component of beam 45. Beam 45 is a mixed beam, the first and second components of beam 45 having the same linear polarizations. Beam 45 exits the differential plane mirror interferometer 69.

Beam 28 (FIG. 1c) is reflected by mirror 58B, a portion of which is reflected by beam splitter 58A, preferably a nonpolarizing beam splitter, to become a first component of beam 30. A portion of beam 128 is transmitted by beam splitter 58A to become a second component of beam 30. Beam 30 is a mixed beam, the first and second components of beam 30 having the same linear polarizations.

Beam 228 is reflected by mirror 58D, a portion of which is reflected by beam splitter 58C, preferably a nonpolarizing beam splitter, to become a first component of beam 230. A portion of beam 328 is transmitted by beam splitter 58C to become a second component of beam 230. Beam 230 is a mixed beam, the first and second components of beam 230 having the same linear polarizations. Beams 30 and 230 exit differential plane mirror interferometer group 70.

The magnitude of phase shifts $\phi_1$, $\phi_2$, and $\phi_3$ are related to the difference $L_i$ between the round-trip physical length of path i of measurement path 98 and of reference paths shown in FIGS. 1a–1e according to the formulae $$\varphi_1(t) = \sum_{i=1}^{i=p_1} \varphi_{1,i}(t_i) = \sum_{i=1}^{i=p_1} L_i(t_i) k_1 n_{1i} + \zeta_1, \quad (2)$$

$$\varphi_2(t) = \sum_{i=1}^{i=p_2} \varphi_{2,i}(t_i) = \sum_{i=1}^{i=p_2} L_i(t_i) k_2 n_{2i} + \zeta_2,$$

$$\varphi_3(t) = \sum_{i=p_2+1}^{i=p_1} \varphi_{3,i}(t_i) = \sum_{i=p_2+1}^{i=p_1} L_i(t_i) k_2 n_{2i} + \zeta_3,$$

for the case of $p_1=2p_2$ where $n_{ji}$ are the refractive indices of gas in path i of measurement path 98 corresponding to wavenumber $k_j=(2\pi)/\lambda_j$. The nominal value for $L_i$ corresponds to twice the spatial separation of mirror surfaces 95 and 96 in external mirror system 90 (cf. FIGS. 1d and 1e). The phase offsets $\zeta_l$ comprise all contributions to the phase shifts $\phi_l$ that are not related to the measurement path 98 or reference paths. To those skilled in the art, the generalization to case when $p_1 \neq 2p_2$ is a straight forward procedure. In FIGS. 1b–1e, differential plane mirror interferometer 69, differential plane mirror interferometer group 70, beam splitter 65, and external mirror system 90 are configured so that $p_1=4$ and $p_2=2$, respectively, so as to illustrate in the simplest manner the function of the apparatus of the first preferred embodiment of the present invention.

Eqs. (2) are valid for the case where the combined paths for one wavelength and the combined paths for the second wavelength are substantially coextensive, a case chosen to illustrate in the simplest manner the function of the invention in the first embodiment. To those skilled in the art, the generalization to the case where the respective combined paths for the two different wavelengths are not substantially coextensive is a straight forward procedure.

Cyclic errors that produce non-linearities in distance measuring interferometry (cf. the cited articles by Bobroff) have been omitted in Eqs. (2). Techniques known to those skilled in the art can be used to either reduce the cyclic errors to negligible levels or compensate for the presence of cyclic errors, techniques such as using separated beams in the interferometer and/or separated beams in the delivery system for light beams from each light beam source to the interferometer [M. Tanaka, T. Yamagami, and K. Nakayama, "Linear Interpolation of Periodic Error in a Heterodyne Laser Interferometer at Subnanometer Levels," *IEEE Trans. Instrum. and Meas.*, 38(2), 552–554, 1989] and light beam sources with reduced polarization and/or frequency mixing. The technique of separated beams in the interferometer is incorporated for example in the first embodiment as shown in FIGS. 1a–1e.

The average time delay for a light beam to travel from the mirror 92 of external mirror system 90 to the point where the respective measurement and reference beams are mixed will in general be different for the light beams of differing wavelengths since the number of multiple passes for one light beam with a first wavelength being different from the number of multiple passes for a light beam with a second wavelength, the first and second wavelengths being different. The effect of the differences in the average time delay for light beams of differing wavelengths has been omitted in Eqs. (2) so as to not unduly complicate the description of the first embodiment.

The effect of the differences in the average time delay for light beams of differing wavelengths on the differences of respective phases is a second order effect, the effect being proportional to the velocity of the mirror 92 of external mirror system 90 and to approximately the instantaneous average value for $L_i$. For a speed of motion of the mirror 92 of 2 m/s and a instantaneous average value of $L_i$ of 2 m, the differences of respective phases is approximately 1 radian. Such phase differences occur at low frequencies, typically less than or of the order of 10 Hz. It will be apparent to those skilled in the art that such phase differences, the effect of the differences in the average time delay for light beams of differing wavelengths, can be modeled and compensated with knowledge of the velocity of the mirror 92 and the approximate instantaneous average value for $L_i$ in subsequent signal processing to the required precision imposed on the output data by the final end use application.

In a next step as shown in FIG. 1a, beams 45, 30, and 230 impinge upon photodetectors 85, 86, and 286, respectively, resulting in three interference signals, heterodyne signals $s_1$, $s_2$, and $s_3$, respectively, preferably by photoelectric detection. The signal $s_1$ corresponds to wavelength $\lambda_1$ and signals $s_2$ and $s_3$ correspond to the wavelength $\lambda_2$. The signals $s_l$ have the form $$s_l = A_l \cos[\alpha_l(t)], \; l=1, 2, \text{ and } 3, \tag{3}$$

where the time-dependent arguments $\alpha_l(t)$ are given by $$\alpha_1(t) = 2\pi f_1 t + \phi_1,$$
$$\alpha_2(t) = 2\pi f_2 t + \phi_2,$$
$$\alpha_3(t) = 2\pi f_2 t + \phi_3. \tag{4}$$

Heterodyne signals $s_1$, $s_2$, and $s_3$ are transmitted as electronic signals 103, 104, and 304, respectively, to electronic processor 109 for analysis in either digital or analog format, preferably in digital format.

A preferred method for electronically processing the heterodyne signals $s_1$, $s_2$, and $s_3$ is presented herewithin for the case when $l_1$ and/or $l_2$ are not low order integers. For the case when $l_1$ and $l_2$ are both low order integers and the ratio of the wavelengths matched to the ratio ($l_1/l_2$) with a relative precision sufficient to meet the required precision imposed on the output data by the end use application, the preferred procedure for electronically processing the heterodyne signals $s_1$, $s_2$, and $s_3$ is the same as the one subsequently set down for the second variant of the first embodiment of the present invention.

Figure 1D:
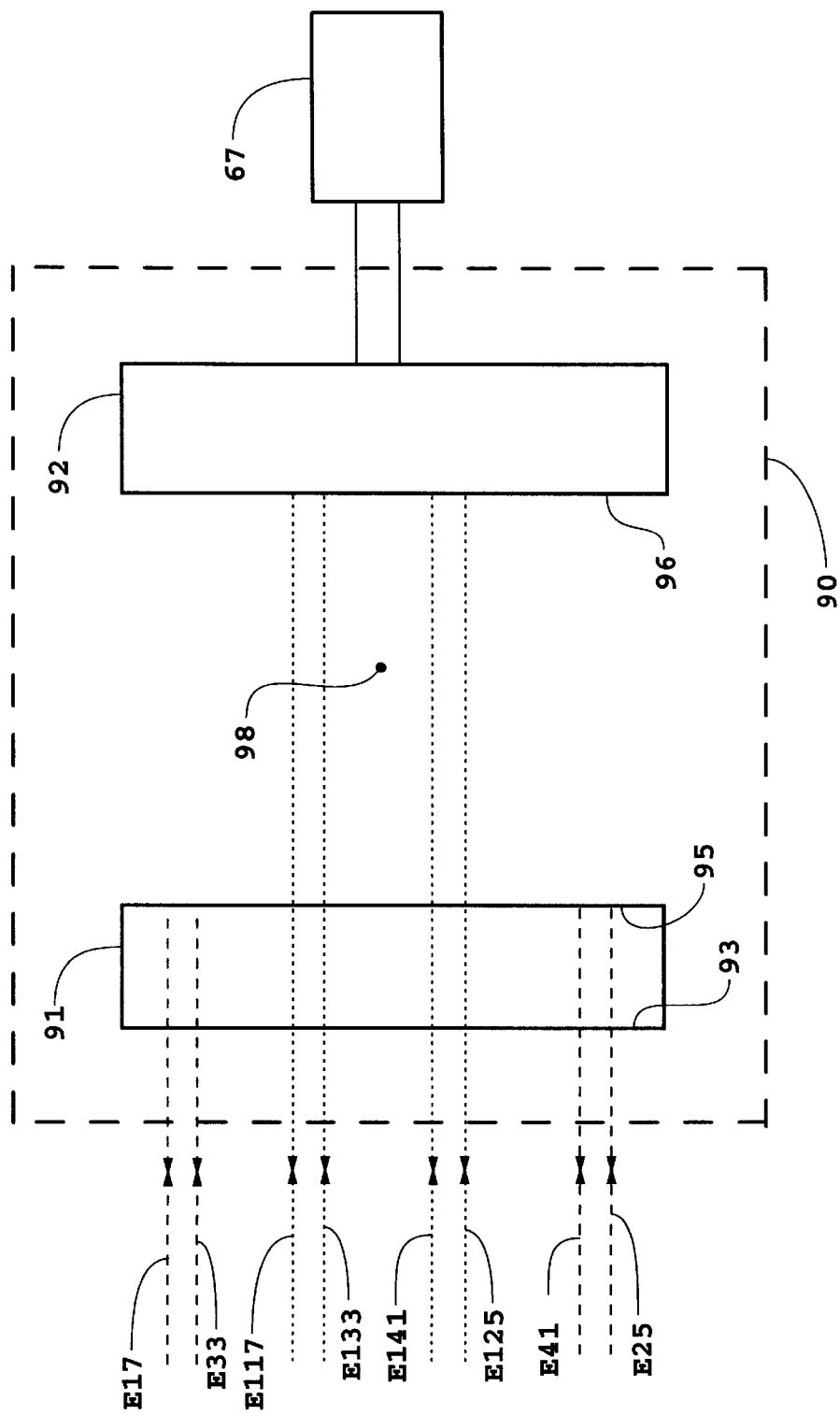
Figure 1E:
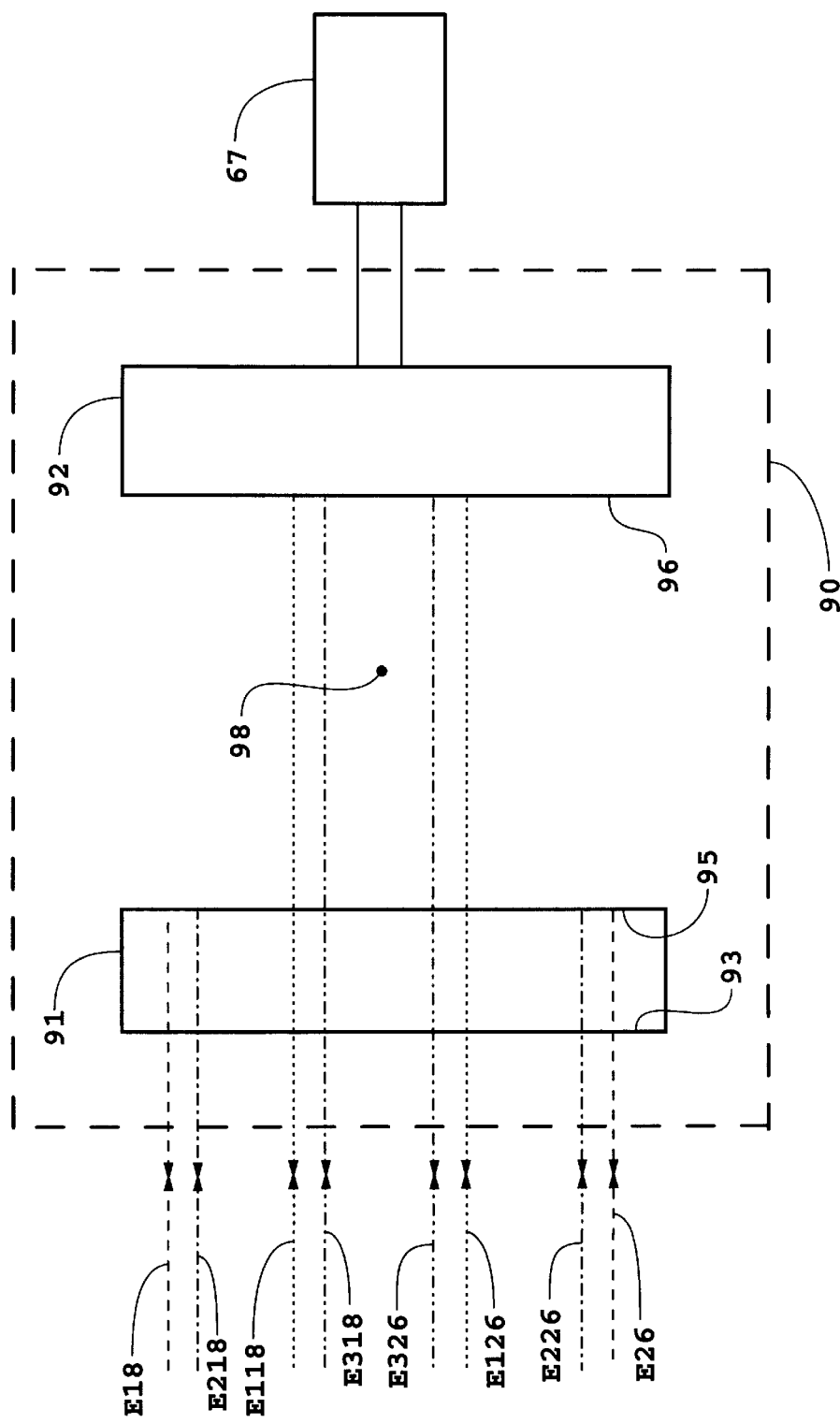
Figure 1F:
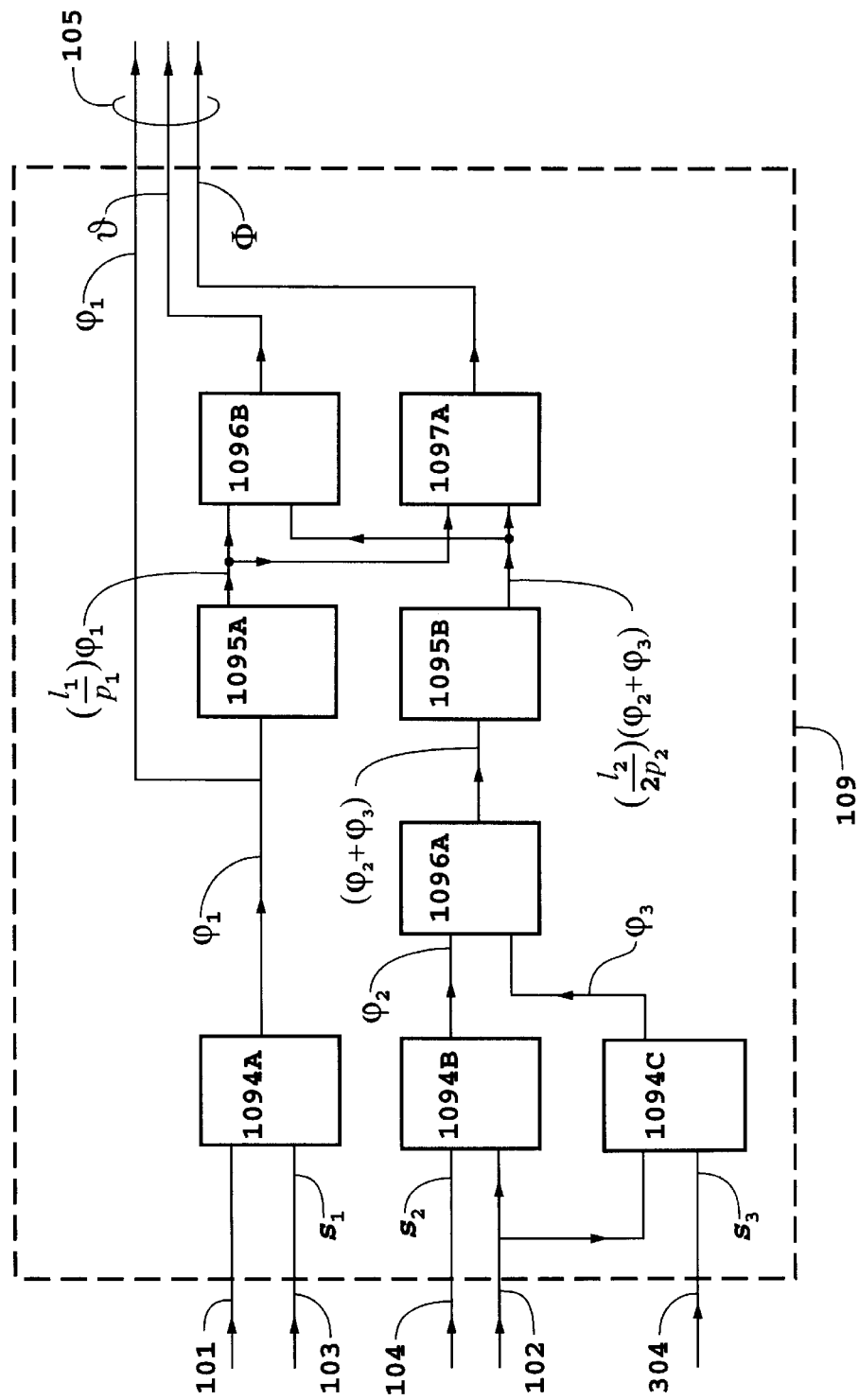

Referring now to FIG. 1f, electronic processor 109 comprises electronic processors 1094A, 1094B, and 1094C to determine the phases $\phi_1$, $\phi_2$, and $\phi_3$, respectively, by either digital or analog signal processes, preferably digital processes, using time-based phase detection such as a digital Hilbert transform phase detector [see section 4.1.1 of "Phase-locked loops: theory, design, and applications" 2nd ed. McGraw-Hill (New York) 1993, by R. E. Best] or the like and the phase of drivers 5 and 6.

The phases of drivers 5 and 6 are transmitted by electrical signals, reference signals 101 and 102, respectively, in either digital or analog format, preferably in digital format, to electronic processor 109. Reference signals, alternatives to reference signals 101 and 102, may also be generated by an optical pick off means and detectors (not shown in figures) by splitting off portions of beams 9 and 10 with beam splitters, preferably nonpolarizing beam splitters, mixing the portion of the beam 9 and the portion of the beam 10 that are split off, and detecting the mixed portions to produce heterodyne reference signals.

Referring again to FIG. 1f, electronic processor 109 comprises electronic processors 1096A to add together $\phi_2$ and $\phi_3$. Next, the phase $\phi_1$ and the resulting phase sum ($\phi_2 + \phi_3$) are multiplied by $l_1/p_1$ and $(l_2/p_2)(1/2)$, respectively, in electronic processors 1095A and 1095B, respectively, preferably by digital processing, resulting in phases $(l_1/p_1)\phi_1$ and $(l_2/p_2)(\phi_2+\phi_3)/2$. The phases $(l_1/p_1)\phi_1$ and $(l_2/p_2)(\phi_2+\phi_3)/2$ are next added together in electronic processor 1096B and subtracted one from the other in electronic processor 1097A, preferably by digital processes, to create the phases $\vartheta$ and $\Phi$, respectively. Formally, $$\vartheta = \left[\frac{l_1}{p_1}\varphi_1 + \frac{l_2}{p_2}\frac{(\varphi_2 + \varphi_3)}{2}\right], \tag{5}$$

$$\Phi = \left[\frac{l_1}{p_1}\varphi_1 - \frac{l_2}{p_2}\frac{(\varphi_2 + \varphi_3)}{2}\right]. \tag{6}$$

Note from Eqs. (5) and (6) that $\vartheta$ and $\Phi$ are not sensitive to tilt and/or yaw of either mirrors 91 or 92 of external mirror system 90, except for instantaneous changing of tilt and/or yaw through the effect of the differences in the average time delay for light beams of differing wavelengths such as described in relation to Eq. (2), of either mirror 91 or 92 of external mirror system 90 and insensitive to thermal and mechanical disturbances that may occur in the interferometer beam splitting cubes and associated optical components as a consequence of the use of differential plane mirror interferometers.

The phase effects in $\vartheta$ and $\Phi$ resulting from instantaneous changing of tilt and/or yaw of either mirror 91 or 92 through the effect of the differences in the average time delay for light beams of differing wavelengths are second order effects, the effects being proportional to the instantaneous angular velocity in either tilt or yaw and proportional to the approximate instantaneous average value for $L_i$ and occur at low frequencies, typically less than or of the order of 10Hz. The phase effects in $\vartheta$ and $\Phi$ resulting from instantaneous changing of tilt and/or yaw of either mirror 91 or 92 through the effect of the differences in the average time delay for light beams of differing wavelengths are typically less than 1 radian. It will be apparent to those skilled in the art that the phase effects in $\vartheta$ and $\Phi$ resulting from instantaneous changing of tilt and/or yaw of either mirror 91 or 92 can be modeled and compensated, with knowledge of the instantaneous tilt and/or yaw angular velocities of mirror 91 or 92 and the approximate instantaneous average value for $L_i$, in subsequent signal processing to the required precision imposed on the output data by the final end use application.

For a measuring path comprised of a vacuum, phase $\Phi$ should substantially be a constant independent of Doppler shifts due to a motion of one or both of the mirrors in the external mirror system 90, that motion which changes the mirror separation. This may not be the case in practice due to differences in the group delay experienced by the electrical signals $s_1$, $s_2$, and $s_3$. Group delay, often called envelope delay, describes the delay of a packet of frequencies and the group delay at a particular frequency is defined as the negative of the slope of the phase curve at the particular frequency [see H. J. Blinchikoff and A. I. Zverev, *Filtering in the Time and Frequency Domains*, Section 2.6, 1976 (Wiley, N.Y.)]. If phase $\Phi$ is not a constant for a measuring path comprised of a vacuum, techniques known to those skilled in the art can be used to compensate for departures of phase $\Phi$ from a constant (cf. Blinchikoff and Zveriv, ibid.). It is important to note that the group delay effects in $\Phi$ can not only be detected but can also be determined for a measuring path comprising a vacuum by measuring $\Phi$ as a function of different translational velocities of mirror 92 produced by translator 67. It is also important to note that the group delay effects in $\Phi$ can be significantly reduced by performing analog-to-digital conversion of signals $s_1$, $s_2$, and $s_3$ as close to the photoelectric detectors in detectors 85, 86, and 286, respectively, as practical followed by digital signal processing as opposed to transmitting the signals $s_1$, $s_2$, and $s_3$ as analog signals for subsequent analog signal processing and/or analog-to-digital conversion downstream. The compensation for a particular group delay can generally be introduced before or after, or in part before and in part after, the processing elements producing the particular group delay.

Electronic processor 109 additionally comprises processors 1094A to determine the phase shift $\phi_1$ using time-based phase detection or the like by analog or digital signal processing, preferably by digital processing, reference signal 101 serving as the reference signal in phase sensitive detection. The phases $\phi_1$, $\vartheta$, and $\Phi$ are transmitted to computer 110 as signal 105, in either digital or analog format, preferably in digital format.

The refractivity of the gas, $(n_1-1)$, can be calculated using the formula $$n_1 - 1 = \frac{\Gamma}{\chi L[1-(K/\chi)^2]}\{[\vartheta(K/\chi)-\Phi]-Q\}, \quad (7)$$

where L is the average of physical lengths $L_i$, $$\chi=(l_1 k_1 + l_2 k_2)/2, \quad (8)$$

$$K=(l_1 k_1 - l_2 k_2)/2, \quad (9)$$

$$\Gamma = \frac{n_1-1}{n_2-n_1}, \quad (10)$$

and second order correction terms have been omitted. The second order correction terms are due to a first order change in the index of refraction in the measurement path i from the average of the index of refraction over the measurement paths i and to the difference of the physical length $L_i$ from L. The quantity $\Gamma$ is the reciprocal dispersive power of the gas that is substantially independent of environmental conditions and turbulence in the gas. The offset term Q is defined as $$Q=\xi(K/\chi)-Z, \quad (11)$$

where $$\xi = \left(\frac{l_1}{p_1}\zeta_1 + \frac{l_2}{p_2}\frac{\zeta_2+\zeta_3}{2}\right), \quad (12)$$

$$Z = \left(\frac{l_1}{p_1}\zeta_1 - \frac{l_2}{p_2}\frac{\zeta_2+\zeta_3}{2}\right). \quad (13)$$

Values of $\Gamma$ may be computed from knowledge of the gas composition and from knowledge of the wavelength dependent refractivities of the gas constituents. For the example of $\lambda_1=0.63\,\mu m$, $\lambda_2=0.32\,\mu m$, and a standard atmosphere, $\Gamma\cong 24$.

In addition, Eq. (7) is valid for the case where the combined paths for optical beams at one wavelength are substantially coextensive with the combined paths for optical beams at a second wavelength, a preferred configuration which also serves to illustrate in the simplest manner the function of the invention in the second embodiment. To those skilled in the art, the generalization to the case where combined paths for optical beams at one wavelength are not substantially coextensive with the combined paths for optical beams at a second wavelength is a straight forward procedure.

For those applications related to distance measuring interferometry, the heterodyne phase $\phi_1$ and phases $\vartheta$ and $\Phi$ may be used to determine the distance L, independent of the effects of the refractive index of the gas in the measuring path of a distance measuring interferometer, using the formula $$L = \frac{1}{(\chi+K)}\left\{\frac{l_1}{p_1}(\varphi_1-\zeta_1) - \frac{\Gamma}{[1-(K/\chi)]}[(K/\chi)\vartheta-\Phi-Q]\right\}. \quad (14)$$

The ratio of the wavelengths can be expressed in terms of $(K/\chi)$ from Eqs. (8) and (9) with the result $$\frac{\lambda_1}{\lambda_2} = \left(\frac{l_1}{l_2}\right)\left[\frac{1-(K/\chi)}{1+(K/\chi)}\right]. \quad (15)$$

When operating under the condition $$|K/\chi| \ll \frac{(n_2-n_1)}{(n_2+n_1)}, \quad (16)$$

the ratio of the phases $\Phi$ and $\vartheta$ has the approximate value $$(\Phi/\vartheta) \cong -\frac{(n_2-n_1)}{(n_2+n_1)}. \quad (17)$$

Therefore, for the case of the first embodiment where the ratio of the wavelengths $(\lambda_1/\lambda_2)$ has a known approximate ratio value $l_1/l_2$, cf. Eq. (1), where $l_1$ and $l_2$ may assume integer and non-integer values, and the ratio of the wavelengths $(\lambda_1/\lambda_2)$ is the same as the ratio value $l_1/l_2$ to a relative precision of an order of magnitude or more less than the dispersion of the refractive index of the gas, $(n_2-n_1)$, times the relative precision $\epsilon$ desired for the measurement of the refractivity of the gas or of the change in the optical path length of the measurement leg due to the gas, expressed formally by the inequality $$\left|\frac{\lambda_1}{\lambda_2} - \frac{l_1}{l_2}\right| \ll \left(\frac{l_1}{l_2}\right)(n_2 - n_1)\varepsilon, \quad (18)$$

Eqs. (7) and (14) reduce to the more simple forms of $$n_1 - 1 = -\frac{\Gamma}{\chi L}(\Phi + Q), \quad (19)$$

$$L = \frac{1}{\chi}\left[\frac{l_1}{p_1}(\varphi_1 - \zeta_1) + \Gamma(\Phi + Q)\right], \quad (20)$$

respectively. It will also be obvious to someone skilled in the art to perform similar calculations for L with respect to $n_2$, $$(n_2-1)=(n_1-1)(1+1/\Gamma), \quad (21)$$

in place of or in addition to $n_1$.

In a next step, electronic processing means 109 transmits to the computer 110 $\phi_1$ and $\Phi$ as electronic signal 105 in either digital or analog format, preferably a digital format, for the computation of $(n_1-1)$ and/or L. The resolution of phase redundancy in $(1/l_1)\Phi$ is required in the computation of either $(n_1-1)$ or changes in L due to the gas using either Eqs. (19) or (20), respectively. In addition the resolution of the phase redundancy in $\phi_1$ is required in the computation of L using Eq. (20) and the resolution of phase redundancy in $\phi_1$ is required in the computation of changes L using Eq. (20) if $\chi$ is variable in time.

The equivalent wavelength comprising $(1/l_1)\Phi$ is significantly larger than either of the wavelengths $\lambda_1$ and $\lambda_2$ and as a consequence, produces a significant simplification in a procedure implemented for resolution of phase redundancy in $(1/l_1)\Phi$. The equivalent wavelength $\lambda_{(1/l_1)\Phi}$ for $(1/l_1)\Phi$ is $$\lambda_{(1/l_1)\Phi} = \frac{\lambda_1}{(n_2 - n_1)}. \quad (22)$$

For the example of $\lambda_1=0.633$ $\mu$m, $(n_1-1)\cong 3\times 10^{-4}$, and $(n_2-n_1)\cong 1\times 10^{-5}$, the equivalent wavelength given by Eq. (22) is $$\lambda_{eb} \cong 63 \text{ mm}. \quad (23)$$

Any one of several procedures may be easily employed to resolve the phase redundancy in $(1/l_1)\Phi$, given the equivalent wavelength as expressed by Eq. (22). For those applications where changes in the measurement path can be measured interferometrically, a feature for example of an application based on a distance measuring interferometer employed for measuring changes in the measurement path, the movable mirror 92 of the external mirror system 90 can be scanned by translator 67 in a controlled manner over a given length and the concomitant change in $(1/l_1)\Phi$ recorded. From the recorded change in $(1/l_1)\Phi$ and the length scanned, as recorded by the change in $\phi_1$, the equivalent wavelength $\lambda_{(1/l_1)\Phi}$ can be calculated. With the computed value for the equivalent wavelength $\lambda_{(1/l_1)\Phi}$, the phase redundancy in $(1/l_1)\Phi$ can be easily resolved in view of the relatively large value for the equivalent wavelength $\lambda_{(1/l_1)\Phi}$.

For those applications where the determination of the refractivity and/or or the change in the optical path length due to the gas in a measurement leg is made and mirror 92 of the external mirror system does not have a scanning capability, such as considered in the preceding paragraph, other procedures are available for the resolution of the phase redundancy of $(1/l_1)\Phi$. One procedure which may be employed to resolve the phase redundancy in $(1/l_1)\Phi$ is based on the use of a series of external mirror systems where the round-trip physical lengths L for the measurement legs of the external mirror systems form a geometric progression. The smallest or first round-trip physical length in the series will be approximately $\lambda_1/[4(n_2-n_1)]$ divided by the relative precision that the initial value of $(1/l_1)\Phi$ is known. The round-trip physical length of the second external mirror system 90 in the series will be approximately the round-trip physical length of the first external mirror system 90 divided by the relative precision that $\Phi$ is measured using the first external mirror system 90. This is a geometric progression procedure, the resulting round-trip physical lengths forming a geometric progression, which is continued until the round-trip physical length of the external mirror system 90 used to measure the refractivity or the change in optical path length due to the refractivity of the gas would be exceeded if the number of external mirror systems in series were incremented by one.

A third procedure is based upon the use of a source (not shown in FIGS. 1a–1e) of a series of known wavelengths and measuring $\Phi$ for these wavelengths. The number of known wavelengths required for the resolution of the phase redundancy is generally comprised of a small set because of the relatively large value for $\lambda_{(1/l_1)\Phi}$ as given by Eq. (22).

Another procedure to resolve the phase redundancy in $(1/l_1)\Phi$ would be to observe the changes in $(1/l_1)\Phi$ as the measuring path 98 is changed from gas to an evacuated state (the vacuum pump and requisite gas handling system are not shown in FIGS. 1a–1e) to resolve the phase redundancy in $(1/l_1)\Phi$. The problems normally encountered in measuring absolute values for refractivity and changes in the optical path length due to the refractivity of the gas based in part on changing the gas pressure from a non-zero value to a vacuum are not present in the first preferred embodiment because of the relative large equivalent wavelength of $(1/l_1)\Phi$.

The resolution of the phase redundancy in $\phi_1$ if required presents a problem similar to the one as subsequently described with respect to the required resolution of phase redundancy in $\vartheta$ in the second and third embodiments and variants thereof of the present invention. As a consequence, the procedures described for the resolution of phase redundancy in $\vartheta$ with respect to the second and third embodiments and variants thereof can be adapted for use in the resolution of the phase redundancy in $\phi_1$ if required.

The offset terms involving $\zeta_1$ or/and Q that are present in Eqs. (19) and (20) and defined in Eqs. (2) and (11) are terms that require some combination of determination and/or monitoring depending on whether $\chi$ is variable in time, whether the refractivity or/and the length L are to be determined, respectively, or whether changes in refractivity or/and the length L are to be determined, respectively. One procedure for the determination of $\zeta_1$ and Q is based on replacement of mirror 91 of the external mirror system 90 with a mirror R91 (not shown in FIGS. 1d and 1e) having a surface R93 corresponding to surface 93 of mirror 91 coated so as be a reflecting surface for both wavelengths $\lambda_1$ and $\lambda_2$ and measuring the resulting values of $\phi_1$ and $\Phi$. Let the resulting values of $\phi_1$ and $\Phi$ be $\phi_{1R}$ and $\Phi_R$, respectively. Quantities $\zeta_1$ and Q are related to $\phi_{1R}$ and $\Phi_R$, respectively, as evident from Eqs. (2) and (19) by the formulae $$\zeta_1 = \phi_{1R}, \quad (24)$$

$$Q = -\Phi_R. \quad (25)$$

The non-electronic contributions to $\zeta_1$ and Q should be substantially constant in time because of the significant level of compensation that takes place in the differential plane mirror interferometer 69, the differential plane mirror interferometer group 70, beam splitter 65, and external mirror system 90. The electronic contributions to $\zeta_1$ and Q may be monitored by purely electronic means (not shown).

It will be apparent to someone skilled in the art that as a consequence of the incorporation of beam splitter 65 in the first preferred embodiment, the measuring paths for beams at $\lambda_1$ and $\lambda_2$ are coextensive in external mirror system 90, so that the dispersion of the gas can serve as a proxy to high precision for the gas column density in the measuring path, whereas polarizing coating 73 of beam splitter 71 and quarter-wave retardation plate 77 need only meet performance specifications at $\lambda_1$ while polarizing coating 74 of beam splitter 72 and quarter-wave retardation plate 78 need only meet performance specifications at $\lambda_2$. This assignment of critical operations according to wavelength as disclosed in the first embodiment can be an important feature of the present invention when requiring use of three or more light beams with different wavelengths having coextensive measuring paths in the gas, particularly in high precision applications such as the case of micro-lithographic fabrication of integrated circuits. However, the assignment of operations according to wavelength need not be done as disclosed in the first preferred embodiment, e.g. the function of beam splitters 71 and 72 being achieved by a single beam splitter with an appropriately modified polarizing surface, without departing from the spirit or scope of the present invention.

The description of the first preferred embodiment noted that the configuration of interferometers illustrated in FIGS. 1a–1e are known in the art as differential plane mirror interferometers. Other forms of the differential plane mirror interferometer and forms of other interferometers such as the plane mirror interferometer or the angle-compensating interferometer or similar device such as is described in an article entitled "Differential interferometer arrangements for distance and angle measurements: Principles, advantages and applications" by C. Zanoni, *VDI Berichte Nr*. 749, 93–106 (1989), is preferably incorporated into the apparatus of the first embodiment of the present invention as when working with stages commonly encountered in the micro-lithographic fabrication of integrated circuits without departing from the spirit or scope of the present invention.

FIG. 1b depicts in schematic form one embodiment of the differential plane mirror interferometer 69 shown in FIG. 1a. It operates in the following way: beam 9 is incident on beam splitter 55A, preferably a polarizing beam splitter, with a portion of beam 9 being transmitted as beam 13. A second portion of beam 9 reflected by beam splitter 55A is reflected by mirror 55B and then transmitted by half-wave phase retardation plate 79 as beam 113, the half-wave phase retardation plate 79 rotating the plane of polarization of the reflected portion of beam 9 by 90°. Beams 13 and 113 have the same polarizations but still have different frequencies. The function of beam splitter 55A and mirror 55B is to spatially separate the two frequency components of beam 9 using conventional polarization techniques.

Beams 13 and 113 enter polarizing beam splitter 71, which has a polarizing coating 73, and are transmitted as beams 15 and 115, respectively. Beams 15 and 115 pass through quarter-wave phase retardation plate 77 and are converted into circularly polarized beams 17 and 117, respectively. Beams 17 and 117 are transmitted by beam splitter 65 with dichroic coating 66, reflected back on themselves by mirrors within external mirror system 90 as illustrated in FIG. 1d, pass back through beam splitter 65, and subsequently pass back through quarter-wave retardation plate 77 and are converted back into linearly polarized beams that are orthogonally polarized to the original incident beams 15 and 115. These beams are reflected by polarizing coating 73 to become beams 19 and 119, respectively. Beams 19 and 119 are reflected by retroreflector 75 to become beams 21 and 121, respectively. Beams 21 and 121 are reflected by polarizing coating 73 to become beams 23 and 123, respectively. Beams 23 and 123 pass through quarter-wave phase retardation plate 77 and are converted into circularly polarized beams 25 and 125, respectively. Beams 25 and 125 are transmitted by beam splitter 65, reflected back on themselves by mirrors within external mirror system 90 as illustrated in FIG. 1d, pass back through beam splitter 65, and subsequently pass back through quarter-wave retardation plate 77 and are converted back into linearly polarized beams, the linear polarizations being the same as the linear polarizations of the original incident beams 15 and 115. These beams are transmitted by polarizing coating 73 to become beams 27 and 127, respectively. Beam 27 is reflected by mirrors 57A and 57B and beam 127 is reflected by mirrors 59C and 59D to become beams 29 and 129, respectively.

Beams 29 and 129 enter polarizing beam splitter 71 and are transmitted by polarizing beam splitter 71 with polarizing coating 73 as beams 31 and 131, respectively. Beams 31 and 131 pass through quarter-wave phase retardation plate 77 and are converted into circularly polarized beams 33 and 133, respectively. Beams 33 and 133 are transmitted by beam splitter 65, reflected back on themselves by mirrors within external mirror system 90 as illustrated in FIG. 1d, pass back through beam splitter 65, and subsequently pass back through quarter-wave retardation plate 77 and are converted back into linearly polarized beams that are orthogonally polarized to the original incident beams 31 and 131. These beams are reflected by polarizing coating 73 to become beams 35 and 135, respectively. Beams 35 and 135 are reflected by retroreflector 75 to become beams 37 and 137, respectively. Beams 37 and 137 are reflected by polarizing coating 73 to become beams 39 and 139, respectively. Beams 39 and 139 pass through quarter-wave phase retardation plate 77 and are converted into circularly polarized beams 41 and 141, respectively. Beams 41 and 141 are transmitted by beam splitter 65, reflected back on themselves by mirrors within external mirror system 90 as illustrated in FIG. 1d, pass back through beam splitter 65, and subsequently pass back through quarter-wave retardation plate 77 and are converted back into linearly polarized beams, the linear polarizations being the same as the linear polarizations of the original incident beams 15 and 115. These beams are transmitted by polarizing coating 73 to become beams 43 and 143, respectively. Beams 43 and 143 contain information at wavelength $\lambda_1$ about the optical path lengths through the gas in the measurement path 98 wherein the effects of the refractivity of the gas is to be determined and about the optical path lengths through reference leg, respectively.

Beam 43 is reflected by mirror 63B, and then a portion reflected by beam splitter 63A, preferably a nonpolarizing type, as a first component of beam 45. Beam 143 is incident on beam splitter 63A with a portion of beam 143 being transmitted as a second component of beam 45, the first and second components of beam 45 having the same linear polarizations but still having different frequencies.

FIG. 1c depicts in schematic form one embodiment of differential plane mirror interferometer group 70 shown in FIG. 1a. It operates in the following way: beam 12 is incident on beam splitter 56A, preferably a polarizing beam splitter, with a portion of beam 12 being transmitted as beam 14. A second portion of beam 12, reflected by beam splitter 56A, is reflected by mirror 56B and then transmitted by half-wave phase retardation plate 80 as beam 114, the half-wave phase retardation plate 80 rotating the plane of polarization of the incident portion of beam 12 by 90°. Beams 14 and 114 have the same polarizations but different frequencies. The function, in part, of beam splitter 56A and mirror 56B is to spatially separate the two frequency components of beam 12 using conventional polarization techniques.

Beams 14 and 114 enter polarizing beam splitter 72, which has a polarizing coating 74, and are transmitted as beams 16 and 116, respectively. Beams 16 and 116 pass through quarter-wave phase retardation plate 78 and are converted into circularly polarized beams 18 and 118, respectively. Beams 18 and 118 are reflected by beam splitter 65 with dichroic coating 66, reflected back on themselves by mirrors within external mirror system 90 as illustrated in FIG. 1e, reflected by surface 66 of beam splitter 65 a second time, and subsequently pass back through quarter-wave retardation plate 78 and converted back into linearly polarized beams that are orthogonally polarized to the original incident beams 16 and 116. These beams are reflected by polarizing coating 74 to become beams 20 and 120, respectively. Beams 20 and 120 are reflected by retroreflector 76 to become beams 22 and 122, respectively.

Beams 22 and 122 are reflected by polarizing coating 74 to become beams 24 and 124, respectively. Beams 24 and 124 pass through quarter-wave phase retardation plate 78 and are converted into circularly polarized beams 26 and 126, respectively. Beams 26 and 126 are reflected by surface 66 of beam splitter 65, reflected back on themselves by mirrors within external mirror system 90 as illustrated in FIG. 1e, reflected by surface 66 of beam splitter 65 a second time, and subsequently pass back through quarter-wave retardation plate 78 and are converted back into linearly polarized beams, the same linear polarizations as the linear polarizations of the original incident beams 16 and 116. These beams are transmitted by polarizing coating 74 to become beams 28 and 128, respectively. Beams 28 and 128 contain information at wavelength $\lambda_2$ about the optical path lengths through the gas in measurement path 98 wherein the effects of the refractivity of the gas is to be determined and about the optical path lengths through the reference leg, respectively.

Beam 28 is reflected by mirror 58B, and then a portion reflected by beam splitter 58A, preferably a nonpolarizing type, as a first component of beam 30. Beam 128 is incident on beam splitter 58A with a portion of beam 128 being transmitted as a second component of beam 30, the first and second components of beam 30 having the same linear polarizations but still having different frequencies.

Beam 212 is incident on beam splitter 56A with a portion of beam 212 being transmitted as beam 214. A second portion of beam 212 is reflected by beam splitter 56A, subsequently reflected by mirror 56B, and then transmitted by half-wave phase retardation plate 80 as beam 314, the half-wave phase retardation plate 80 rotating the plane of polarization of the incident portion of beam 212 by 90°. Beams 214 and 314 have the same polarizations but still have different frequencies. The function, in part, of beam splitter 56A and mirror 56B is to spatially separate the two frequency components of beam 212 using conventional polarization techniques.

Beams 214 and 314 enter polarizing beam splitter 72, which has a polarizing coating 74, and are transmitted as beams 216 and 316, respectively. Beams 216 and 316 pass through quarter-wave phase retardation plate 78 and are converted into circularly polarized beams 218 and 318, respectively. Beams 218 and 318 are reflected by surface 66 of beam splitter 65, reflected back on themselves by mirrors within external mirror system 90 as illustrated in FIG. 1e, reflected by surface 66 of beam splitter 65 a second time, and subsequently pass back through quarter-wave retardation plate 78 and are converted back into linearly polarized beams that are orthogonally polarized to the original incident beams 216 and 316. These beams are reflected by polarizing coating 74 to become beams 220 and 320, respectively. Beams 220 and 320 are reflected by retroreflector 76 to become beams 222 and 322, respectively. Beams 222 and 322 are reflected by polarizing coating 74 to become beams 224 and 324, respectively. Beams 224 and 324 pass through quarter-wave phase retardation plate 78 and are converted into circularly polarized beams 226 and 326, respectively. Beams 226 and 326 are reflected by surface 66 of beam splitter 65, reflected back on themselves by mirrors within external mirror system 90 as illustrated in FIG. 1e, reflected by surface 66 of beam splitter 65 a second time, and subsequently pass back through quarter-wave retardation plate 78 and converted back into linearly polarized beams, the linear polarizations being the same as the linear polarizations of the original incident beams 216 and 316. These beams are transmitted by polarizing coating 74 to become beams 228 and 328, respectively. Beams 228 and 328 contain information at wavelength $\lambda_2$ about the optical path lengths through the gas in measurement path 98 wherein the effects of the refractivity of the gas is to be determined and about the optical path lengths through the reference leg, respectively.

Beam 228 is reflected by mirror 58D and then a portion reflected by beam splitter 58C, preferably a nonpolarizing type, as a first component of beam 230. Beam 328 is incident on beam splitter 58C with a portion of beam 328 being transmitted as a second component of beam 230, the first and second components of beam 230 having the same linear polarizations but still having different frequencies.

A first variant of the first preferred embodiment is disclosed wherein the description of the apparatus of the first variant of the first embodiment is the same as that given for the apparatus of the first embodiment except with regard to the frequencies $f_1$ and $f_2$ of drivers 5 and 6, respectively, shown in FIG. 1a. In the first variant of the first embodiment, the frequencies of the two drivers 5 and 6 are the same, i.e. $f_1=f_2$. This feature of the first variant of the first embodiment eliminates the effects of differences in group delays in the first embodiment resulting from $f_1 \neq f_2$. The remaining description of the first variant of the first embodiment is the same as corresponding portions of the description given for the first embodiment.

Reference is now made to FIGS. 1a–1e and 1g which taken together depict in diagrammatic form a second variant of the first preferred embodiment of the present invention for measuring and monitoring the refractivity of a gas in a measurement path and/or the change in the optical path length of the measurement path due to the gas wherein either or both the refractive index of the gas and the physical length of the measurement path may be changing and where the stability of the adopted light sources is sufficient and the wavelengths of the light beams generated by the adopted light sources are harmonically related to a relative precision sufficient to meet the required precision imposed on the output data by the final end use application. The condition wherein the wavelengths are approximately harmonically related corresponds to the special case of the first embodiment in which the ratio $(l_1/l_2)$ is expressible as the ratio of low order non-zero integers $(p_1/p_2)$, i.e.

$$l_1 = p_1, l_2 = p_2, \left(\frac{l_1}{l_2}\right) = \left(\frac{p_1}{p_2}\right), p_1, p_2 = 1, 2, \ldots, p_1 \neq p_2, \quad (26)$$

which corresponds to the wavelengths $\lambda_1$ and $\lambda_2$ being approximately harmonically related.

The description of the sources of light beams 9 and 10 and of light beams 9 and 10 for the second variant of the first embodiment is the same as that for description of the sources of light beams 9 and 10 and of light beams 9 and 10 given for the first embodiment with the additional requirement that the wavelengths be harmonically related to a relative precision sufficient to meet the required precision imposed on the output data by the final end use application. The description of the apparatus for the second variant of the first embodiment depicted in FIGS. 1a–1e is the same as corresponding portions of the description given for the first embodiment for the case where $p_1=4$ and $p_2=2$.

Figure 1G:
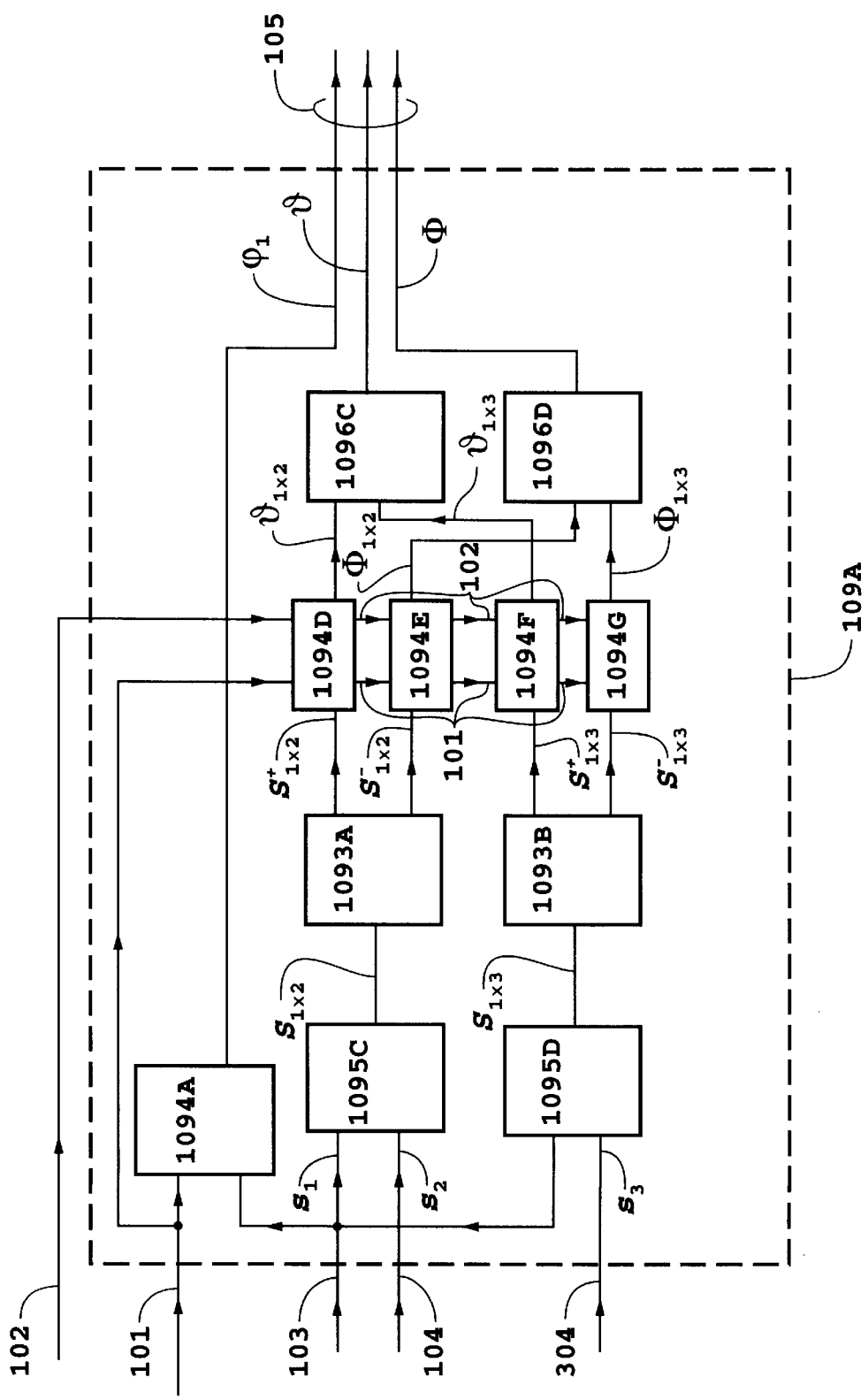
FIG. 1g is a drawing showing a block diagram of the processing electronics 109A for the second variant of the first embodiment.

Referring now to FIG. 1g, electronic processor 109A preferably comprises electronic processor 1095C for electronically multiplying together, either as an analog or digital process, preferably a digital process, heterodyne signals $s_1$ and $s_2$ to create a superheterodyne signal $S_{1\times2}$ having the mathematical form $$S_{1\times2}=s_1 s_2. \quad (27)$$

The superheterodyne signal $S_{1\times2}$ is comprised of two sidebands with a suppressed carrier and may be rewritten as $$S_{1\times2}=S_{1\times2}^{+}+S_{1\times2}^{-} \quad (28)$$

where $$S_{1\times2}^{+}=\tfrac{1}{2}A_1 A_2 \cos(2\pi\nu t+\vartheta_{1\times2}), \quad (29)$$

$$S_{1\times2}^{-}=\tfrac{1}{2}A_1 A_2 \cos(2\pi F t+\Phi_{1\times2}), \quad (30)$$

$$\nu=(f_1+f_2), \quad (31)$$

$$\vartheta_{1\times2}=(\phi_1+\phi_2), \quad (32)$$

$$F=(f_1-f_2), \quad (33)$$

$$\Phi_{1\times2}=(\phi_1-\phi_2). \quad (34)$$

The superheterodyne signal $S_{1\times2}$ is therefore comprised of two sidebands, $S_{1\times2}^{+}$ and $S_{1\times2}^{-}$, of equal amplitude, one sideband with frequency $\nu$ and phase $\vartheta_{1\times2}$ and a second sideband with frequency F and phase $\Phi_{1\times2}$.

In a next step, the sidebands $S_{1\times2}^{+}$ and $S_{1\times2}^{-}$, are separated by electronic processor 1093A through high pass and low pass filtering or any of the like techniques for separating two signals that are separated in frequency. The frequency F of the lower frequency sideband of the superheterodyne signal is chosen to be very much smaller than the frequency $\nu$ of the higher frequency sideband of the superheterodyne signal, so as to make it easier to calculate the phase $\Phi_{1\times2}$ with high resolution, considerably simplifying the separating task of processor 1093A. Electronic processor 109A further comprises electronic processor 1094D and 1094E to determine the phases $\vartheta_{1\times2}$ and $\Phi_{1\times2}$, respectively, using time-based phase detection such as a digital Hilbert transform phase detector (see R. E. Best, ibid.) or the like and the phases of the drivers 5 and 6.

Electronic processor 109A further comprises electronic processor 1095D which electronically multiplies together, either as an analog or digital process, preferably a digital process, heterodyne signals $s_1$ and $s_3$ to create a superheterodyne signal $S_{1\times3}$ having the mathematical form $$S_{1\times3}=s_1 s_3. \quad (35)$$

The superheterodyne signal $S_{1\times3}$ also comprises two sidebands with a suppressed carrier and may be rewritten as $$S_{1\times3}=S_{1\times3}^{+}+S_{1\times3}^{-} \quad (36)$$

where $$S_{1\times3}^{+}=\tfrac{1}{2}A_1 A_3 \cos(2\pi\nu t+\vartheta_{1\times3}), \quad (37)$$

$$S_{1\times3}^{-}=\tfrac{1}{2}A_1 A_3 \cos(2\pi F t+\Phi_{1\times3}), \quad (38)$$

$$\vartheta_{1\times3}=(\phi_1+\phi_3), \quad (39)$$

$$\Phi_{1\times3}=(\phi_1-\phi_3). \quad (40)$$

The superheterodyne signal $S_{1\times3}$ therefore comprises two sidebands, $S_{1\times3}^{+}$ and $S_{1\times3}^{-}$, of equal amplitude, one sideband with frequency $\nu$ and phase $\vartheta_{1\times3}$ and a second sideband with frequency F and phase $\Phi_{1\times3}$.

In a next step, the sidebands $S_{1\times3}^{+}$ and $S_{1\times3}^{-}$, are separated by electronic processor 1093B through high pass and low pass filtering or any of the like techniques for separating two signals that are separated in frequency. As noted in the discussion of electronic processor 1093A, the frequency F of the lower frequency sideband of superheterodyne signal $S_{1\times3}$ is chosen to be very much smaller than the frequency $\nu$ of the higher frequency sideband of superheterodyne signal $S_{1\times3}$, considerably simplifying the separating task of processor 1093B. Electronic processor 109A further comprises processor 1094F and 1094G, respectively, to determine the phases $\vartheta_{1\times3}$ and $\Phi_{1\times3}$ using time-based phase detection such as a digital Hilbert transform phase detector (see Best ibid.) or the like and the phases of the drivers 5 and 6.

Subsequently, the phases $\vartheta_{1\times2}$ and $\vartheta_{1\times3}$ are added together and divided by 2 in electronic processor 1096C, by an analog or digital process, preferably a digital process, and phases $\Phi_{1\times2}$ and $\Phi_{1\times3}$ are added together and divided by 2 in electronic processor 1096D, by an analog or digital process, preferably a digital process, to create the phases $\vartheta$ and $\Phi$, respectively. Formally, $$\vartheta = \frac{(\vartheta_{1\times2}+\vartheta_{1\times3})}{2} = \left[\varphi_1 + \frac{(\varphi_2+\varphi_3)}{2}\right], \quad (41)$$

$$\Phi = \frac{(\Phi_{1\times2}+\Phi_{1\times3})}{2} = \left[\varphi_1 - \frac{(\varphi_2+\varphi_3)}{2}\right]. \quad (42)$$

Note from Eqs. (41) and (42) that $\vartheta$ and $\Phi$ are not sensitive to tilt and/or yaw of mirrors 91 and 92 of external mirror system 90, except for instantaneous changing of tilt and/or yaw of mirrors 91 and 92 through the second order effect of the differences in the average time delay for light beams of differing wavelengths such as described in relation to Eqs. (5) and (6), and insensitive to thermal and mechanical disturbances that may occur in the interferometer beam splitting cubes and associated optical components as a consequence of the use of differential plane mirror interferometers.

Electronic processor 109A, and shown in FIG. 1g, comprises electronic processor 1094A to determine phase $\phi_1$ from heterodyne signal $s_1$ using time-based phase sensitive detection with reference signal 101 or the like, preferably a digital process. Phases $\phi_1$, $\tilde{\vartheta}$, and $\Phi$ are transmitted, in digital or analog format, preferably a digital format, to computer 110 as signal 105 for the computation of $(n_1-1)$ and/or L.

The refractivity $(n_1-1)$ of the gas or changes in L due to the gas in the measuring path can be expressed in terms of other quantities obtained in the second variant of the first embodiment by Eqs. (6), (11), (12), (13), (19), and (20) with $$l_1 = p_1, \ l_2 = p_2. \tag{43}$$

The remaining discussion of the second variant of the first embodiment is the same as corresponding portions of the descriptions given for the first embodiment.

The principal advantage of the second variant of the first embodiment is an option for the execution of critical electronic processing steps, such as the determination of phases $\Phi_{1\times2}$ and $\Phi_{1\times3}$ at substantially identical frequencies, the frequencies of heterodyne signals $s_1$, $s_2$, and $s_3$ being substantially identical in regard to $f_1$ being close to $f_2$ and to the Doppler shifts produced by the translation of mirror 92 of external mirror system 90 being substantially the same in $s_1$, $s_2$, and $s_3$, so as to substantially reduce the potential for generating differences in group delays experienced by heterodyne signals having significantly different frequencies. The discussion of the effects of group delay for the second variant of the first embodiment is the same as corresponding portions of the description given for the first embodiment.

A preferred second variant of the first embodiment of the invention having been disclosed in the previous paragraphs, the underlying advantages of the invention will be made more clear by the following discussion. It is evident from the calculation of the refractivity by Eq. (7) or the calculation of the effect of the refractivity of the gas in the optical path by Eq. (14), that the required accuracies to which the phases $\tilde{\vartheta}$ and $\Phi$ must be determined are related to the values of the wavenumbers K and $\chi$. In that the frequency F can be very much smaller than the frequency $\nu$, and since it is generally easier to calculate the phase with high resolution of an electronic signal of lower frequency, it is generally most advantageous to rely on a high-accuracy measurement of the superheterodyne sideband phase $\Phi$. This is readily achieved in the inventive apparatus when the wavenumbers K and $\chi$ are related according to Eq. (16), the calculation of the refractivity by Eq. (7) or the calculation of the effect of the refractivity of the gas on the optical path by Eq. (14) substantially not involving the superheterodyne sideband phase $\tilde{\vartheta}$ at all. Further, the magnitude of the superheterodyne sideband phase $\Phi$ is less than the magnitude of the superheterodyne sideband phase $\tilde{\vartheta}$, less dependent by a factor of approximately $(n_2-n_1)/(n_2+n_1)$ as expressed by Eq. (17). This greatly improves the potential phase detection accuracy for moving objects, such as are commonly encountered in micro-lithography equipment. A corresponding analysis and summary also applies to the first embodiment and to the first variant of the first embodiment wherein there is an improvement in the phase detection accuracy for moving objects substantially proportional to the relative precision that the approximate ratio value $l_1/l_2$ can be expressed as the ratio of low order non-zero integers, all other factors being the same.

Eq. (18) also forms the basis for a conclusion that sources 1 and 2 need not be phase locked for the first variant of the first preferred embodiment. Eq. (18) is actually a weak condition when viewed in terms of a phase-locked requirement for sources 1 and 2. Consider for an example a desired precision of $\epsilon \cong 3\times10^{-6}$ for measuring the refractivity $(n_1-1)$ of the gas or for the change in the optical path length of the measurement leg due to the gas, corresponding to a relative distance measuring precision of approximately $1\times10^{-9}$ in a distance measuring interferometer, $(n_1-1)\cong 3\times10^{-4}$, and $(n_2-n_1)\cong 1\times10^{-5}$. For the example, the condition expressed by Eq. (18) written in terms of source frequencies $\nu_1$ and $\nu_2$ instead of wavelengths $\lambda_1$ and $\lambda_2$, respectively, is $$\left| \nu_2 - \frac{p_1}{p_2} \nu_1 \right| \ll 3\times 10^{-11} \nu_2. \tag{44}$$

For source wavelengths in the visible part of the spectrum and for low order integers for $p_1$ and $p_2$, Eq. (44) translates into a condition $$\left| \nu_2 - \frac{p_1}{p_2} \nu_1 \right| \ll 30\,\text{kHz}. \tag{45}$$

The result expressed in Eq. (45) is clearly a significantly less restrictive condition on the frequencies of sources 1 and 2 than a phase-locked condition.

The first embodiment and first and second variants thereof are each configured with differential plane mirror interferometers using an even number of passes of a beam through measurement path 98 of external mirror system 90. With an even number of passes by a beam in a differential plane mirror interferometer, the direction of propagation of an exit beam from the measurement leg and the direction of propagation of the corresponding exit beam from the reference leg are independent of tilt or yaw of either mirror in the external mirror system 90, in particular mirror 92, although there will be certain lateral shear of one of the exit beams relative to the other of the exit beams. For a distance measuring interferometer wherein the element or elements serving the function of mirror 92 generates the equivalent of translations but does not produce the equivalent of tilts or yaws, the differential plane mirror interferometers of the first embodiment and variants thereof can be configured with $p_2$ either an even or odd integer, generally reducing the number of required passes by two, while retaining the features of the first embodiment and variants thereof. This reduction by a factor of two in the required number of passes can lead to a significant simplification of the optical system. For example, the differential plane mirror interferometers illustrated in FIGS. 1a–1e can be replaced with differential plane mirror interferometers having $p_1=2$ and $p_2=1$, otherwise retaining the features of the first embodiment and variants thereof, similar to the differential plane mirror interferometers and accompanying signal processing more fully illustrated and described with respect to the second embodiment and variants thereof in U.S. patent application Ser. No. 09/232,515, now U.S. Pat. No. 6,124,931, entitled APPARATUS AND METHODS FOR MEASURING INTRINSIC OPTICAL PROPERTIES OF A GAS that is copending herewith and the contents of which are incorporated herein by reference.

Figure 2A:
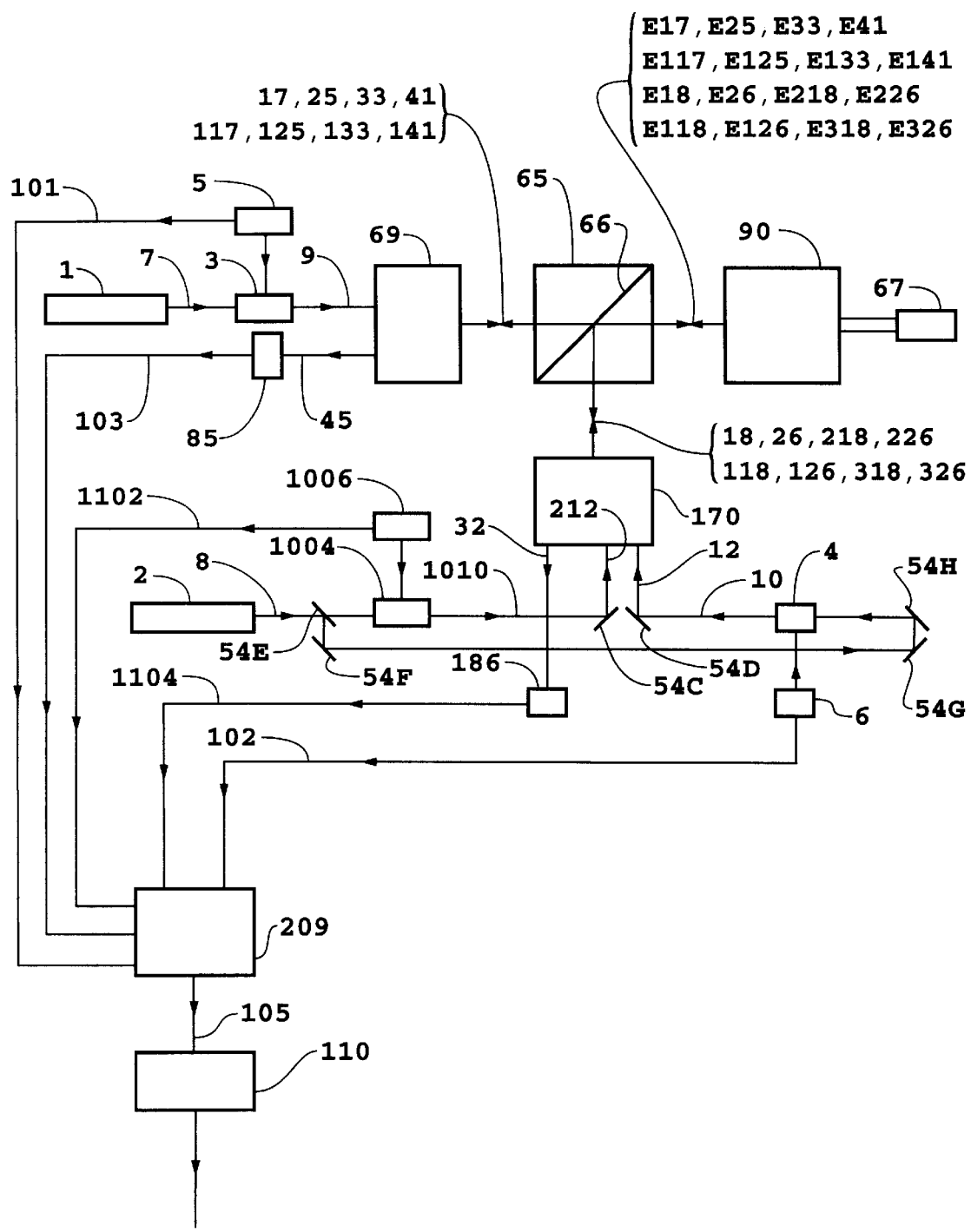
FIGS. 2a–2c taken together illustrate, in diagrammatic form, the presently preferred second embodiment of the present invention with FIG. 2a showing optical paths and the paths of electrical signals wherein elements of the second embodiment perform like operations as like numbered elements of the first embodiment.
Figure 2B:
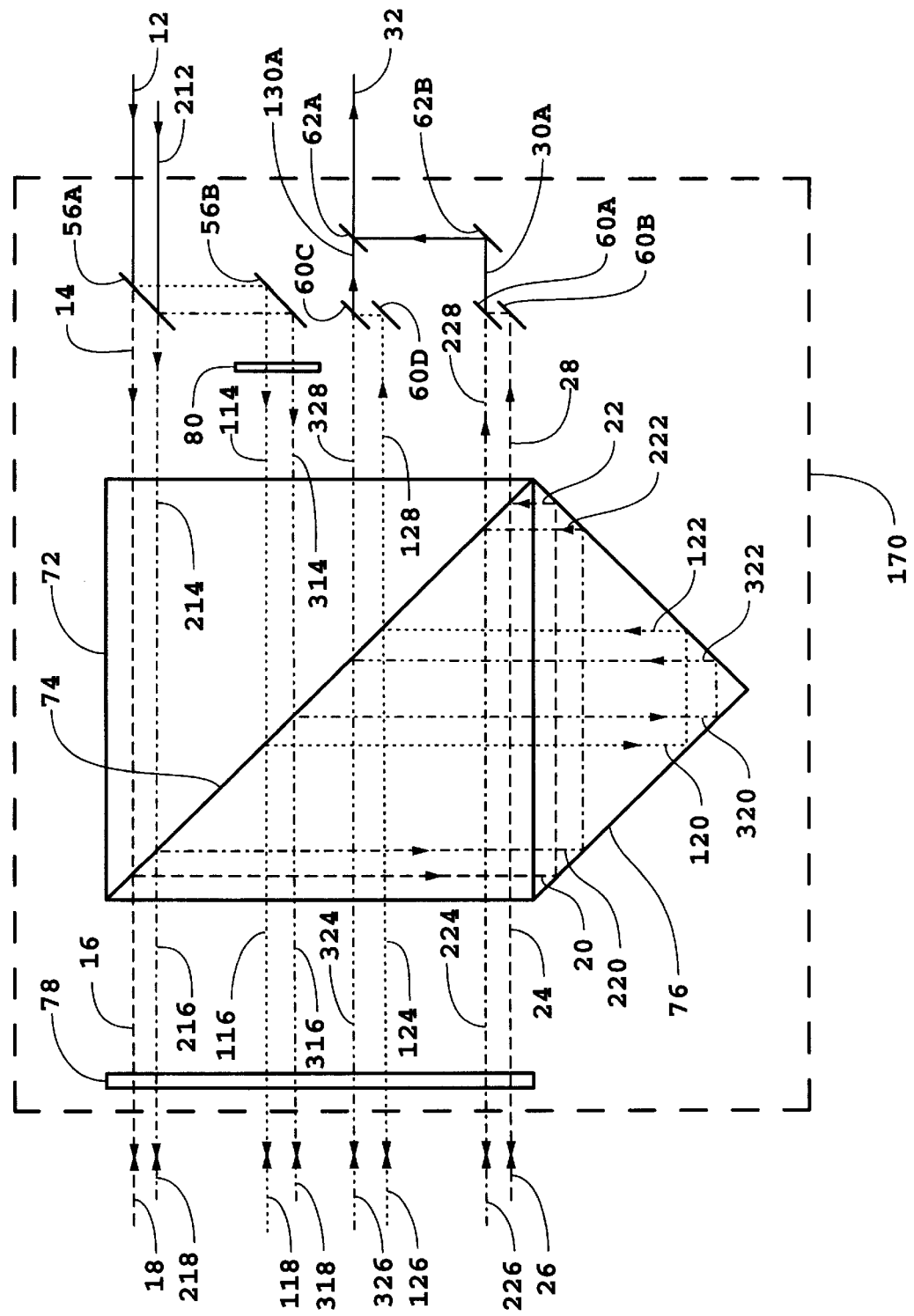
Figure 2C:
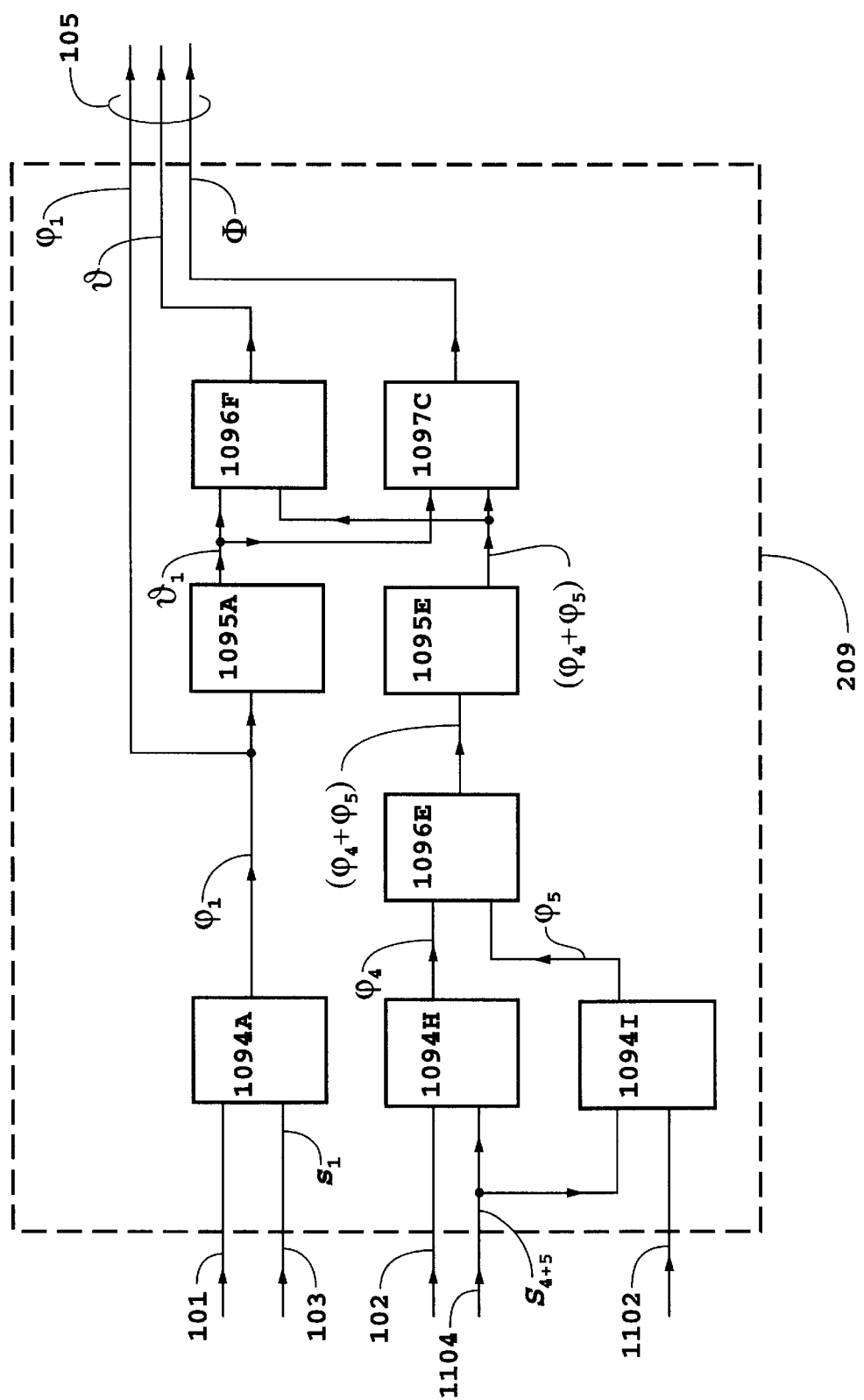

FIGS. 2a–2c depict in schematic form a second preferred embodiment of the present invention for measuring and monitoring the refractivity of a gas in a measurement path and/or the change in the optical path length of the measurement path due to the gas wherein either or both the refractivity of the gas and the physical length of the measurement path may be changing and where the stability of the adopted light sources is sufficient and the ratio of the wavelengths of the light beams generated by the adopted light sources is matched to a known ratio value with a relative precision sufficient to meet the required precision imposed on the output data by the final end use application. The difference between the second embodiment and the first embodiment is in the manner in which the heterodyne signals of the second embodiment corresponding to signals $s_2$ and $s_3$ of the first embodiment are generated and subsequently processed.

The description of the sources of light beams 8 and 9 and of light beams 8 and 9 for the second embodiment is the same as the description of the sources of light beams 8 and 9 and of light beams 8 and 9 given for the first embodiment. With reference to FIG. 2a, a first portion of light beam 8 is reflected by beam splitter 54E, preferably a nonpolarizing beam splitter, reflected by mirrors 54F, 54H, and 54G, and passes through modulator 4 becoming light beam 10. Modulator 4 is excited by driver 6, modulator 4 and driver 6 being the same as modulator 4 and driver 6 of the first embodiment. A second portion of light beam 8 is transmitted by beamsplitter 54E and passes through modulator 1004 becoming light beam 1010. Modulator 1004 is excited by driver 1006, modulator 1004 and driver 1006 being similar to modulator 4 and driver 6, respectively, of the second embodiment. The x polarized component of beam 10 has an oscillation frequency shifted an amount $f_2$ with respect to the y polarized component of beam 10. The x polarized component of beam 1010 has an oscillation frequency shifted an amount $f_3$ with respect to the y polarized component of beam 1010. The oscillation frequency $f_3$ is determined by the driver 1006. The frequencies $f_1$, $f_2$, and $f_3$ are all different one from the other. In addition, the positive directions of the frequency shifts of the x components of beams 9, 10, and 1010 are chosen to be the same without departing from the scope and spirit of the invention.

As illustrated in FIG. 2a, beam 9 is incident on differential plane mirror interferometer 69. Beam 10 is reflected by mirror 54D becoming beam 12 and beam 1010 is reflected by mirror 54C becoming beam 212. Beams 12 and 212 are incident on differential plane mirror interferometer group 170 comprising two differential plane mirror interferometers. Beams for which the first frequency component of beam 12 is the sole progenitor are indicated in FIG. 2b by dashed lines and beams for which the second frequency component of beam 12 is the sole progenitor are indicated in FIG. 2b by dotted lines. Beams for which the first frequency component of beam 212 is the sole progenitor are indicated in FIG. 2b by lines comprised of alternating dots and dashes and beams for which the second frequency component of beam 212 is the sole progenitor are indicated in FIG. 2b by lines comprised of alternating dot pairs and dashes. Differential plane mirror interferometer 69 and differential plane mirror interferometer group 170 with beam splitter 65 and external mirrors furnished by external mirror system 90 comprise interferometric means for introducing a phase shift $\phi_1$ between the x and y components of beam 9, a phase shift $\phi_4$ between the x and y components of beam 10, and a phase shift $\phi_5$ between the x and y components of beam 1010.

Differential plane mirror interferometer 69 is the same as differential plane mirror interferometer 69 of the first preferred embodiment. The paths of the optical beams in differential plane mirror interferometer group 170 are the same as the paths of the optical beams in differential plane mirror interferometer group 70 of the first preferred embodiment up through and including the generation of beams 28, 228, 128, and 328 as illustrated in FIG. 2b. In the second embodiment, beams 28, 228, 128, and 328 are combined optically to generate beam 32. Beam 32 is a mixed beam detected by detector 186, beam 32 being comprised of two components having the same polarizations but different frequencies.

Beam 32 is generated from beams 28, 228, 128, and 328 by the following steps. Beam 28 is reflected by mirror 60B, a portion subsequently reflected by mirror 60A, preferably a 50/50 nonpolarizing beam splitter, to form one part of beam 30A. A portion of beam 228 is transmitted by beam splitter 60A to form a second part of beam 30A, the first and second parts of beam 30A having the same polarization and the same frequencies. To the extent that the amplitudes of beams 28 and 228 are the same, to the extent that beam splitter 60A is a 50/50 beam splitter, and to the extent that the optical paths lengths for beams 28 and 228 are the same, substantially all of the beams 28 and 228 will be present in beam 30A because of constructive interference.

Beam 128 is reflected by mirror 60D, a portion subsequently reflected by mirror 60C, preferably a 50/50 nonpolarizing beam splitter, to form one part of beam 130A. A portion of beam 328 is transmitted by beam splitter 60C to form a second part of beam 130A, the first and second parts of beam 130A having the same polarizations and the same frequencies. To the extent that the amplitudes of beams 128 and 328 are the same, to the extent that beam splitter 60C is a 50/50 beam splitter, and to the extent that the optical paths lengths for beams 128 and 328 are the same, substantially all of the beams 128 and 328 will be present in beam 130A because of constructive interference. Beams 30A and 130A also have the same polarizations but different frequencies. Beam 130A and 30A contain information at wavelength $\lambda_2$ about optical path lengths through the measurement leg including measurement path 98 and about optical path lengths through the reference leg, respectively.

In a next step, beam 30A is reflected by mirror 62B and then a portion of beam 30A reflected by beam splitter 62A, preferably a nonpolarizing beam splitter, to become a first component of beam 32. A portion of beam 130A is transmitted by beam splitter 62A to become a second component of beam 32. Beam 32 is a mixed beam, the first and second components of beam 32 having the same polarizations but different frequencies.

The magnitude of phase shifts $\phi_1$, $\phi_4$, and $\phi_5$ are related to the difference $L_i$ between the round-trip physical length of path i of measurement path 98 and of reference paths shown in FIGS. 1d and 1e according to the formulae $$\varphi_1(t) = \sum_{i=1}^{i=p_1} \varphi_{1,i}(t_i) = \sum_{i=1}^{i=p_1} L_i(t_i) k_1 n_{1i} + \zeta_1, \qquad (46)$$

$$\varphi_4(t) = \sum_{i=1}^{i=p_2} \varphi_{4,i}(t_i) = \sum_{i=1}^{i=p_2} L_i(t_i) k_2 n_{2i} + \zeta_4,$$

$$\varphi_5(t) = \sum_{i=p_2+1}^{i=p_1} \varphi_{5,i}(t_i) = \sum_{i=p_2+1}^{i=p_1} L_i(t_i) k_2 n_{2i} + \zeta_5,$$

for the case of $p_1=2p_2$ where $n_{ji}$ are the refractive indices of gas in path i of measurement path 98 corresponding to wavenumber $k_j=(2\pi)/\lambda_j$. The nominal value for $L_i$ corresponds to twice the spatial separation of mirror surfaces 95 and 96 in external mirror system 90 (cf. FIGS. 1d and 1e). The phase offsets $\zeta_l$ comprise all contributions to the phase shifts $\phi_l$ that are not related to the measurement path 98 or reference paths. To those skilled in the art, the generalization to case when $p_1 \neq 2p_2$ is a straight forward procedure. In FIGS. 2a–2b, differential plane mirror interferometer 69, differential plane mirror interferometer group 70, beam splitter 65, and external mirror system 90 are configured so that $p_1=4$ and $p_2=2$, respectively, so as to illustrate in the simplest manner the function of the apparatus of the second preferred embodiment of the present invention.

In a next step as shown in FIG. 2a, beams 45 and 32 impinge upon photodetectors 85 and 186, respectively, resulting in electrical interference signal, heterodyne signals $s_1$ and $S_{4+5}=s_4+s_5$, respectively, preferably by photoelectric detection. There are heterodyne signals other than $s_4$ and $s_5$ created by beam 32 impinging upon photodetector 186. However, these other heterodyne signals are not detected in subsequent signal processing and thus not included in the description of the second embodiment without departing from the scope and spirit of the present invention. The signal $s_1$ corresponds to the wavelength signal $\lambda_1$ and the signal $S_{4+5}$ corresponds to the wavelength $\lambda_2$. The signals $s_l$ have the form $$s_l = A_l \cos[\alpha_l(t)], \, l=1, 4, \text{ and } 5, \qquad (47)$$

where the time-dependent arguments $\alpha_l(t)$ are given by $$\alpha_1(t)=2\pi f_1 t+\phi_1,$$

$$\alpha_4(t)=2\pi f_2 t+\phi_4,$$

$$\alpha_5(t)=2\pi f_3 t+\phi_5. \qquad (48)$$

Heterodyne signals $s_1$ and $S_{4+5}$ are transmitted as electronic signals 103 and 1104, respectively, to electronic processor 209 for analysis in either digital or analog format, preferably in digital format.

A preferred method for electronically processing the heterodyne signals $s_1$, $s_4$, and $s_5$ is presented herewithin for the case when $l_1$ and/or $l_2$ are not low order integers. For the case when $l_1$ and $l_2$ are both low order integers and the ratio of the wavelengths matched to the ratio $(l_1/l_2)$ with a relative precision sufficient to meet the required precision imposed on the output data by the end use application, the preferred procedure for electronically processing the heterodyne signals $s_1$, $s_4$, and $s_5$ is the same as the one subsequently set down for the second variant of the second preferred embodiment.

Referring now to FIG. 2c, electronic processor 209 preferably is comprised of alphameric numbered elements wherein the numeric component of the alphameric numbers indicate the function of an element, the same numeric component/function association as described for the electronic processing elements of the first embodiment depicted in FIG. 1f. The description of the steps in processing of heterodyne signals $s_1$, $s_4$, and $s_5$ by electronic processor 209 is the same as corresponding portions, according to the numeric component of the alphameric numbers of elements, of the descriptions given for steps in the processing of the heterodyne signals $s_1$, $s_2$, and $s_3$ of the first embodiment by electronic processor 109.

The processing of the heterodyne signals $s_1$, $s_4$, and $s_5$ by electronic processor 209 creates three phases $\phi_1$, $\phi_4$, and $\phi_5$. Formally, the properties of phases $\phi_1$, $\phi_4$, and $\phi_5$ have the same properties as $\phi_1$, $\phi_2$, and $\phi_3$, respectively, created by electronic processor 109 of the first embodiment. The subsequent processing of $\phi_4$ and $\phi_5$ by electronic processor 209 creates two phases $\vartheta$ and $\Phi$ wherein the properties of phases $\vartheta$ and $\Phi$ are formally the same as properties of $\vartheta$ and $\Phi$, respectively, created by electronic processor 109 of the first embodiment.

In the second embodiment, the frequencies of the three drivers 5, 6, and 1006 can be chosen such that $$f_1=(f_2+f_3)/2. \qquad (49)$$

This feature of the second embodiment in conjunction with another feature of the second embodiment, the detection of the optical beams creating heterodyne signals $s_4$ and $s_5$ by a single detector, can substantially eliminate the first order effects of differences in group delays which may be present in the first embodiment resulting from $f_1 \neq f_2$. The remaining description of the second embodiment is the same as corresponding portions of the description given for the first embodiment.

A first variant of the second preferred embodiment is disclosed wherein the description of the apparatus of the first variant of the second embodiment is the same as that given for the apparatus of the second embodiment except with regard to the detection of beams 45 and 32 of the second embodiment shown in FIG. 2a and with $|f_2-f_1| \neq |f_3-f_1|$. In the first variant of the second embodiment, a first portion of beam 45 is detected by detector 85 creating signal proportional $s_1$, as $s_1$ where a is a constant, and beam 32 and a second portion of beam 45 are detected by a single detector (not shown in the figures) creating signal $S_{b1+4+5}=bs_1+s_4+s_5$ where b is a constant. The description of $S_{b1+4+5}$ with regard to omitted heterodyne components is the same as the corresponding portion of the description given for $S_{4+5}$ of the second embodiment with regard of omitted heterodyne terms. Heterodyne signals $as_1$ and $S_{b1+4+5}$ are transmitted as electronic signals 103 and 2104, respectively, in either digital or analog format, preferably in digital format, to electronic processor 209A shown in diagrammatic form in FIG. 2d for analysis.

Figure 2D:
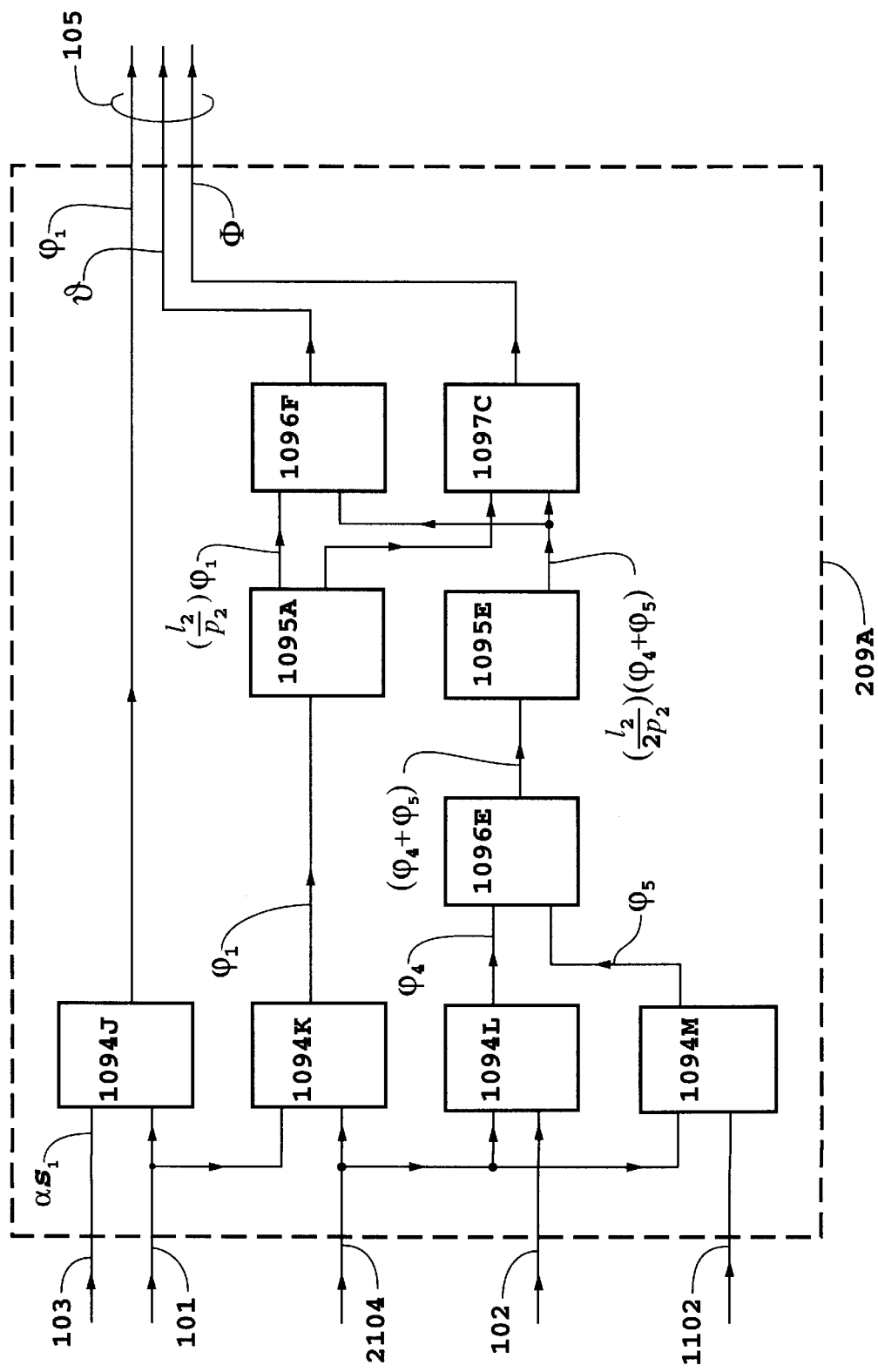
FIG. 2d is a drawing showing a block diagram of the processing electronics 209A for the first variant of the second embodiment.

Referring now to FIG. 2d, electronic processor 209A preferably is comprised of alphameric numbered elements wherein the numeric component of the alphameric numbers indicate the function of an element, the same numeric component/function association as described for the electronic processing elements of the first embodiment depicted in FIG. 1f and the second embodiment depicted in FIG. 2c. The description of the steps in processing of the heterodyne signals $bs_1$, $s_4$, and $s_5$ comprising $S_{b1+4+5}$ by electronic processor 209A for phases $\vartheta$ and $\Phi$ is the same as corresponding portions, according to the numeric component of the alphameric numbers of elements, of the description of steps in the processing of the heterodyne signals $s_1$, $s_4$, and $s_5$ of the second embodiment by electronic processor 209. The description of the steps in processing of the heterodyne signal $as_1$ by electronic processor 209A for phase $\phi_1$ is the same as corresponding portions, according to the numeric component of the alphameric numbers of elements, of the description of steps in the processing of the heterodyne signal $s_1$ of the second embodiment by electronic processor 209.

The phases $\phi_1$, $\vartheta$, and $\Phi$ created by electronic processor 209A formally have the same properties as $\phi_1$, $\vartheta$, and $\Phi$, respectively, created by electronic processor 209 of the second embodiment.

The feature of the first variant of the second embodiment which can be a significant feature is the detection the optical beams creating heterodyne signals $bs_1$, $s_4$, and $s_5$ by a single detector. It will be apparent to those skilled in the art that the single detector feature of the first variant of the second embodiment can be important in reducing or eliminating the effects of differences in certain group delays possible in the second embodiment. The remaining description of the first variant of the second embodiment is the same as corresponding portions of the description given for the second embodiment.

Figure 2E:
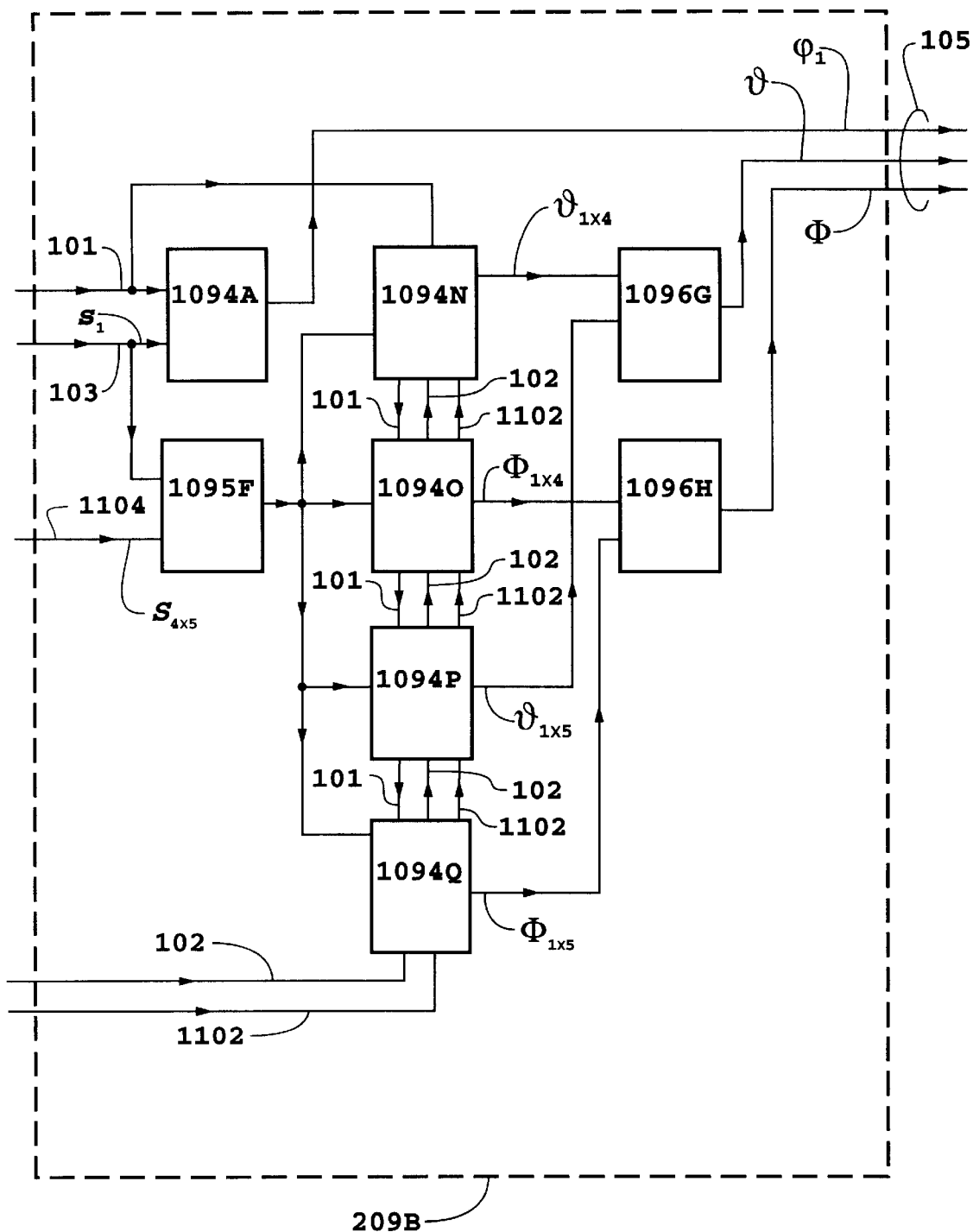
FIG. 2e is a drawing showing a block diagram of the processing electronics 209B for the second variant of the second embodiment.

Reference is now made to FIGS. 2a, 2b, and 2e which taken together depict in diagrammatic form a second variant of the second preferred embodiment of the present invention for measuring and monitoring the refractivity of a gas in a measurement path and/or the change in the optical path length of the measurement path due to the gas wherein either or both the refractive index of the gas and the physical length of the measurement path may be changing and where the stability of the adopted light sources is sufficient and the wavelengths of the light beams generated by the adopted light sources are harmonically related to a relative precision sufficient to meet the required precision imposed on the output data by the final end use application. The condition wherein the wavelengths are approximately harmonically related corresponds to the special case of the second embodiment in which the ratio $(l_1/l_2)$ is expressible as the ratio of low order non-zero integers $(p_1/p_2)$, the same as expressed by Eq. (26), which corresponds to the wavelengths $\lambda_1$ and $\lambda_2$ being approximately harmonically related.

The description of the sources of light beams 8 and 9 and of light beams 9, 10, and 1010 for the second variant of the second embodiment is the same as that for description of the sources of light beams 8 and 9 and of light beams 9, 10, and 1010 given for the second embodiment with an additional requirement, the additional requirement that the wavelengths be harmonically related to a relative precision sufficient to meet the required recision imposed on the output data by the final end use application. The description of the apparatus for the second variant of the second embodiment depicted in FIGS. 2a and 2b is the same as corresponding portions of the description given for the second embodiment for the case where $p_1=4$ and $p_2=2$.

Referring now to FIG. 2e, electronic processor 209B preferably is comprised of alphameric numbered elements wherein the numeric component of the alphameric numbers indicate the function of an element, the same numeric component/function association as described for the electronic processing elements of the first embodiment depicted in FIG. 1f and the second embodiment depicted in FIG. 2c. The description of the steps in processing of heterodyne signals $s_4$ and $s_5$ comprising $S_{4+5}$ and $s_1$ by electronic processor 209B for phases $\tilde{\vartheta}$ and $\Phi$ is the same as corresponding portions, according to the numeric component of the alphameric numbers of elements, of the descriptions of steps in the processing of the heterodyne signals $s_1$, $s_2$, and $s_3$ of the second variant of the first embodiment by electronic processor 109A. The description of the steps in processing of the heterodyne signal $s_1$ by electronic processor 209A for phase $\phi_1$ is the same as corresponding portions, according to the numeric component of the alphameric numbers of elements, of the description of steps in the processing of the heterodyne signals $s_1$ of the second variant of the first embodiment by electronic processor 109A for phase $\phi_1$.

The principal advantage of the second variant of the second embodiment in relation to the second embodiment is substantially the same as the principal advantage of the second variant of the first embodiment in relation to the first embodiment with the addition of the advantage of the second embodiment relative to the first embodiment regarding the use of a single detector to detect $s_4$ and $s_5$. The remaining description of the second variant of the second embodiment is the same as corresponding portions of the description given for the second embodiment.

Figure 2F:
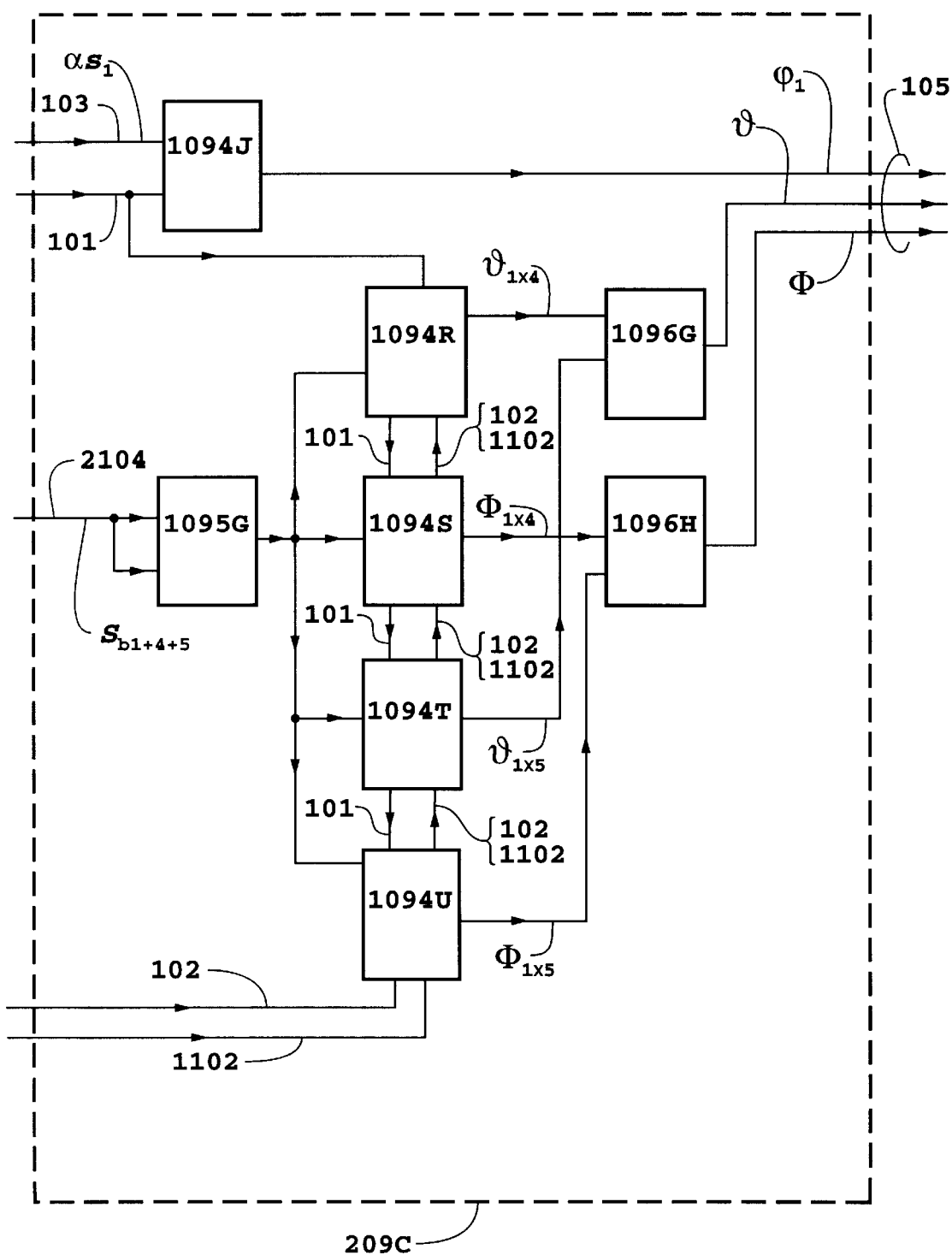
FIG. 2f is a drawing showing a block diagram of the processing electronics 209C for the third variant of the second embodiment.

Reference is now made to FIGS. 2a, 2b, and 2f which taken together depict in diagrammatic form a third variant of the second preferred embodiment of the present invention for measuring and monitoring the refractivity of a gas in a measurement path and/or the change in the optical path length of the measurement path due to the gas wherein either or both the refractive index of the gas and the physical length of the measurement path may be changing and where the stability of the adopted light sources is sufficient and the wavelengths of the light beams generated by the adopted light sources are harmonically related to a relative precision sufficient to meet the required precision imposed on the output data by the final end use application. The condition wherein the wavelengths are approximately harmonically related corresponds to the special case of the second embodiment in which the ratio $(l_1/l_2)$ is expressible as the ratio of low order non-zero integers $(p_1/p_2)$, the same as expressed by Eq. (26), which corresponds to the wavelengths $\lambda_1$ and $\lambda_2$ being approximately harmonically related.

The description of the sources of light beams 8 and 9 and of light beams 9, 10, and 1010 for the third variant of the second embodiment is the same as that for description of the sources of light beams 8 and 9 and of light beams 9, 10, and 1010 given for the second variant of the second embodiment. The description of the apparatus of the third variant of the second embodiment other than the description of the sources of light beams 8 and 9 is the same as that given for the corresponding apparatus of the first variant of the second embodiment. Heterodyne signals $as_1$ and $S_{b1+4+5}$ created by the detectors of the third variant of the second embodiment are transmitted as electronic signals 103 and 2104, respectively, in either digital or analog format, preferably in digital format, to electronic processor 209C shown in diagrammatic form in FIG. 2f for analysis.

Referring now to FIG. 2f, electronic processor 209C preferably is comprised of alphameric numbered elements wherein the numeric component of the alphameric numbers indicate the function of an element, the same numeric component/function association as described for the electronic processing elements of the first embodiment depicted in FIG. 1f and the second embodiment depicted in FIG. 2c. The description of the steps in processing of the heterodyne signals $bs_1$, $s_4$, and $s_5$ comprising $S_{b1+4+5}$ by electronic processor 209C for phases $\tilde{\vartheta}$ and $\Phi$ is the same as corresponding portions, according to the numeric component of the alphameric numbers of elements, of the description of steps in the processing of the heterodyne signals $s_1$, $s_4$, and $s_5$ of the second embodiment by electronic processor 209 and of the second variant of the second embodiment by electronic processor 209B. The description of the steps in processing of the heterodyne signal $as_1$ by electronic processor 209C for phase $\phi_1$ is he same as corresponding portions, according to the numeric component of the alphameric numbers of elements, of the description of steps in the processing of the heterodyne signal $s_1$ of the second embodiment by electronic processor 209.

The principal advantage of the third variant of the second embodiment in relation to the second embodiment is substantially the same as the principal advantage of the second variant of the first embodiment in relation to the first embodiment with the addition of the advantage of the first variant of the second embodiment relative to the first embodiment regarding the use of a single detector to detect $bs_1$, $s_4$, and $s_5$ The remaining description of the third variant of the second embodiment is the same as corresponding portions of the descriptions given for the second embodiment and the second variant of the second embodiment.

Reference is now made to FIGS. 3a–3g which depict in diagrammatic form the third preferred embodiment of the present invention for measuring and monitoring the refractivity of a gas in a measurement path and/or the change in the optical path length of the measurement path due to the gas wherein either or both the refractivity of the gas and the physical length of the measurement path may be changing. The primary difference between the third embodiment and the first embodiment and variants thereof lies in the design and utilization of differential plane mirror interferometers. The description of the sources of light beams 9 and 10 and of light beams 9 and 10 for the third embodiment is the same as the description of the sources of light beams 9 and 10 and of light beams 9 and 10 given for the first preferred embodiment of the present invention.

Figure 3A:
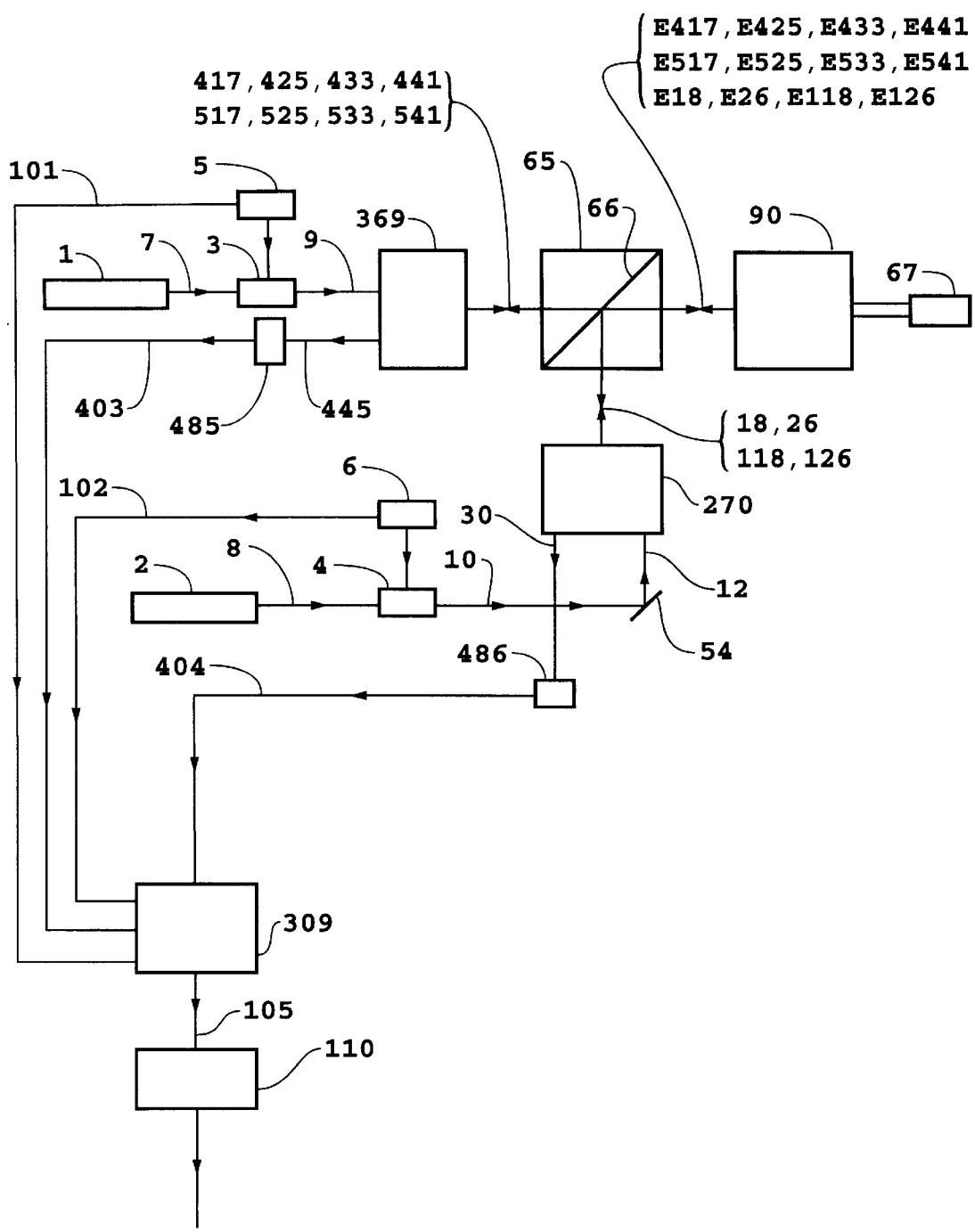
FIGS. 3a–3g taken together illustrate, in diagrammatic form, the presently preferred third embodiment of the present invention with FIG. 3a showing optical paths and the paths of electrical signals wherein elements of the third embodiment perform like operations as like numbered elements of the first embodiment.
Figure 3B:
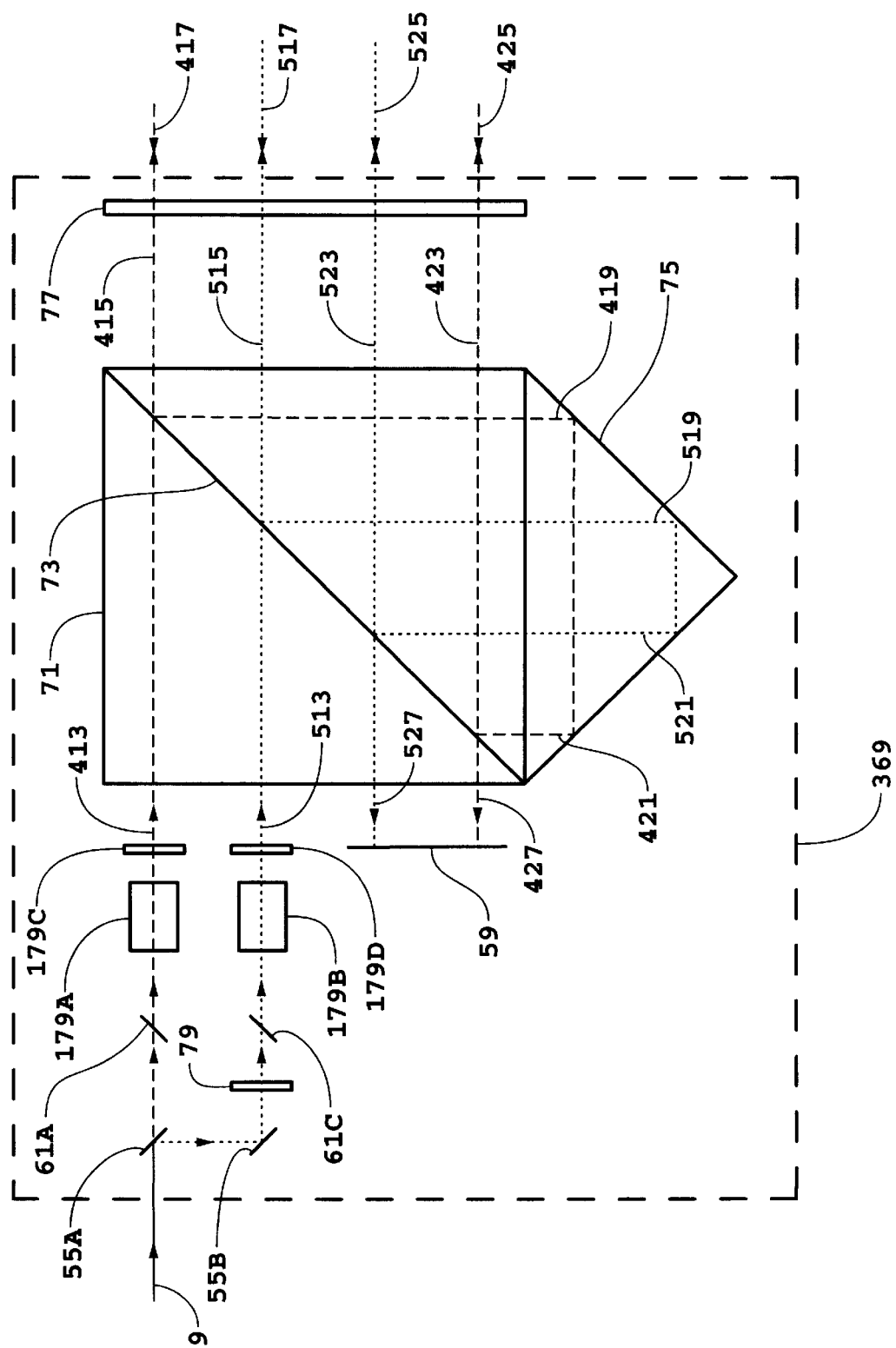
Figure 3C:
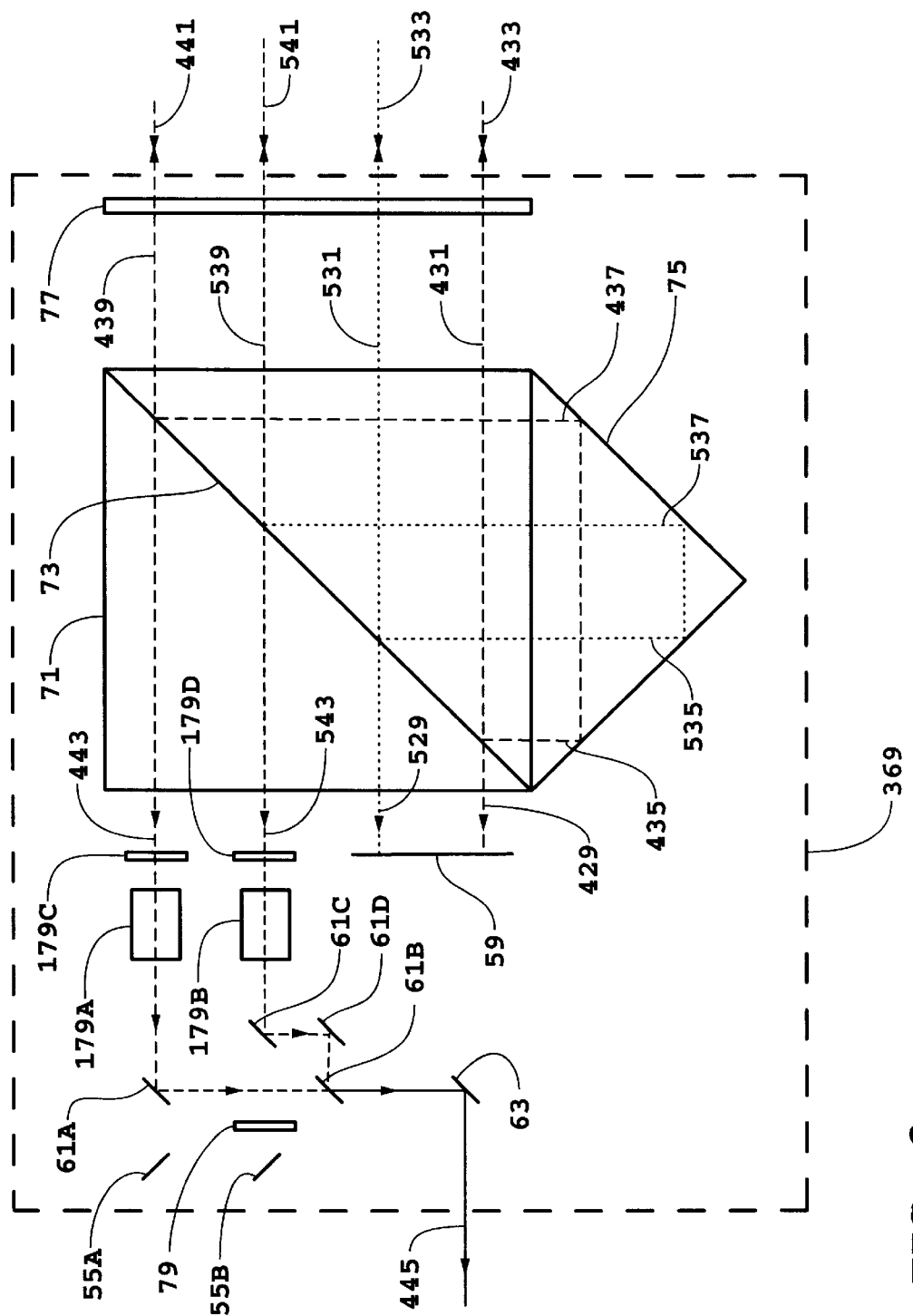
Figure 3D:
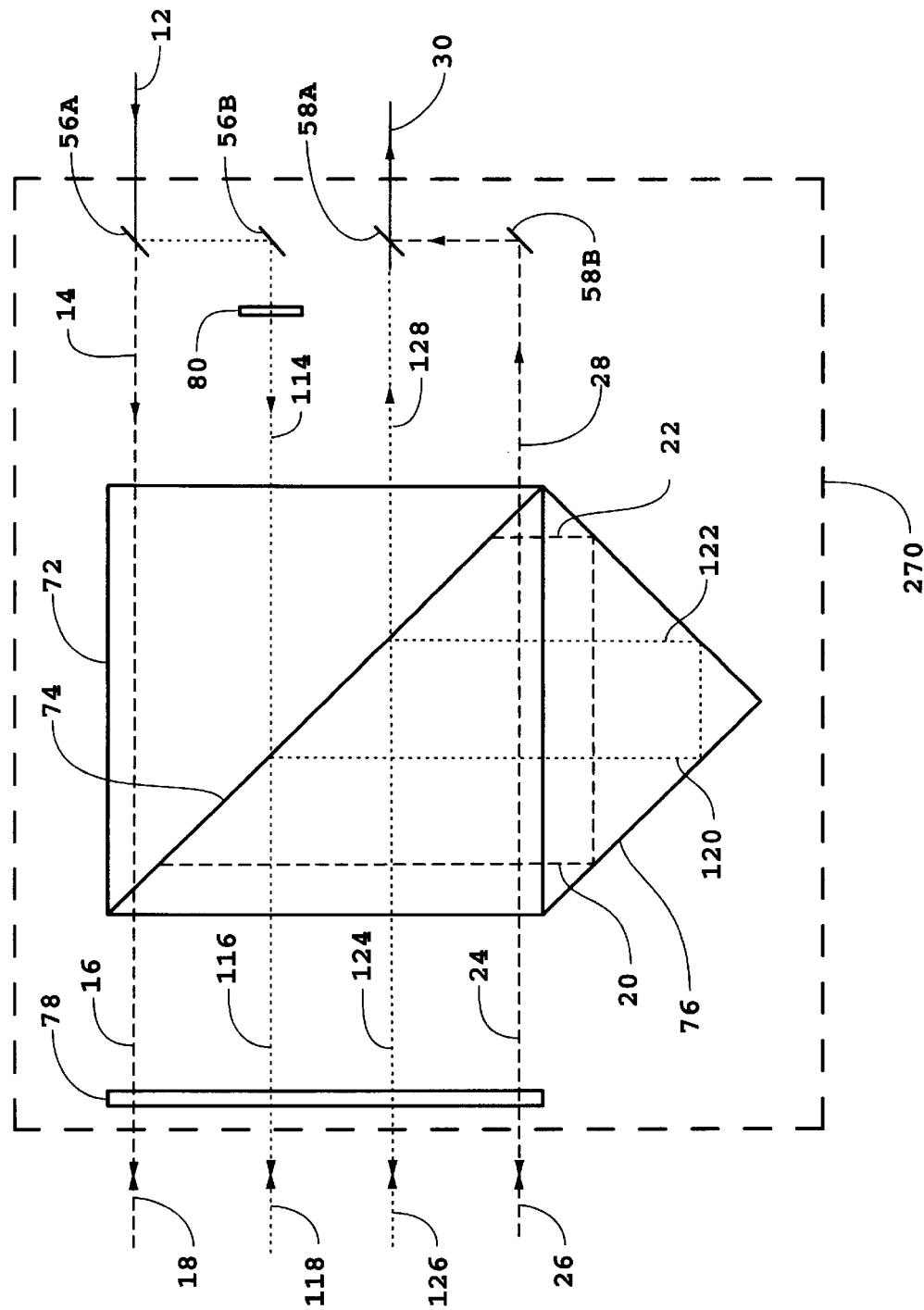

As illustrated in FIG. 3a, beam 10 is reflected by mirror 54 becoming beam 12. Beam 9 is incident on differential plane mirror interferometer 369 and beam 12 is incident on differential plane mirror interferometer 270. Beams for which the first frequency component of beam 9 is the sole progenitor are indicated in FIGS. 3b and 3c by dashed lines and beams for which the second frequency component of beam 9 is the sole progenitor are indicated in FIGS. 3b and 3c by dotted lines. Differential plane mirror interferometers 369 and 270, beam splitter 65, and external mirrors furnished by external mirror system 90 comprise interferometric means for introducing a phase shift $\phi_6$ between the x and y components of beam 9 and a phase shift $\phi_7$ between the x and y components of beam 12.

Figure 3E:
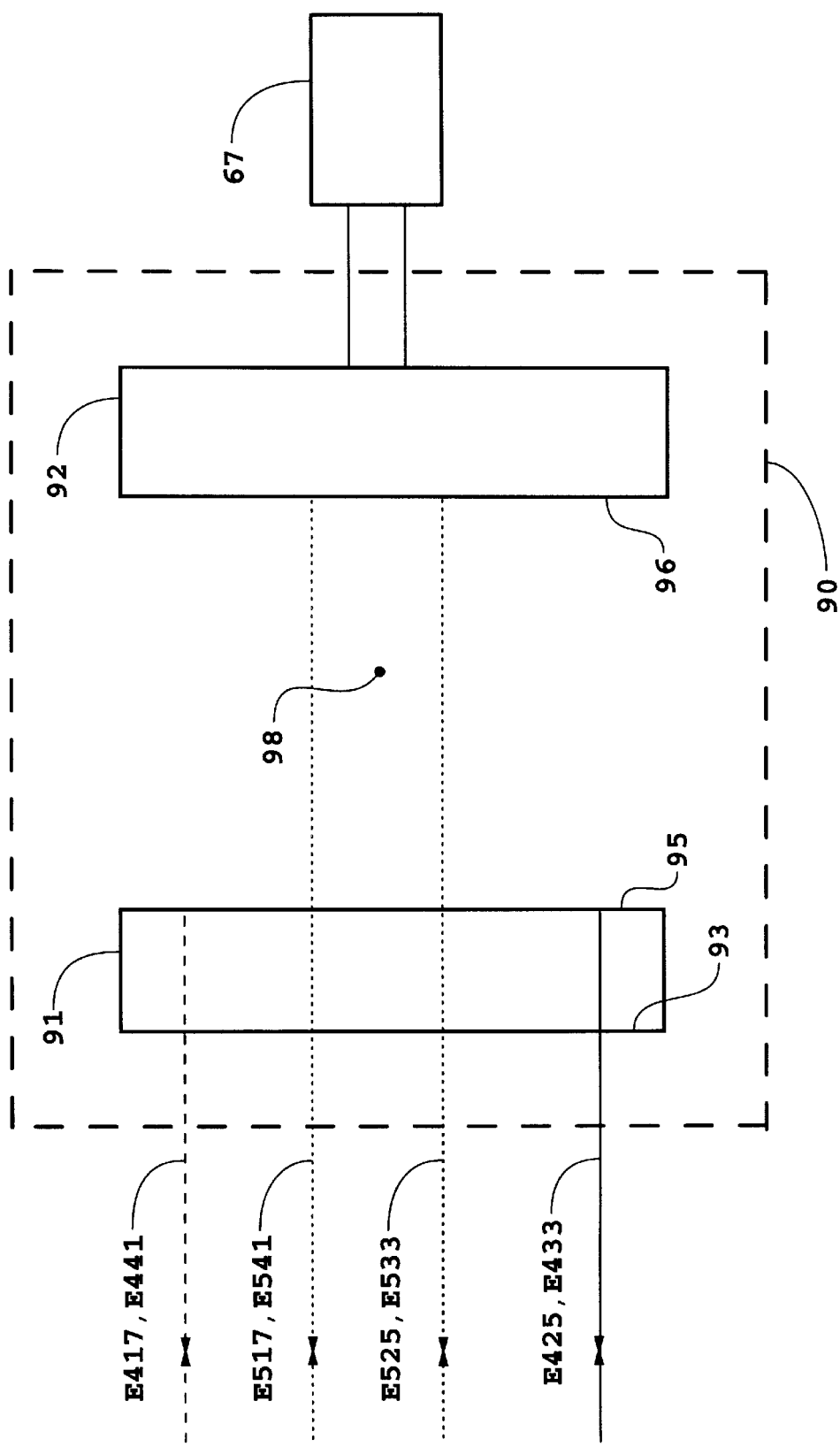
Figure 3F:
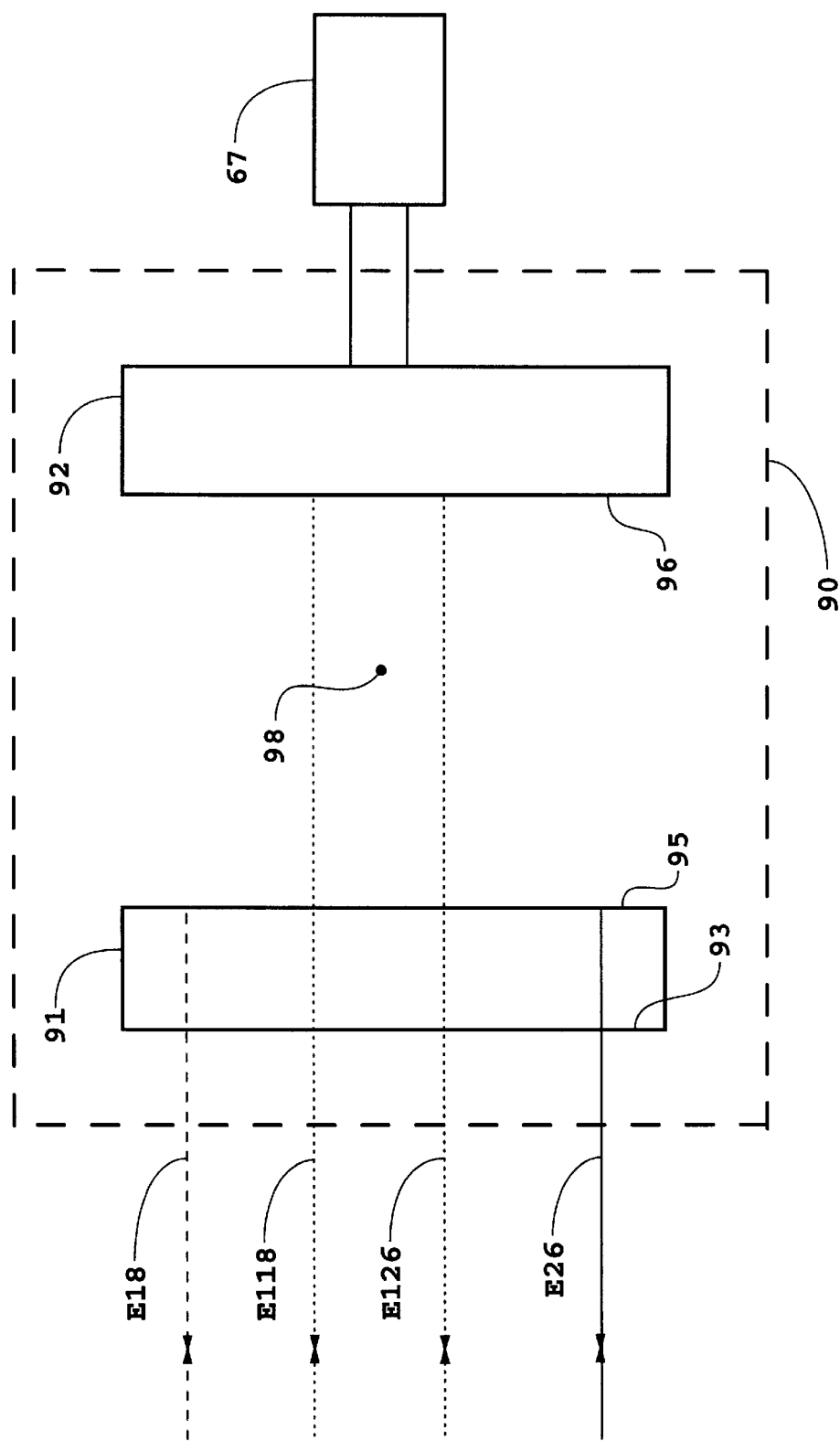

Differential plane mirror interferometer 369 has eight exit/return beams, four exit/return beams 417, 425, 517, and 525 as shown in FIG. 3b and four exit/return beams 433, 441, 533, and 541 as shown in FIG. 3c. Beams 417, 425, 433, and 441 originating from one frequency component of beam 9 comprise a reference leg and beams 517, 525, 533, and 541 originating from a second frequency component of beam 9 comprise a measurement leg. Beams 417, 425, 433, 441, 517, 525, 533, and 541 are incident on beam splitter 65 and transmitted by coating 66, preferably a dichroic coating, as beams E417, E425, E433, E441, E517, E525, E533, and E541, respectively. Beams E417, E425, E433, E441, E517, E525, E533, and E541 are incident on external mirror system 90, as illustrated in FIGS. 3e and 3f, which results in beams 443 and 543 (FIG. 3). Beam 543 and 443 contain information at wavelength $\lambda_1$ about optical path lengths through the gas in measurement path 98 wherein the effects of the refractivity of the gas is to be determined and about optical path lengths through the reference leg, respectively.

Differential plane mirror interferometer 270 has four exit/return beams 18, 26, 118, and 126 as shown in FIG. 3a. Beams 18 and 26 originating from one frequency component of beam 12 comprise a reference leg and beams 118 and 126 originating from a second frequency component of beam 12 comprise a measurement leg. Beams 18, 26, 118, and 126 are incident on beam splitter 65 and reflected by dichroic coating 66 as beams E18, E26, E118, and E126, respectively. Beams E18, E26, E118, and E126 are reflected back on themselves by external mirror system 90, as illustrated in FIG. 3f, reflected by coating 66 of beam splitter 65, and are incident on differential plane mirror interferometer 270 resulting in beams 28 and 128 (FIG. 3d) Beams 128 and 28 contain information at wavelength $\lambda_2$ about optical path lengths through the measurement leg including the gas of measurement path 98 wherein the effects of the refractivity of the gas is to be determined and about optical path lengths through the reference leg, respectively.

The magnitude of phase shifts $\phi_6$ and $\phi_7$ are related to the difference $L_i$ between the round-trip physical length of path i of measurement path 98 and of reference paths shown in FIGS. 3a–3f according to the formulae $$\varphi_6 = \sum_{i=1}^{i=p_1} \varphi_{6,i} = \sum_{i=1}^{i=p_1} L_i k_1 n_{1i} + \zeta_6, \qquad (50)$$

$$\varphi_7 = \sum_{i=1}^{i=p_2} \varphi_{7,i} = \sum_{i=1}^{i=p_2} L_i k_2 n_{2i} + \zeta_7.$$

The illustration in FIGS. 3b–3f is for $p_1=4$ and $p_2=2$ so as to illustrate in the simplest manner the function of the invention in the second preferred embodiment.

Beam 443, as illustrated in FIG. 3c, is transmitted by half-wave phase retardation plate 179C and Faraday rotator 179A, reflected by beam splitter 61A, partially transmitted by beam splitter 61B, and then reflected by mirror 63 to become a first component of phase-shifted beam 445. Half-wave phase retardation plate 179C and Faraday rotator 179A each rotate the polarization of beam 443 by 45° so that the first component of phase-shifted beam 445 is orthogonally polarized to the polarization of beam 443. Beam splitter 61A is preferably a polarizing beam splitter and beam splitter 61B is preferably a nonpolarizing beam splitter. Beam 543 is transmitted by half-wave phase retardation plate 179D and Faraday rotator 179B, reflected by beam splitter 61C, reflected by mirror 61D, partially reflected by beam splitter 61B, and then reflected by mirror 63 to become a second component of phase-shifted beam 445. Half-wave phase retardation plate 179D and Faraday rotator 179B each rotate the polarization of beam 543 by 45° so that the second component of phase-shifted beam 445 is orthogonally polarized to the polarization of beam 543. Beam splitter 61C is preferably a polarizing beam splitter. Phase-shifted beam 445 is a mixed beam, the first and second components of phase-shifted beam 445 having the same polarizations but different frequencies.

Beam 28 is reflected by mirror 58B and then a portion reflected by beam splitter 58A, preferably a nonpolarizing beam splitter, to become a first component of phase-shifted beam 30. A portion of beam 128 is transmitted by beam splitter 58A to become a second component of phase-shifted beam 30. Phase-shifted beam 30 is a mixed beam, the first and second components of phase-shifted beam 30 having the same polarizations but different frequencies.

In a next step as shown in FIG. 3a, phase-shifted beams 445 and 30 impinge upon photodetectors 485 and 486, respectively, resulting in two electrical interference signals, heterodyne signals $s_6$ and $s_7$, respectively, preferably by photoelectric detection. The signal $s_6$ corresponds to wavelength $\lambda_1$ and signal $s_7$ corresponds to the wavelength $\lambda_2$. The signals $s_l$ have the form expressed by Eq. (3) with l=6 and 7. The time-dependent arguments $\alpha_l(t)$ given by $$\alpha_6(t)=2\pi f_1 t+\phi_6,$$

$$\alpha_7(t)=2\pi f_2 t+\phi_7. \qquad (51)$$

Heterodyne signals $s_6$ and $s_7$, are transmitted to electronic processor 309 for analysis as electronic signals 403 and 404, respectively, in either digital or analog format, preferably in digital format.

Figure 3G:
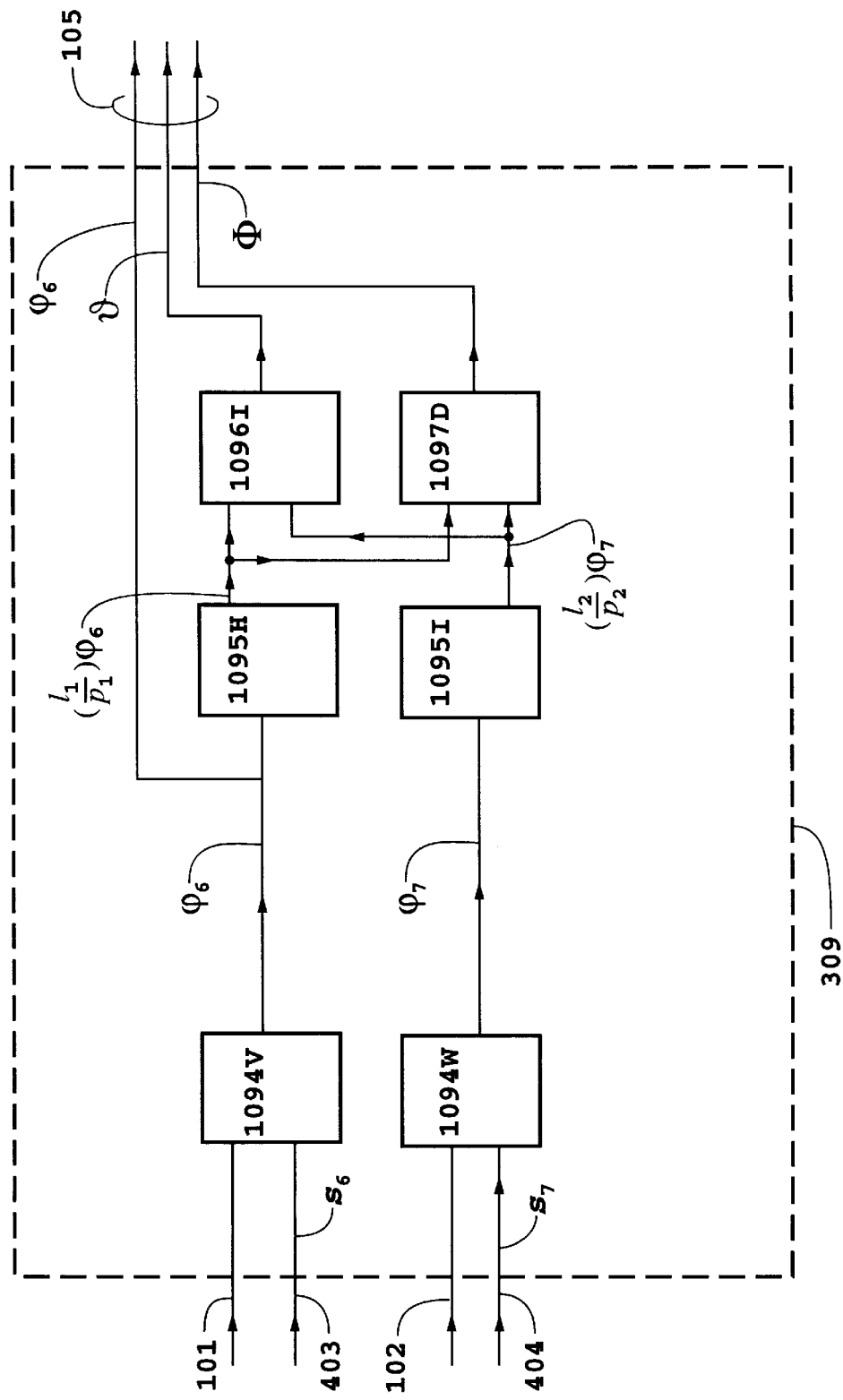

Referring to FIG. 3g, electronic processor 309 comprises electronic processors 1094V and 1094W to determine phases $\phi_6$ and $\phi_7$ from signals $s_6$ and $s_7$, respectively, in a manner the same as described for the determination of phases $\phi_1$, $\phi_2$, and $\phi_3$ from signals $s_1$, $s_2$, and $s_3$, respectively, of the first embodiment. Next, phases $\phi_6$ and $\phi_7$ are multiplied by $(l_1/p_1)$ and $(l_2/p_2)$, respectively, in electronic processors 1095H and 1095I, respectively, preferably by digital processing, resulting in phases and $(l_2/p_2)\phi_7$, respectively. The phases $(l_1/p_1)\phi_6$ and $(l_2/p_2)\phi_7$ are next added together in electronic processor 1096I and subtracted one from the other in electronic processor 1097D, preferably by digital processes, to create phases $\vartheta$ and $\Phi$, respectively.

Phases $\vartheta$ and $\Phi$ of the third embodiment are formally the same as corresponding phases $\vartheta$ and $\Phi$ of the first embodiment. Subsequent determinations in the third embodiment of the dispersion of a gas in the measuring path and/or the effects of the gas in the measuring path is the same as described for corresponding determinations in the first embodiment with $\phi_6$ corresponding to $\phi_1$.

The operation of differential plane mirror interferometer 369 is the same as the operation described for differential plane mirror interferometer 69 except for the means used to separate the two frequency components of input beam 9 and the means used to create the mixed output beam 445. Referring to FIG. 3b, a portion of beam 9 is reflected by beam splitter 55A, preferably a polarizing beam splitter, reflected by mirror 55B, transmitted by half-wave phase-retardation plate 79, transmitted by beam splitter 61C, preferably a polarizing beam splitter, transmitted by Faraday rotator 179B, and subsequently transmitted by half-wave phase-retardation plate 179D to become beam 513. The Faraday rotator 179B and the half-wave phase-retardation plate 179D rotate the plane of polarization of transmitted beams by ±45° and ∓45°, respectively, producing no net rotation of the plane of polarization of transmitted beams. A portion of beam 9 is transmitted by beam splitter 55A, transmitted by beam splitter 61A, preferably a polarizing beam splitter, transmitted by Faraday rotator 179A, and subsequently transmitted by half-wave phase-retardation plate 179C to become beam 413. The Faraday rotator 179A and the half-wave phase-retardation plate 179C rotate the plane of polarization of transmitted beams by ±45° and ∓45°, respectively, producing no net rotation of the plane of polarization of transmitted beams. Half-wave phase-retardation plate 79 rotates the plane of polarization of transmitted beam by 90° so that beams 413 and 513 have the same polarizations but have different frequencies. The purpose of the Faraday rotators 179A and 179B and the half-wave phase-retardation plates 179C and 179D is to have substantially no effect on the properties of beams 413 and 513 but to rotate the polarizations of beams 443 and 543, illustrated in FIG. 3c, by 90° as previously described so as to achieve an efficient spatial separation of beams 443 and 543 from the path of beam 9.

The remaining description of the third embodiment is the same as the description given for corresponding portions of the first embodiment of the present invention.

Reference is again made to FIGS. 3a–3f with electronic processor 309 being replaced by electronic processor 309A (electronic processor 309A is not depicted in a figure). These figures taken together with the noted alteration depict in diagrammatic form a first variant of the third preferred embodiment of the present invention for measuring and monitoring the refractivity of a gas in a measurement path and/or the change in the optical path length of the measurement path due to the gas wherein either or both the refractive index of the gas and the physical length of the measurement path may be changing and where the stability of the adopted light sources is sufficient and the wavelengths of the light beams generated by the adopted light sources are harmonically related to a relative precision sufficient to meet the required precision imposed on the output data by the final end use application. The condition wherein the wavelengths are approximately harmonically related corresponds to the special case of the second embodiment in which the ratio $(l_1/l_2)$ is expressible as the ratio of low order non-zero integers $(p_1/p_2)$, the same as expressed by Eq. [(26)], which corresponds to the wavelengths $\lambda_1$ and $\lambda_2$ being approximately harmonically related.

The description of the sources of light beams 8 and 9 and of light beams 9, 10, and 1010 for the first variant of the third embodiment is the same as that for description of the sources of light beams 8 and 9 and of light beams 9, 10, and 1010 given for the third embodiment with an additional requirement, the additional requirement that the wavelengths be harmonically related to a relative precision sufficient to meet the required precision imposed on the output data by the final end use application. The description of the apparatus for the first variant of the third embodiment depicted in FIGS. 3a–3f is the same as corresponding portions of the description given for the third embodiment except with respect to electronic processor 309A.

Electronic processing means 309A (not shown in a figure) preferably comprises means for electronically multiplying together the two heterodyne signals $s_6$ and $s_7$, (such as electronic processor 1095C in FIG. 1g for multiplying together signals $s_1$ and $s_2$ to create superheterodyne signal $S_{1\times 2}$) to create a superheterodyne signal $S_{6\times 7}$ having the mathematical form $$S_{6\times 7}=S_6 S_7. \tag{52}$$

The superheterodyne signal $S_{6\times 7}$ may be rewritten as $$S_{6\times 7}=S_{6\times 7}^{+}+S_{6\times 7}^{-} \tag{53}$$

where $$S_{6\times 7}^{+}=\tfrac{1}{2}A_6 A_7 \cos(2\pi\nu t+\vartheta), \tag{54}$$

$$S_{6\times 7}^{-}=\tfrac{1}{2}A_6 A_7 \cos(2\pi F t+\Phi), \tag{55}$$

and $$\nu=(f_1+f_2), \tag{56}$$

$$\vartheta=(\phi_6+\phi_7), \tag{57}$$

$$F=(f_1-f_2), \tag{58}$$

$$\Phi=(\phi_6-\phi_7). \tag{59}$$

Superheterodyne signal $S_{6\times 7}$ is therefore comprised of two sidebands, $S_{6\times 7}^{+}$ and $S_{6\times 7}^{-}$, of equal amplitude, one sideband with frequency $\nu$ and phase $\vartheta$ and a second sideband with frequency F and phase $\Phi$.

The remaining description of the first variant of the third embodiment is the same as the description given for corresponding steps of the first and third embodiments of the present invention.

It will be apparent to those skilled in the art that there are variants to the third embodiment corresponding to each of the variants of the first embodiment. The description of these variants of the third embodiment are the same as corresponding portions of the descriptions given for the corresponding variants of the first embodiment.

The fourth preferred embodiment of the second set of preferred embodiments of the present invention and variants thereof illustrated in FIGS. 4a–4d are all embodiments to measure a refractivity of a gas and/or the change in the optical path length of a measurement path due to the gas when the condition set fourth in Eq. (18) for the first three preferred embodiments and variants thereof is not satisfied, i.e., $$\left|\frac{\lambda_1}{\lambda_2} - \frac{l_1}{l_2}\right| \ll \left(\frac{l_2}{l_1}\right)(n_2 - n_1)\varepsilon. \tag{60}$$

Under the condition set fourth in Eq. (60), the approximate ratio, preferably the ratio $(K/\chi)$, must be either known or measured in accordance with Eqs. (7) and (14) for the second set of three preferred embodiments and variants thereof in addition to already described quantities in order to achieve the required accuracy in the determination of a refractivity of the gas and/or the change in the optical path of the measurement path due to the gas.

Each of the first set of three preferred embodiments and variants thereof can be converted from an apparatus and method for measuring a refractivity of the gas and/or the change in the optical path of the measurement path due to the gas to an apparatus and method for measuring $\chi$ and/or $(K/\chi)$. The conversions, as demonstrated in the following descriptions, are accomplished by changing the external mirror system of a given embodiment of the first set of three preferred embodiments and variants thereof so that the measuring path through a gas in measurement path 98 is replaced by a predetermined medium, preferably a vacuum, and the measurement leg has a fixed physical length. Accordingly, each of the second set of three embodiments and variants thereof are comprised of an unmodified and a modified apparatus and method from one of the first set of three embodiments and variants thereof, the modified apparatus and method being comprised of the unmodified apparatus and method with a modified external mirror system.

Reference is now made to FIGS. 4a–4d which depict in diagrammatic form the fourth preferred embodiment of the present invention. The description of the source of light beams 9 and 9b of the fourth embodiment is the same as that for light beam 9 of the first preferred embodiment and the description of the source of light beams 10 and 10b of the fourth embodiment is the same as that for light beam 10 of the first embodiment except that the condition on wavelengths $\lambda_1$ and $\lambda_2$ expressed by Eq. (18) is replaced by the condition set fourth in Eq. (60). Light beams 9 and 9b of the fourth embodiment are derived from a common light beam by beam splitter 153A, preferably a nonpolarizing type, and mirror 153B and light beams 10 and 10b of the fourth embodiment are derived from a common light beam by beam splitter 154A, preferably a nonpolarizing type, and mirror 154B (cf. FIG. 4a).

Because of the requirement in the fourth embodiment to measure $\chi$ and/or $(K/\chi)$, the fourth embodiment is comprised in part of the same apparatus and method as for the first embodiment and of additional means for determination of $\chi$ and/or $(K/\chi)$. The additional means for determination of $\chi$ and/or $(K/\chi)$ is the same as the apparatus and method of the first embodiment except for the external mirror system. Consequently, a number of elements of the apparatus shown in FIGS. 4a–4d for determination of $\chi$ and/or $(K/\chi)$ perform analogous operations as apparatus of the first embodiment, apart from the suffix "b" when referring to apparatus for determination of $\chi$ and/or $(K/\chi)$.

Figure 4A:
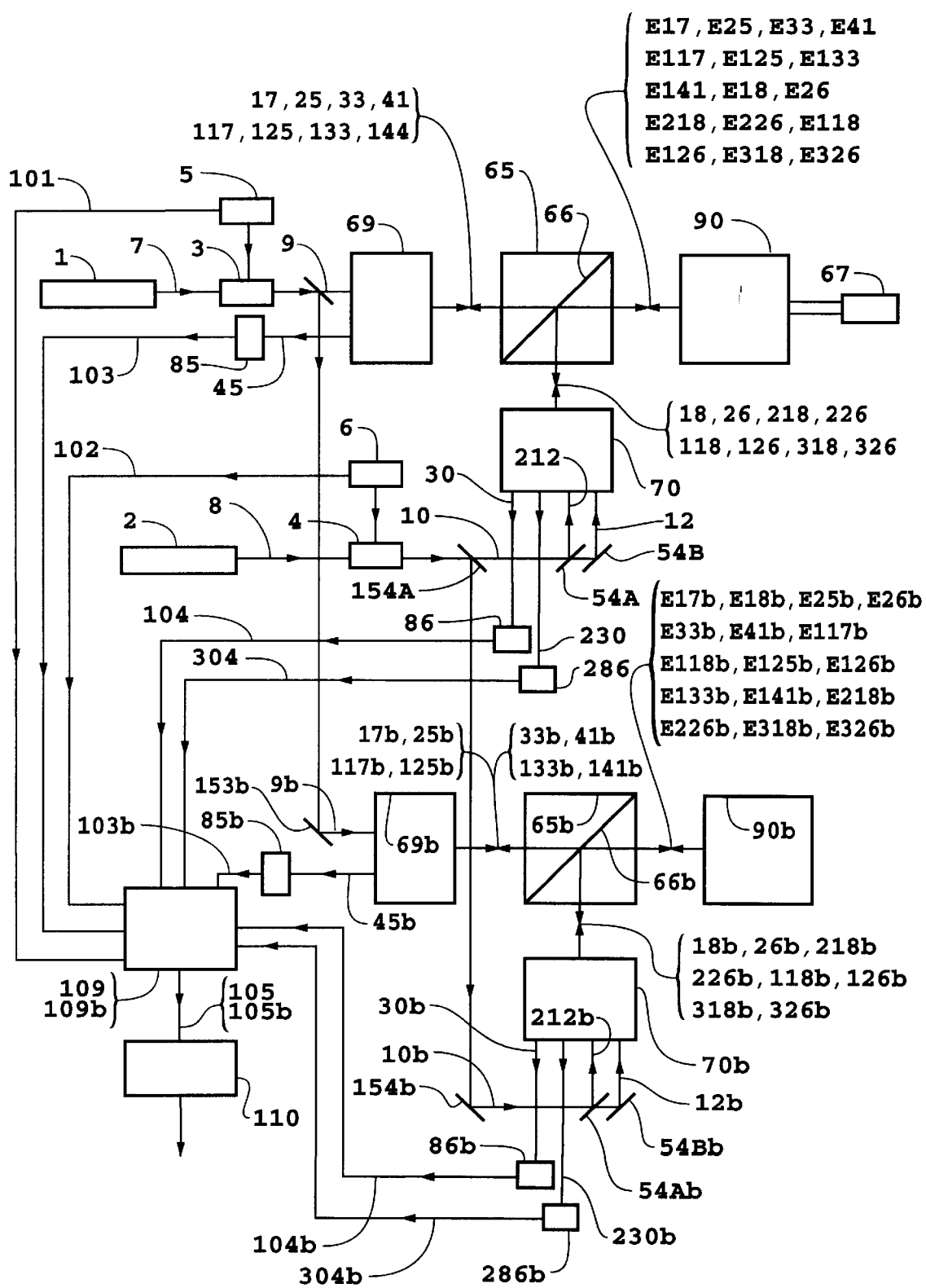
FIGS. 4a–4d taken together illustrate, in diagrammatic form, the presently preferred fourth embodiment of the present invention with FIG. 4a showing optical paths and electronic paths of apparatus comprised in part of the same apparatus as for the first preferred embodiment and optical paths and electronic paths of apparatus for determination of $\chi$ and $K/\chi$ wherein a number of elements perform analogous operations as like numbered elements of apparatus of the first preferred embodiment, apart from the suffix "b"
Figure 4B:
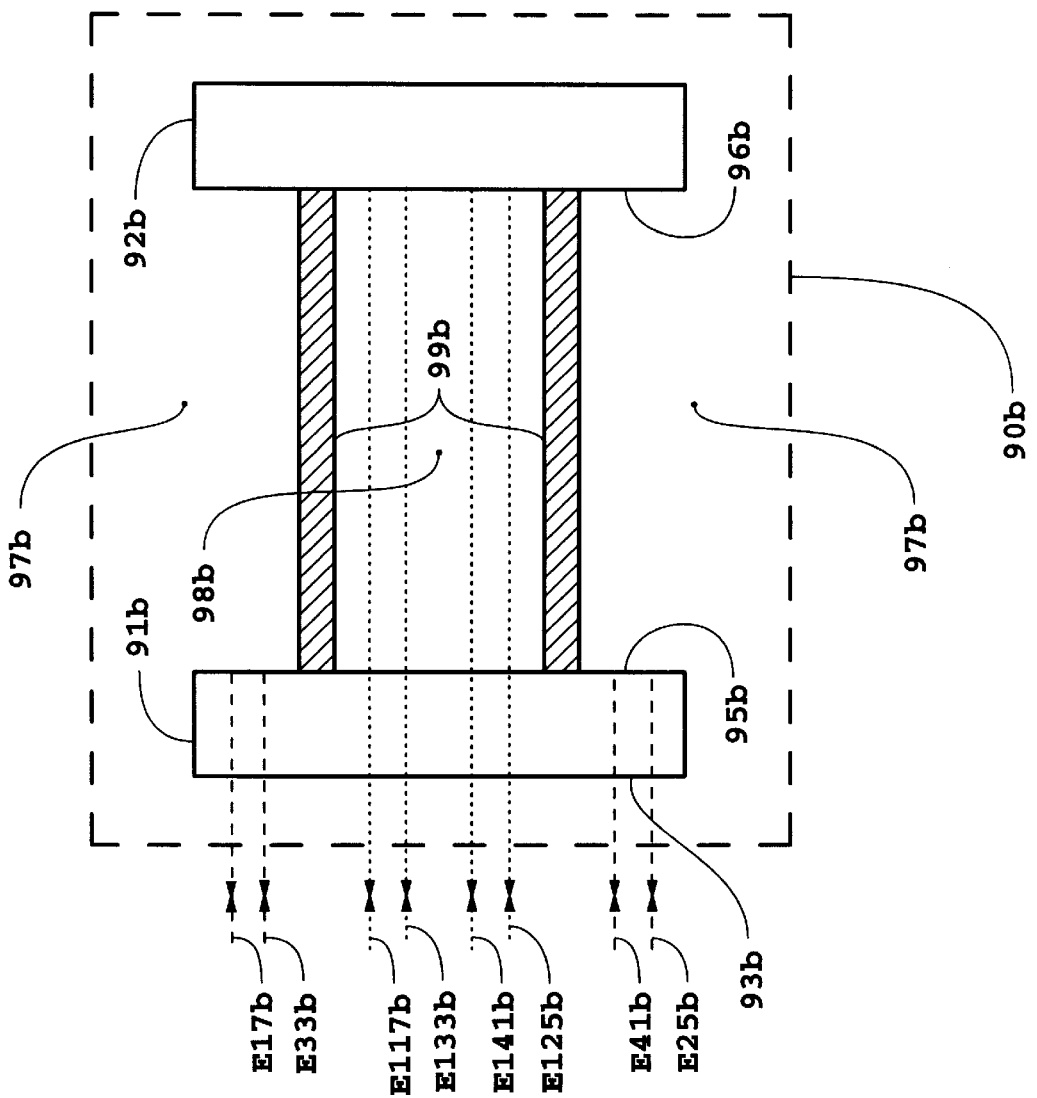
Figure 4C:
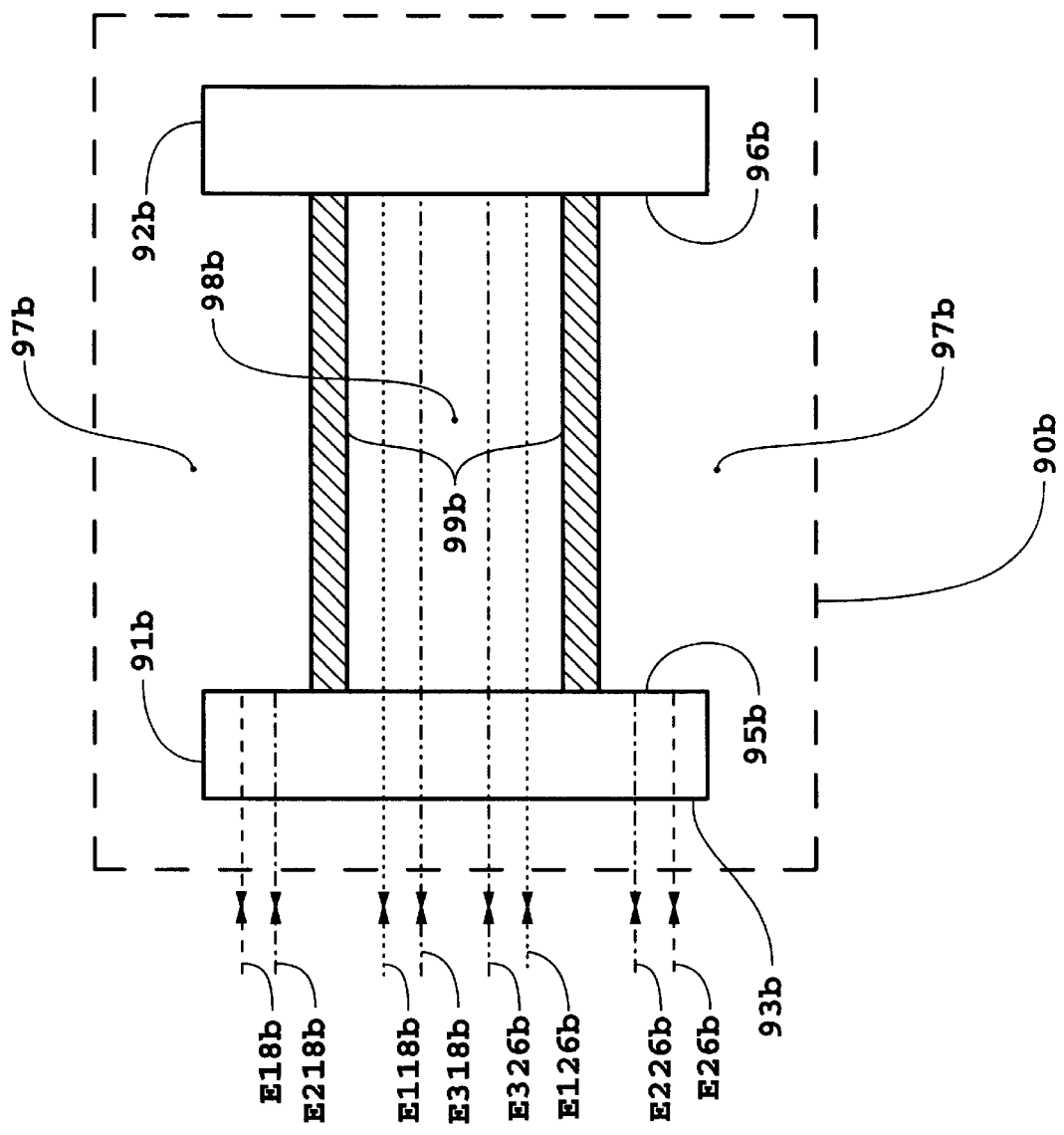

The external mirror system 90b of the fourth embodiment is shown in FIGS. 4b and 4c. The description of external mirror system 90b is the same as that for external mirror system 90 except with respect to the gas in the measurement path 98 and the round-trip physical length of the measurement path 98. The measurement leg in the external mirror system 90b of the fourth embodiment includes measurement path 98b as illustrated in FIGS. 4b and 4c, measurement path 98b preferably being an evacuated volume defined by mirrors 91b and 92b and a cylinder 99b of fixed length (L/2). Referring to FIGS. 4b and 4c, surface 95b is coated so as to reflect with high efficiency beams E17b, E25b, E33b, E41b, E18b, E26b, E218b, and E226b and to transmit with high efficiency beams E117b, E125b, E133b, E141b, E118b, E126b, E318b, and E326b. Surface 96b is coated to reflect with high efficiency beams E117b, E125b, E133b, E141b, E118b, E126b, E318b, and E326b.

The differences in the external mirror systems 90b and 90 lead to equations for the phases $\phi_{1b}$, $\phi_{2b}$, and $\phi_{3b}$ wherein the magnitude of phase shifts $\phi_{1b}$, $\phi_{2b}$, and $\phi_{3b}$, counterparts to phase shifts $\phi_1$, $\phi_2$, and $\phi_3$, respectively, are related to the round-trip physical length $L_i$ of path i of measurement path 98b and to reference paths as shown in FIGS. 4b and 4c according to the formulae $$\varphi_{1b} = \sum_{i=1}^{i=p_1} L_i k_1 + \zeta_{1b}, \tag{61}$$

$$\varphi_{2b} = \sum_{i=1}^{i=p_2} L_i k_2 + \zeta_{2b},$$

$$\varphi_{3b} = \sum_{i=p_2+1}^{i=p_1} L_i k_2 + \zeta_{3b}.$$

The detected heterodyne signals $s_{1b}$, $s_{2b}$, and $s_{3b}$, the counterparts to heterodyne signals $s_1$, $s_2$, and $s_3$, respectively, of the first embodiment are transmitted to electronic processor 109b as 103b, 104b, and 304b, respectively, in analog or digital format, preferably in digital format.

Figure 4D:
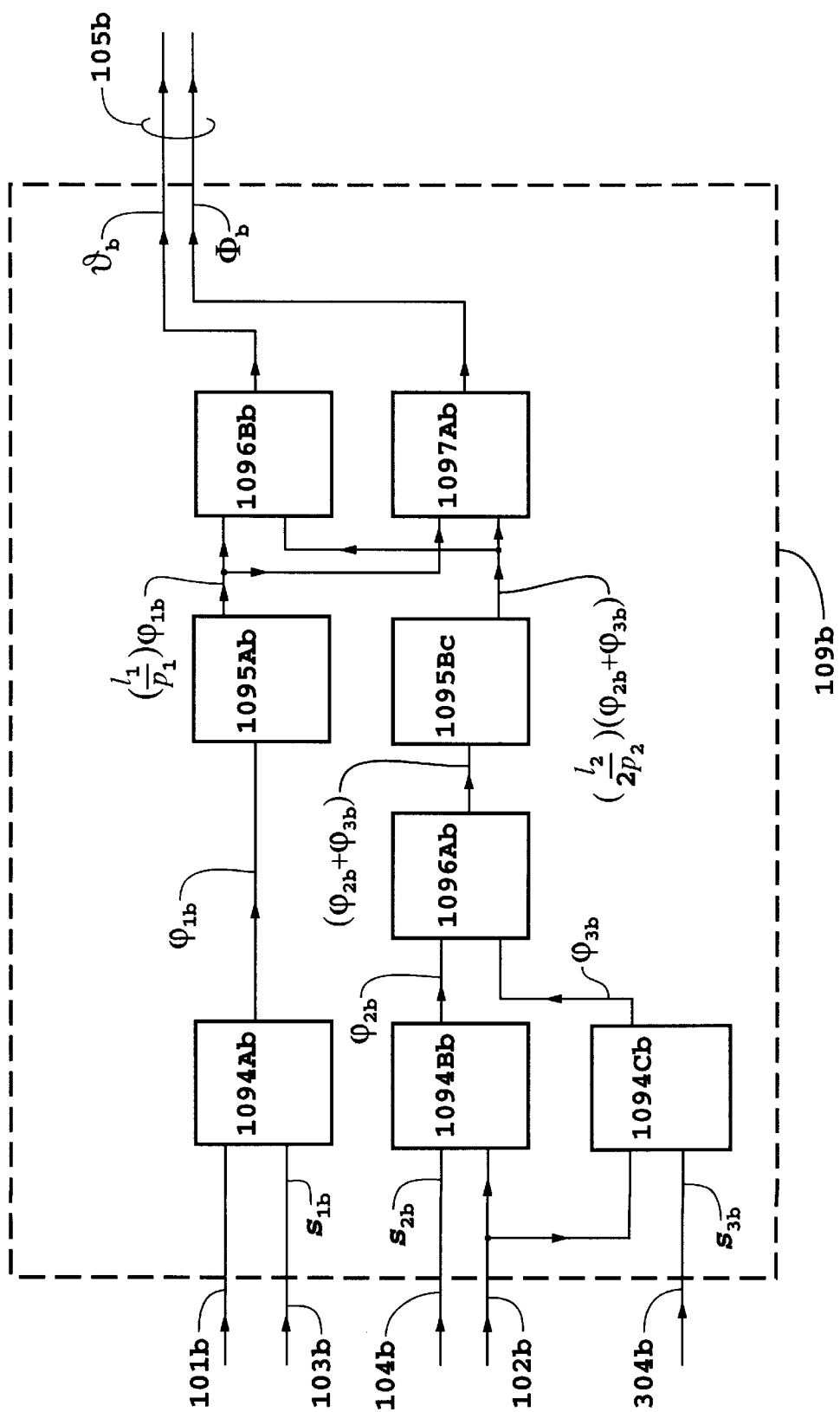

Referring now to FIG. 4d, electronic processor 109b preferably is comprised of alphameric numbered elements wherein the numeric component of the alphameric numbers indicate the function of an element, the same numeric component/function association as described for the electronic processing elements of the first embodiment depicted in FIG. 1f. The description of the steps in processing of heterodyne signals $s_1$, $s_{2b}$, and $s_{3b}$ by electronic processor 109b is the same as corresponding portions, according to the numeric component of the alphameric numbers of elements, of the descriptions given for steps in the processing of the heterodyne signals $s_1$, $s_2$, and $s_3$ of the first embodiment by electronic processor 109.

The processing of the heterodyne signals $s_{1b}$, $s_{2b}$, and $s_{3b}$ by electronic processor 109b creates the three phases $\phi_{1b}$, $\phi_{2b}$, and $\phi_{3b}$. The subsequent processing of $\phi_{1b}$, $\phi_{2b}$, and $\phi_{3b}$ by electronic processor 109b creates two phases $\vartheta_b$ and $\Phi_b$.

The ratio $(K/\chi)$ can be expressed by the formula $$\frac{K}{\chi} = \frac{(\Phi_b - Z_b)}{(\vartheta_b - \xi_b)} \tag{62}$$

where $Z_b$ and $\xi_b$ correspond to Z and $\xi$. Therefore $(K/\chi)$ is obtained by substantially dividing $\Phi_b$ by $\vartheta_b$ without the requirement for an accurate measurement of L to the same precision as required for $(K/\chi)$. The phase redundancy of $\Phi_b$ can be determined as part of the same procedure used to remove the phase redundancy of $\Phi$ in the unmodified apparatus and method of the first preferred embodiment incorporated as part of the third preferred embodiment.

The refractivity of the gas and/or the change in the optical path length of a measurement path due to the gas is subsequently obtained using Eqs. (7) and/or (14), respectively. Because of the non-negligible effect of $\tilde{\vartheta}$ in Eqs. (7) and (14), the phase redundancy of $\tilde{\vartheta}$ must also be resolved in addition to the resolution of the phase redundancy of $\tilde{\vartheta}_b$. The remainder of the description of the fourth embodiment is the same as corresponding portions of the first embodiment except with respect to the description of the procedure for the resolution of the phase redundancies of $\tilde{\vartheta}$ and of $\tilde{\vartheta}_b$.

For those applications where changes in the measurement path can be measured interferometrically, a feature for example of an application based on a distance measuring interferometer employed for measuring changes in the measurement path, the phase redundancy in $\tilde{\vartheta}$ can be resolved by recording the change in $\tilde{\vartheta}$ as the movable mirror 92 of the external mirror system 90 is scanned in a controlled manner by translator 67 over a given length from a null position, the null position being the position where the physical lengths of the measurement and reference legs are the substantially the same. The required accuracy for the determination of the null position is typically less accurate than the accuracy required for other parameters as exemplified in the following example: for $\lambda_1=0.633$ $\mu$m, $(n_1-1)\cong 3\times 10^{-4}$, $(n_2-n_1)\cong 1\times 10^{-5}$, $\epsilon\cong 10^{-9}$, and the condition set fourth in Eq. (17), the required accuracy for the null position determination corresponds to an uncertainty in $\tilde{\vartheta}$ of the order of ±3.

For those applications where the determination of the refractivity and/or or the change in the optical path length due to the gas in a measurement leg is made and mirror 92 of the external mirror system does not have a scanning capability such as considered in the preceding paragraph, other procedures are available for the resolution of the phase redundancies of $\tilde{\vartheta}$ and $\tilde{\vartheta}_b$. The effective wavelengths of $\tilde{\vartheta}$ and $\tilde{\vartheta}_b$ are substantially the same so that only procedures for the resolution of phase redundancy in either $\tilde{\vartheta}$ or $\tilde{\vartheta}_b$ need be described.

The second procedure described for the resolution of the phase redundancy of $\Phi$ can be adapted for resolution of the phase redundancies of $\tilde{\vartheta}$, the second procedure being based on the use of a series of external mirror systems 90 where the round-trip physical lengths L for the measurement legs of the external mirror system 90 form a geometric progression. The smallest or first round-trip physical length in the series will be approximately $\lambda_1/(4p_1)$ divided by the relative precision that the initial value of $\tilde{\vartheta}$ is known. The physical length of the second external mirror system 90 in the series will be approximately the length of the first external mirror system 90 divided by the relative precision that $\tilde{\vartheta}$ is measured using the first external mirror system 90. This is again a geometric progression procedure, the resulting physical lengths forming a geometric progression, which is continued until the length of the external mirror system 90 used to measure the refractivity or the change in optical path length due to the refractivity of the gas would be exceeded if the number of external mirror systems 90 in series were incremented by one. A typical round-trip physical length for the first external mirror system 90 in the series for the resolution of phase redundancy in $\tilde{\vartheta}$ is of the order of 0.1 mm, a typical round-trip physical length for the second external mirror system 90 in the series is of the order of 10 mm, and a typical round-trip physical length for a third external mirror system 90 in the series if required is of the order of 1000 mm. The physical lengths for the external mirror systems 90 in the series for the resolution of phase redundancy in $\Phi$ are typically orders of magnitude larger than the physical lengths for the external mirror systems 90 in the series for the resolution of phase redundancy in $\tilde{\vartheta}$.

A third procedure is based upon the use of a source (not shown in FIGS. 4a–4d) of a series of known wavelengths and measuring $\tilde{\vartheta}$ for these wavelengths. The number of known wavelengths required for the resolution of the phase redundancy is generally comprised of a small set.

Another procedure to resolve the phase redundancy in $\tilde{\vartheta}_b$ is to observe the changes in $\tilde{\vartheta}_b$ as the measuring path 98b is changed from gas to an evacuated state (the vacuum pump and requisite gas handling system are not shown in FIGS. 4a–4d) to resolve the phase redundancy in $\tilde{\vartheta}_b$. The problems normally encountered in measuring absolute values for refractivity and changes in the optical path length due to the refractivity of the gas based in part on changing the gas pressure from a non-zero value to a vacuum are not present in the third preferred embodiment because of a relatively large uncertainty of the order of ±3 typically permitted in the determination of $\tilde{\vartheta}_b$.

The offset terms $\xi_b$ and $Z_b$ that are present in Eq. (62) are terms that require determination and may require monitoring if variable in time. One procedure for the determination of $\xi_b$ and $Z_b$ is based on replacement of mirror 91b of the external mirror system 90b with a mirror Z91b (not shown in FIGS. 4a–4c) having a surface Z93b corresponding to surface 93b of mirror 91b coated so as be a reflecting surface for both wavelengths $\lambda_1$ and $\lambda_2$ and measuring the resulting $\tilde{\vartheta}_b$ and $\Phi_b$. Let the resulting values of $\tilde{\vartheta}_b$ and $\Phi_b$ be $\tilde{\vartheta}_{bR}$ and $\Phi_{bR}$, respectively. The quantities $\xi_b$ and $Z_b$ are related to $\tilde{\vartheta}_{bR}$ and $\Phi_{bR}$, respectively by the formulae $$\xi_b=\tilde{\vartheta}_{bR}, \qquad (63)$$

$$Z_b=\Phi_{bR}. \qquad (64)$$

The non-electronic contributions to $\xi_b$ and $Z_b$ should be substantially constant in time because of the significant level of compensation that takes place in the differential plane mirror interferometer 69b, the differential plane mirror interferometer group 70b, beam splitter 65b, and external mirror system 90b. The electronic contributions to $\xi_b$ and $Z_b$ are monitored by purely electronic means (not shown).

The wavenumber $\chi$ is calculated by the computer using the measured values for $\tilde{\vartheta}_b$ and $\xi_b$ and the formula $$\chi=(\tilde{\vartheta}_b-\xi_b)/(2L). \qquad (65)$$

The ratio K/$\chi$ is calculated by the computer using Eq. (62).

It will be apparent to those skilled in the art that there are variants to the fourth embodiment corresponding to each of the variants of the first embodiment. The description of these variants of the fourth embodiment are the same as corresponding portions of the descriptions given for the corresponding variants of the first embodiment.

It will also be apparent to those skilled in the art how to construct embodiments and variants thereof which are analogs of the second embodiment and variants thereof and of the third embodiment and variants thereof in the same way that the fourth embodiment and variants thereof are analogs of the first embodiment and variants thereof.

It will be appreciated by those skilled in the art that alternative data processing may be considered for the preferred embodiments and variants thereof of the present invention without departing from the spirit and scope of the present invention.

It will also be appreciated by those skilled in the art that the differential plane mirror interferometers and the external mirror system of the additional means for the determination of (K/χ) and χ in the second set of preferred embodiments and variants thereof may be configured such that one of the light beams corresponding to one of the wavelengths may enter and exit from one end of the external mirror system and a second of the light beams corresponding to a differing second wavelength may enter and exit from an opposite end of the external mirror system in contrast to the same end as disclosed in the preferred embodiments and variants thereof without departing from the scope or spirit of the invention as defined in the claims. With the reconfiguring of the external mirror system, beam splitter 65b may obviously be omitted, the light beams of differing wavelengths entering and exiting through the mirrors 91b and 92b with the reflecting and transmitting coatings on mirror surfaces 95b and 96b having been reconfigured accordingly.

It will be apparent to those skilled in the art that the embodiments and variants thereof of the present invention disclosed herein will typically generate a phase Φ with a reduced sensitivity to relative differences in group delays experienced by the heterodyne signals, the heterodyne signals for a given embodiment or variant thereof each having substantially the same frequency spectrum.

It will be further appreciated by those skilled in the art that both the x and y polarization components of beam 9 and/or of beam 10 of the preferred embodiments and variants thereof may be frequency shifted without departing from the scope and spirit of the invention, $f_1$ remaining the difference in frequencies of the x and y polarization components of beam 9 and $f_2$ remaining the difference in frequencies of the x and y polarization components of beam 10. Improved isolation of an interferometer and a laser source is generally possible by frequency shifting both x and y polarization components of a beam, the degree of improved isolation depending on the means used for generating the frequency shifts.

It will be appreciated by those skilled in the art that the wavelength $\lambda_1$ of the light beam used for the determination of $\phi_1$ in Eqs. (14) and (20) may be different from both of the two wavelengths used to determine the change in the optical path length of the measuring path due gas in the measuring path without departing from the scope and spirit of the present invention. The requisite reciprocal dispersive power $\Gamma_3$ would be defined in terms of the indices of refraction $n_1$, $n_2$, and $n_3$ of the gas at the three wavelengths $\lambda_1$, $\lambda_2$, and $\lambda_3$, respectively, according to the formula $$\Gamma_3 = \frac{(n_1 - 1)}{(n_3 - n_2)} \tag{66}$$

for $\lambda_3 < \lambda_2$.

It will be further appreciated by those skilled in the art that the two frequency components of either or both beams 9 and 10 may be spatially separated at any point following the means for introducing the frequency shifts and prior to entering the respective interferometers of the described preferred embodiments without departing from the scope and spirit of the present invention. If the two frequency components of either of the two beams are spatially separated for any significant distance from the respective interferometer, it may be necessary to employ alternative reference beams such as described in the first embodiment.

The illustrations in the figures depict preferred embodiments and variants thereof of the present invention wherein all of the optical beams for an embodiment are in a single plane. Clearly, modifications using multiple planes can be made to one or more of the preferred embodiments and variants thereof without departing from the scope or spirit of the invention.

The preferred embodiments and variants thereof of the present invention have external mirror systems 90b and/or 90 wherein the measurement paths for $\lambda_1$ and $\lambda_2$ have the same round-trip physical length per pass through the system and the reference paths for $\lambda_1$ and $\lambda_2$ have the same round-trip physical length per pass. It will be appreciated by those skilled in the art that the measurement paths for $\lambda_1$ and $\lambda_2$ can have different physical lengths per pass and the reference paths for $\lambda_1$ and $\lambda_2$ can have different physical lengths per pass without departing from the scope and spirit of the present invention as defined in the claims. It will be further appreciated by those skilled in the art that the measurement paths for $\lambda_1$ and $\lambda_2$ can be physically displaced one from the other, and the reference paths for $\lambda_1$ and $\lambda_2$ can be physically displaced one from the other without departing from the scope and spirit of the present invention as defined in the claims although there may be some degradation in performance with regard frequency response of the embodiments and/or in accuracy of calculated quantities due to for example spatial gradients in the refractivity of a gas in a measurement path.

The preferred embodiments and variants thereof of the present invention are all configured for use of heterodyne detection. It will be appreciated by those skilled in the art that homodyne detection can be employed in each of the preferred embodiments and variants thereof without departing from the scope and spirit of the present invention as defined in the claims. Homodyne receivers would be employed such as disclosed in commonly owned U.S. Pat. No. 5,663,793 entitled "Homodyne Interferometric Receiver and Method," issued Sep. 2, 1997 in the name of P. de Groot. The computation of the refractivity of a gas and/or the change in the optical path length of a measurement path due to the gas would be obtained for example in the homodyne version of the first preferred embodiment directly from homodyne phases $\phi_{1H}$, and $\phi_{2H}$, the homodyne phases $\phi_{1H}$ and $\phi_{2H}$ being counterparts to phases $\phi_1$ and $\phi_2$ of the first preferred embodiment, and with homodyne versions of Eqs. (7) and (14).

The second set of preferred embodiments of the present invention and variants thereof measure the ratio (K/χ) and χ and use the measured values of (K/χ) and χ in the computation of the refractivity of a gas and/or the change in the optical path length of a measurement path due to the gas. It will be appreciated by those skilled in the art that the measured values of (K/χ) and χ can be used as error signals in a feedback system such that either or both the condition expressed by Eq. (18) is satisfied and χ is constant without departing from the scope and spirit of the present invention as defined in the claims. The measured values of either or both (K/χ) and χ in the feedback system are sent to either or both source 1 and source 2 and used to control the respective wavelengths of either or both source 1 and source 2, for example by controlling either or both the injection current and temperature of a diode laser or the cavity frequency of an external cavity diode laser.

It will be appreciated by those skilled in the art that combinations of the means of the second group of preferred embodiments and variants thereof to measure the ratio (K/χ) and χ and of the means of the first group of preferred embodiments and variants thereof may be used to determine the refractivity of a gas and/or the change in the optical path length of a measurement path due to the gas other than the combinations used in the second group of preferred embodiments and variants thereof without departing from the scope or spirit of the invention as defined in the claims.

Figure 5:
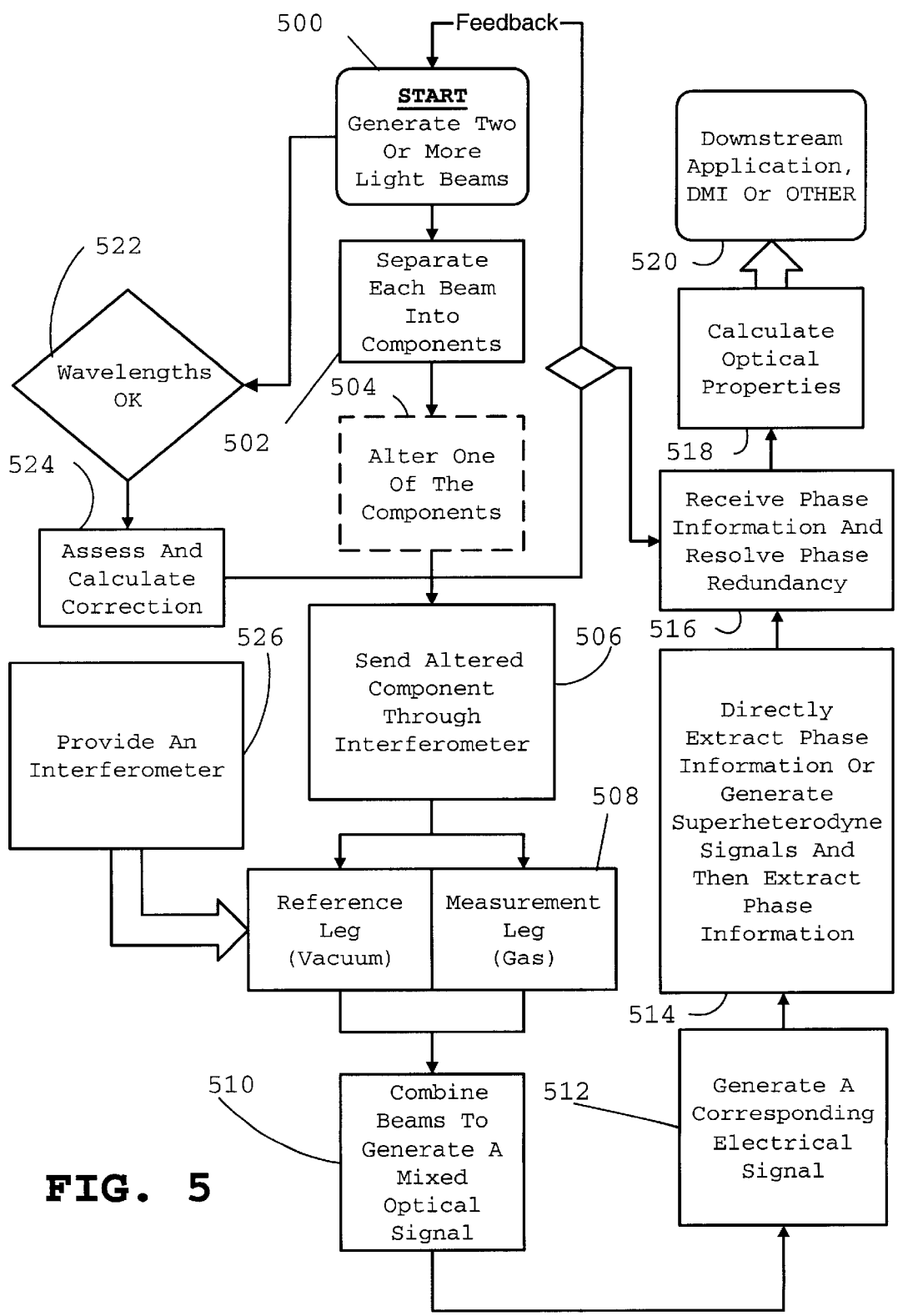
FIG. 5 is a high-level flowchart depicting various steps carried out in practicing a method in accordance with the invention.

Reference is now made to FIG. 5 which is a generalized flowchart depicting via blocks 500–526 various steps for practicing an inventive method for measuring and monitoring the refractivity of a gas in a measurement path and/or the change in the optical path length of the measurement path due to the gas wherein the refractivity of the gas may be changing and/or the physical length of the measurement path may be changing. While it will be evident that the inventive method depicted in FIG. 5 may be carried out using the inventive apparatus disclosed hereinabove, it will also be apparent to those skilled in the art that it may also be implemented with apparatus other than that disclosed. For example, it will be apparent that one need not use differential plane mirror interferometers such as that used in the preferred embodiments, but rather may use other conventional interferometric arrangements so long as the required reference and measurement legs are present. In addition, it will be evident that one may use either a homodyne approach or one in which heterodyning techniques are advantageously employed. As will be further appreciated, many of the steps in FIG. 5 may be carried out via appropriate software run on a general purpose computer or a suitably programmed microprocessor either of which may be used to control other elements of the system as needed.

As seen in FIG. 5, one starts in block 500 by providing two or more light beams having different wavelengths which preferably have an approximate harmonic relationship as previously described. In block 502, the light beams are separated into components which in block 504 are preferably altered by either polarization or spatial encoding, or frequency shifting or both. Otherwise, the light beams may simply be left unaltered and passed through to block 506.

As shown in blocks 522 and 524, the relationship of the wavelengths of the light beams may be monitored and if their wavelengths are not within the limits previously discussed, one can adopt corrective measures to compensate from departures of the relationship of the wavelengths from the desired relationship of the wavelengths. Either the departures can be used to provide feedback to control the wavelengths of the light beam sources or corrections can be established and used in subsequent calculations which are influenced by departures or some combination of both approaches can be implemented.

In parallel or contemporaneously with generating the light beams in block 500, one also provides as indicated in block 526 an interferometer having two legs, a reference leg and the other a measurement leg wherein a portion of the measurement path is in a gas whose refractivity and/or effect on the optical path length of the measurement path are to be measured.

As shown by blocks 506 and 508, the previously generated light beam components are introduced into the interferometer legs so that each component has its phase shifted based on the optical path length it experiences in traveling through the physical length of its assigned leg.

After the beams emerge from block 508, they are combined in block 510 to generate a mixed optical signal. These mixed optical signals are then sent to block 512 where by means of photodetection corresponding electrical signals, preferably heterodyne, are generated, and these electrical signals contain information about the relative phases between the light beam components. Preferably the electrical signals are heterodyne signals brought about by previously frequency shifting treatment.

In block 514, the electrical signals may be directly analyzed to extract relative phase information which can then be passed on to blocks 516–520 or, superheterodyne signals are generated and subsequently analyzed for the relative phase information.

In block 516, any phase ambiguities in homodyne, heterodyne, and/or superheterodyne signals are resolved, preferably by means and calculations previously elaborated in connection with describing the preferred embodiments.

In block 518, the refractivity of the gas and/or the effect of the refractivity of the gas on the optical path length of the measurement path are calculated, corrections are applied as previously decided, and output signals are generated for subsequent downstream applications or data format requirements.

Those skilled in the art may make other changes to the inventive apparatus and methods without departing from the scope of the inventive teachings. Therefore, it is intended that the embodiments shown and described be considered as illustrative and not in a limiting sense.

The interferometry systems described above can be especially useful in lithography applications (as diagrammatically indicated at 67) used for fabricating large scale integrated circuits such as computer chips and the like. Lithography is the key technology driver for the semiconductor manufacturing industry. Overlay improvement is one of the five most difficult challenges down to and below 100 nm line widths (design rules), see for example the *Semiconductor Industry Roadmap*, p82 (1997). Overlay depends directly on the performance, i.e. accuracy and precision, of the distance measuring interferometers used to position the wafer and reticle (or mask) stages. Since a lithography tool may produce $50–100M/year of product, the economic value from improved performance distance measuring interferometers is substantial. Each 1% increase in yield of the lithography tool results in approximately $1M/year economic benefit to the integrated circuit manufacturer and substantial competitive advantage to the lithography tool vendor.

The function of a lithography tool is to direct spatially patterned radiation onto a photoresist-coated wafer. The process involves determining which location of the wafer is to receive the radiation (alignment) and applying the radiation to the photoresist at that location (exposure).

To properly position the wafer, the wafer includes alignment marks on the wafer that can be measured by dedicated sensors. The measured positions of the alignment marks define the location of the wafer within the tool. This information, along with a specification of the desired patterning of the wafer surface, guides the alignment of the wafer relative to the spatially patterned radiation. Based on such information, a translatable stage supporting the photoresist-coated wafer moves the wafer such that the radiation will expose the correct location of the wafer.

During exposure, a radiation source illuminates a patterned reticle, which scatters the radiation to produce the spatially patterned radiation. The reticle is also referred to as a mask, and these terms are used interchangeably below. In the case of reduction lithography, a reduction lens collects the scattered radiation and forms a reduced image of the reticle pattern. Alternatively, in the case of proximity printing, the scattered radiation propagates a small distance (typically on the order of microns) before contacting the wafer to produce a 1:1 image of the reticle pattern. The radiation initiates photo-chemical processes in the photoresist that convert the radiation pattern into a latent image within the photoresist.

The interferometry systems described above are important components of the positioning mechanisms that control the position of the wafer and reticle, and register the reticle image on the wafer.

In general, the lithography system, also referred to as an exposure system, typically includes an illumination system and a wafer positioning system. The illumination system includes a radiation source for providing radiation such as ultraviolet, visible, x-ray, electron, or ion radiation, and a reticle or mask for imparting the pattern to the radiation, thereby generating the spatially patterned radiation. In addition, for the case of reduction lithography, the illumination system can include a lens assembly for imaging the spatially patterned radiation onto the wafer. The imaged radiation exposes photoresist coated onto the wafer. The illumination system also includes a mask stage for supporting the mask and a positioning system for adjusting the position of the mask stage relative to the radiation directed through the mask. The wafer positioning system includes a wafer stage for supporting the wafer and a positioning system for adjusting the position of the wafer stage relative to the imaged radiation. Fabrication of integrated circuits can include multiple exposing steps. For a general reference on lithography, see, for example, J. R. Sheats and B. W. Smith, in *Microlithography: Science and Technology* (Marcel Dekker, Inc., New York, 1998), the contents of which are incorporated herein by reference.

The interferometry systems described above can be used to precisely measure the positions of each of the wafer stage and mask stage relative to other components of the exposure system, such as the lens assembly, radiation source, or support structure. In such cases, the interferometry system can be attached to a stationary structure and the measurement object attached to a movable element such as one of the mask and wafer stages. Alternatively, the situation can be reversed, with the interferometry system attached to a movable object and the measurement object attached to a stationary object.

More generally, the interferometry systems can be used to measure the position of any one component of the exposure system relative to any other component of the exposure system in which the interferometry system is attached, or supported by one of the components and the measurement object is attached, or is supported by the other of the components.

Figure 6A:
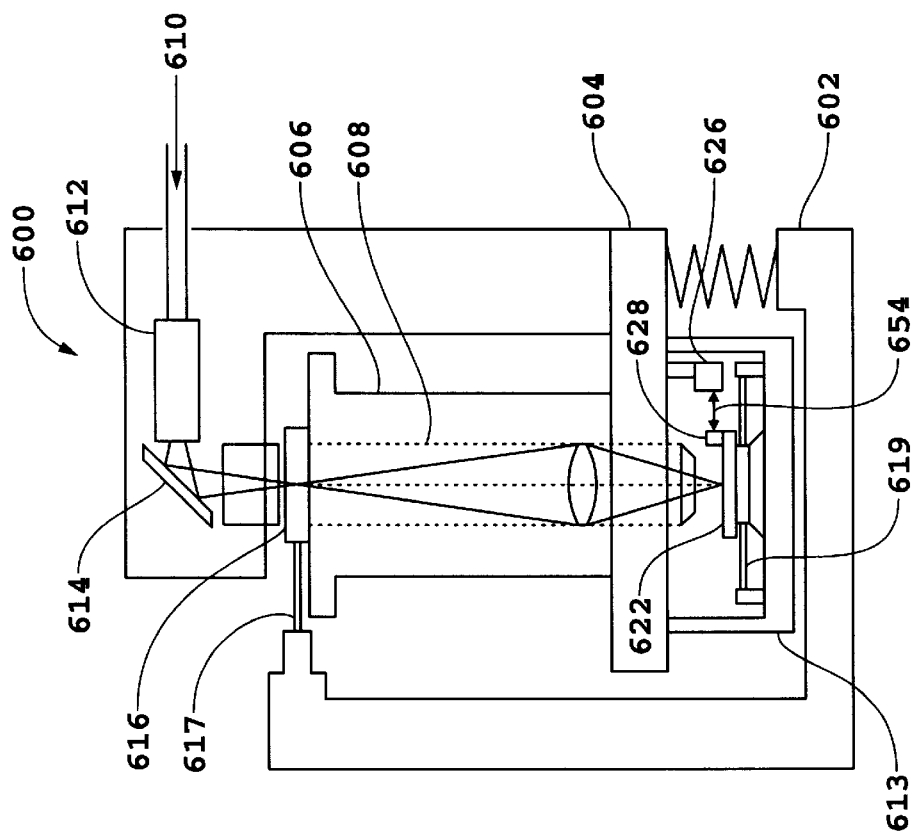

An example of a lithography scanner 600 using an interferometry system 626 is shown in FIG. 6a. The interferometry system is used to precisely measure the position of a wafer within an exposure system. Here, stage 622 is used to position the wafer relative to an exposure station. Scanner 600 comprises a frame 602, which carries other support structures and various components carried on those structures. An exposure base 604 has mounted on top of it a lens housing 606 atop of which is mounted a reticle or mask stage 616 used to support a reticle or mask. A positioning system for positioning the mask relative to the exposure station is indicated schematically by element 617. Positioning system 617 can include, e.g., piezoelectric transducer elements and corresponding control electronics. Although, it is not included in this described embodiment, one or more of the interferometry systems described above can also be used to precisely measure the position of the mask stage as well as other moveable elements whose position must be accurately monitored in processes for fabricating lithographic structures (see supra Sheats and Smith *Microlithography: Science and Technology*).

Suspended below exposure base 604 is a support base 613 that carries wafer stage 622. Stage 622 includes a plane mirror for reflecting a measurement beam 654 directed to the stage by interferometry system 626. A positioning system for positioning stage 622 relative to interferometry system 626 is indicated schematically by element 619. Positioning system 619 can include, e.g., piezoelectric transducer elements and corresponding control electronics. The measurement beam reflects back to the interferometry system, which is mounted on exposure base 604. The interferometry system can be any of the embodiments described previously.

During operation, a radiation beam 610, e.g., an ultraviolet (UV) beam from a UV laser (not shown), passes through a beam shaping optics assembly 612 and travels downward after reflecting from mirror 614. Thereafter, the radiation beam passes through a mask (not shown) carried by mask stage 616. The mask (not shown) is imaged onto a wafer (not shown) on wafer stage 622 via a lens assembly 608 carried in a lens housing 606. Base 604 and the various components supported by it are isolated from environmental vibrations by a damping system depicted by spring 620.

In other embodiments of the lithographic scanner, one or more of the interferometry systems described previously can be used to measure distance along multiple axes and angles associated for example with, but not limited to, the wafer and reticle (or mask) stages. Also, rather than a UV laser beam, other beams can be used to expose the wafer including, e.g., x-ray beams, electron beams, ion beams, and visible optical beams.

In addition, the lithographic scanner can include a column reference in which interferometry system 626 directs the reference beam to lens housing 606 or some other structure that directs the radiation beam rather than a reference path internal to the interferometry system. The interference signal produced by interferometry system 626 when combining measurement beam 654 reflected from stage 622 and the reference beam reflected from lens housing 606 indicates changes in the position of the stage relative to the radiation beam. Furthermore, in other embodiments the interferometry system 626 can be positioned to measure changes in the position of reticle (or mask) stage 616 or other movable components of the scanner system. Finally, the interferometry systems can be used in a similar fashion with lithography systems involving steppers, in addition to, or rather than, scanners.

Figure 6B:
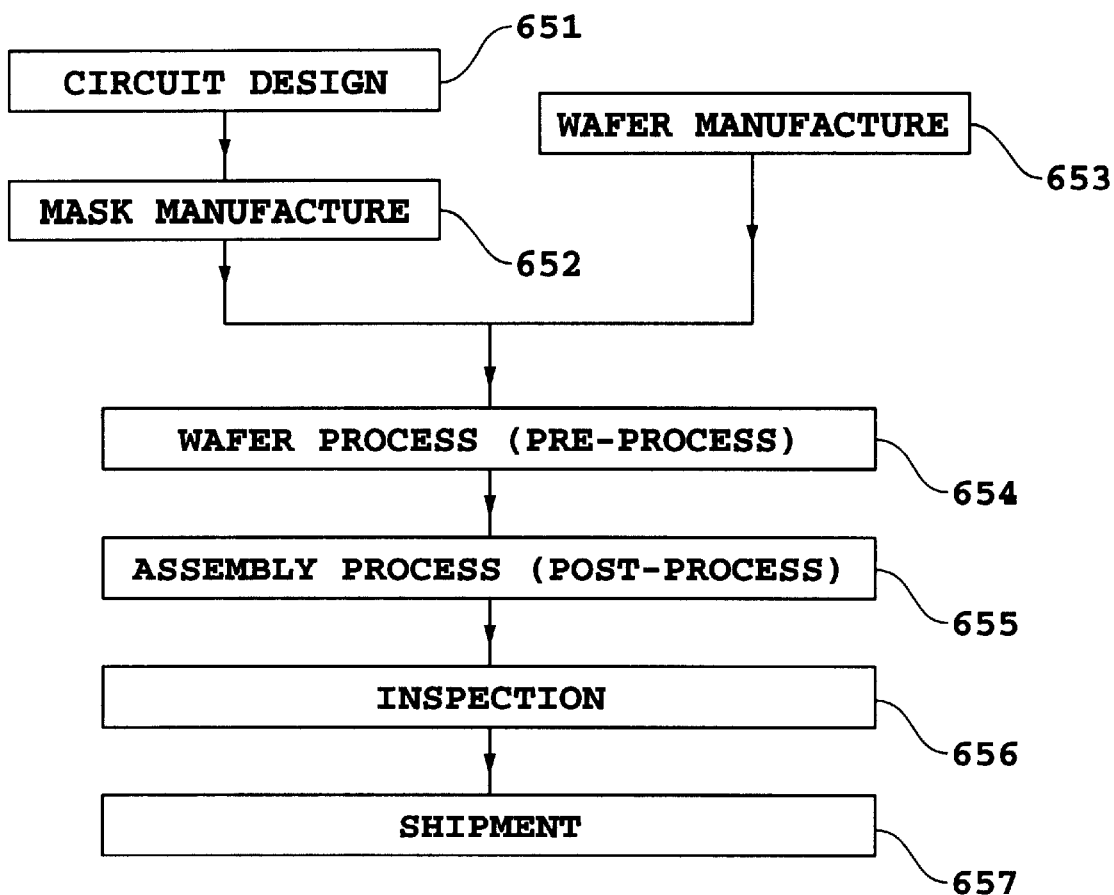

As is well known in the art, lithography is a critical part of manufacturing methods for making semiconducting devices. For example, U.S. Pat. No. 5,483,343 outlines steps for such manufacturing methods. These steps are described below with reference to FIGS. 6b and 6c. FIG. 6b is a flow chart of the sequence of manufacturing a semiconductor device such as a semiconductor chip (e.g. IC or LSI), a liquid crystal panel or a CCD. Step 651 is a design process for designing the circuit of a semiconductor device. Step 652 is a process for manufacturing a mask on the basis of the circuit pattern design. Step 653 is a process for manufacturing a wafer by using a material such as silicon.

Step 654 is a wafer process which is called a pre-process wherein, by using the so prepared mask and wafer, circuits are formed on the wafer through lithography. Step 655 is an assembling step, which is called a post-process wherein the wafer processed by step 654 is formed into semiconductor chips. This step includes assembling (dicing and bonding) and packaging (chip sealing). Step 656 is an inspection step wherein operability check, durability check, and so on of the semiconductor devices produced by step 655 are carried out. With these processes, semiconductor devices are finished and they are shipped (step 657).

Figure 6C:
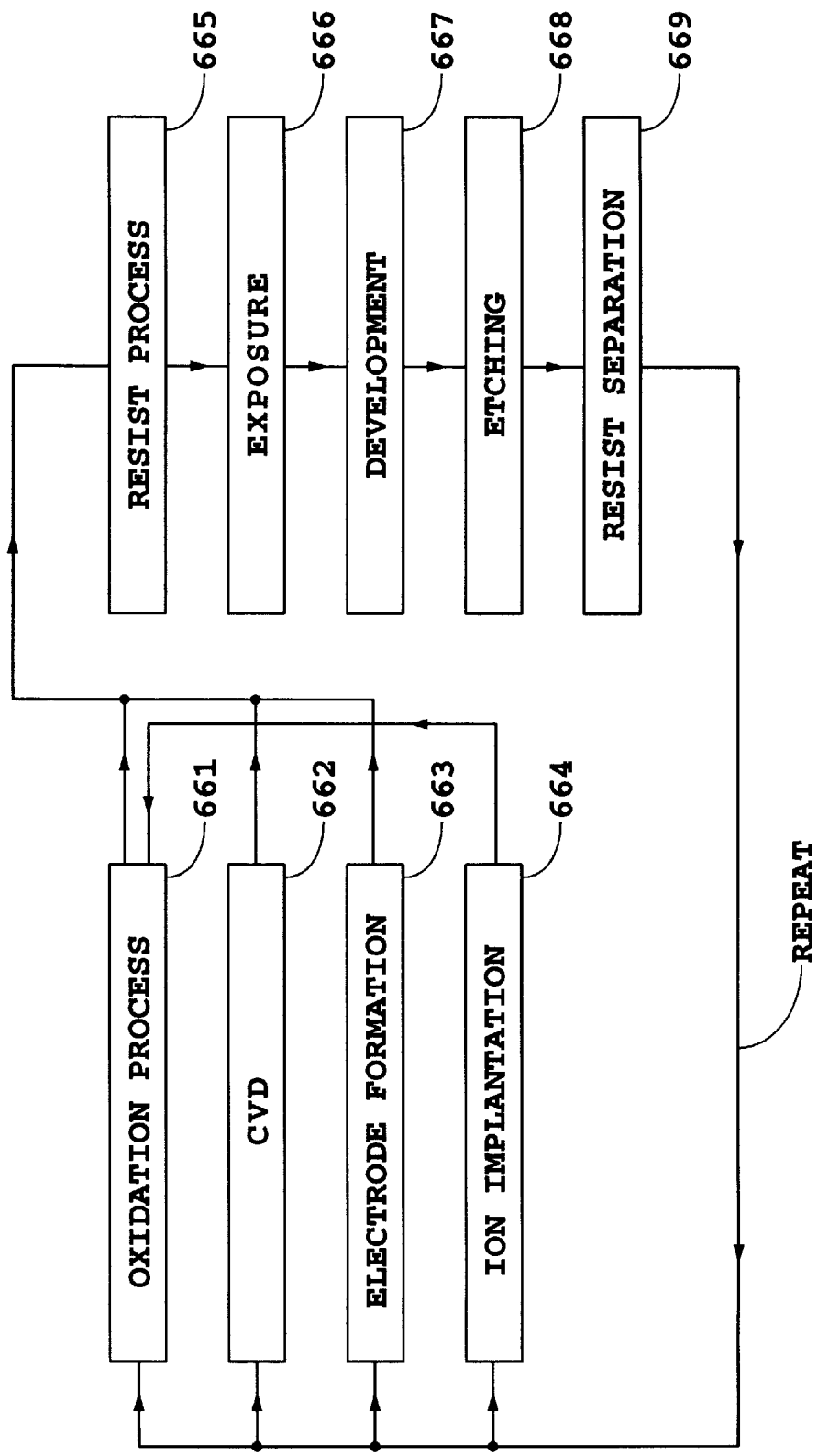

FIG. 6c is a flow chart showing details of the wafer process. Step 661 is an oxidation process for oxidizing the surface of a wafer. Step 662 is a CVD process for forming an insulating film on the wafer surface. Step 663 is an electrode forming process for forming electrodes on the wafer by vapor deposition. Step 664 is an ion implanting process for implanting ions to the wafer. Step 665 is a photoresist process for applying a photoresist (photosensitive material) to the wafer. Step 666 is an exposure process for printing, by exposure, the circuit pattern of the mask on the wafer through the exposure apparatus described above. Step 667 is a developing process for developing the exposed wafer. Step 668 is an etching process for removing portions other than the developed photoresist image. Step 669 is a photoresist separation process for separating the photoresist material remaining on the wafer after being subjected to the etching process. By repeating these processes, circuit patterns are formed and superimposed on the wafer.

The interferometry systems described above can also be used in other applications in which the relative position of an object needs to be measured precisely. For example, in applications in which a write beam such as a laser, x-ray, ion, or electron beam, marks a pattern onto a substrate as either the substrate or beam moves, the interferometry systems can be used to measure the relative movement between the substrate and write beam.

Figure 7:
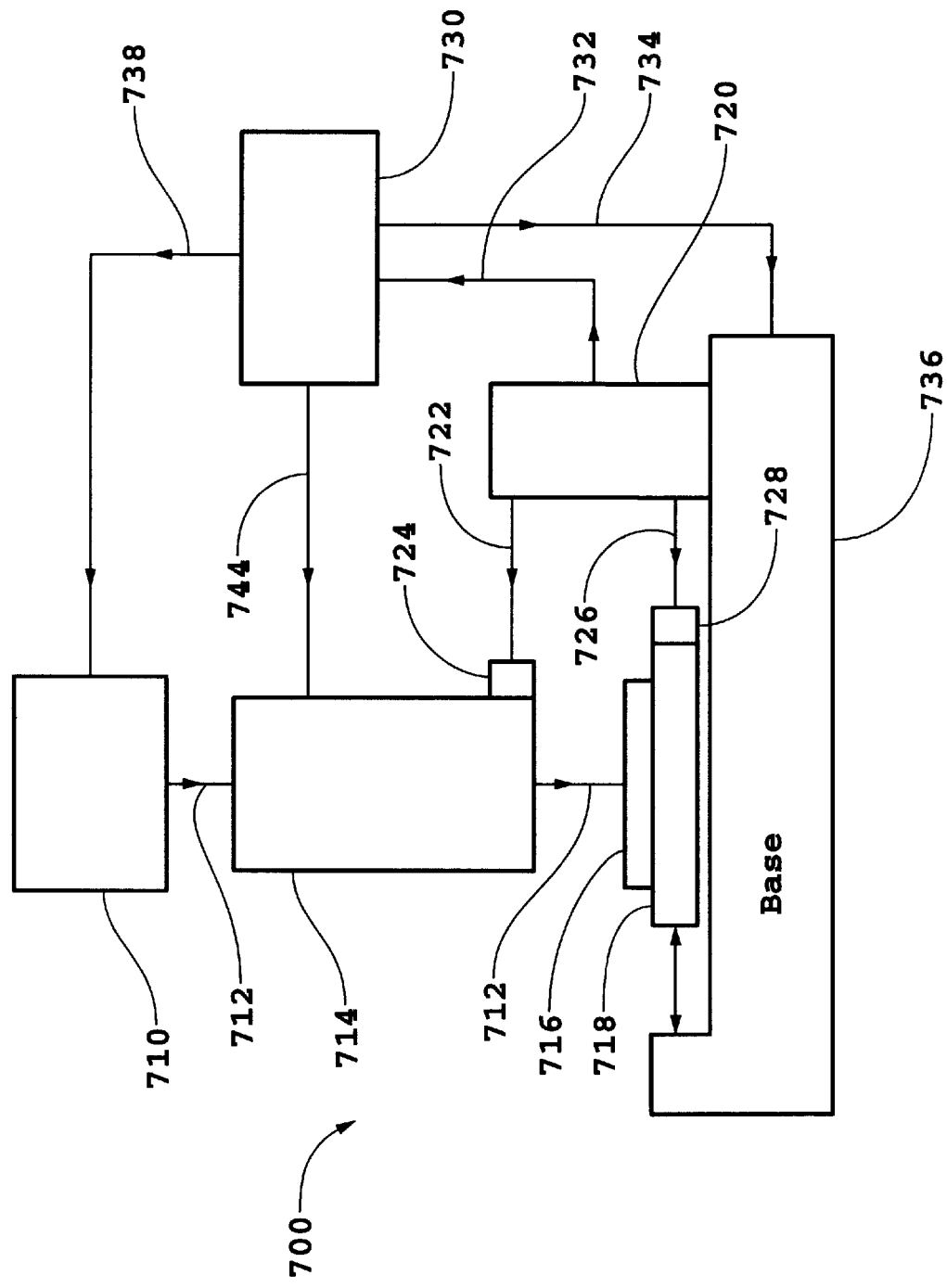
FIG. 7 is a schematic of a beam writing system employing the interferometry system.

As an example, a schematic of a beam writing system 700 is shown in FIG. 7. A source 710 generates a write beam 712, and a beam focusing assembly 714 directs the radiation beam to a substrate 716 supported by a movable stage 718. To determine the relative position of the stage, an interferometry system 720 directs a reference beam 722 to a mirror 724 mounted on beam focusing assembly 714 and a measurement beam 726 to a mirror 728 mounted on stage 718. Interferometry system 720 can be any of the interferometry systems described previously. Changes in the position measured by the interferometry system correspond to changes in the relative position of write beam 712 on substrate 716. Interferometry system 720 sends a measurement signal 732 to controller 730 that is indicative of the relative position of write beam 712 on substrate 716. Controller 730 sends an output signal 734 to a base 736 that supports and positions stage 718. In addition, controller 730 sends a signal 738 to source 710 to vary the intensity of, or block, write beam 712 so that the write beam contacts the substrate with an intensity sufficient to cause photophysical or photochemical change only at selected positions of the substrate. Furthermore, in some embodiments, controller 730 can cause beam focusing assembly 714 to scan the write beam over a region of the substrate, e.g., using signal 744. As a result, controller 730 directs the other components of the system to pattern the substrate. The patterning is typically based on an electronic design pattern stored in the controller. In some applications the write beam patterns a photoresist coated on the susbstrate and in other applications the write beam directly patterns, e.g., etches, the substrate.

An important application of such a system is the fabrication of masks and reticles used in the lithography methods described previously. For example, to fabricate a lithography mask an electron beam can be used to pattern a chromium-coated glass substrate. In such cases where the write beam is an electron beam, the beam writing system encloses the electron beam path in a vacuum. Also, in cases where the write beam is, e.g., an electron or ion beam, the beam focusing assembly includes electric field generators such as quadrapole lenses for focusing and directing the charged particles onto the substrate under vacuum. In other cases where the write beam is a radiation beam, e.g., x-ray, UV, or visible radiation, the beam focusing assembly includes corresponding optics for focusing and directing the radiation to the substrate.

Yet other changes may be made to the invention. For example, it may be desirable in certain applications to monitor the refractive index of the gas contained on both the reference and in the measurement legs of the interferometer. Examples include the well-known column reference style of interferometer, in which the reference leg comprises a target optic placed at one position within a mechanical system, and the measurement leg comprises a target optic placed at a different position within the same mechanical system. Another example application relates to the measurement of small angles, for which both the measurement and reference beams impinge upon the same target optic but at a small physical offset, thereby providing a sensitive measure of the angular orientation of the target optic. These applications and configurations are well known to those skilled in the art and the necessary modifications are intended to be within the scope of the invention.

Additional alternative means of achieving substantial insensitivity to Doppler shifting in a heterodyne interferometer is to track the Doppler shift and compensate by either (1) adjusting the frequency difference between the reference and measurement beams, (2) adjusting the clock frequency of one or both of the electronic A/D modules or (3) any similar means of continuously matching the apparent heterodyne beat frequency of the two wavelengths by active adjustment of the drive or detection electronics.

It is understood that while the invention has been described in conjunction with the detailed description thereof, the foregoing description is intended to illustrate and not limit the scope of the invention, which is defined by the scope of the appended claims.

What is claimed is:

1. Interferometric apparatus for measuring the effects of the refractive index of a gas in a measurement path, said interferometric apparatus comprising:

interferometer means comprising first and second measurement legs, said first and second measurement legs having optical paths structured and arranged such that at least one of them has a variable physical length and at least one of them is at least in part occupied by the gas and one of them is at least in part be occupied by a predetermined medium, the optical path length difference between said first and second measurement legs varying in accordance with the difference between the respective physical lengths of their optical paths and the properties of said gas and said predetermined medium;

means for generating at least two light beams having different wavelengths;

means for introducing first and second predetermined portions of each of said light beams into said first and second measurement legs, respectively, of said interferometer means so that beams at one of said wavelengths of said first and second predetermined portions of said light beams travel through at least one of said first and second measurement legs along predetermined optical paths a different number of passes than beams at the other of said wavelengths to compensate for the relative rates at which the physical path lengths of said first and second measurement legs are changing, said predetermined first and second portions of said light beams emerging from said interferometer means as exit beams containing information about the respective optical path lengths through said first and second measurement legs at said wavelengths;

means for combining said exit beams to produce mixed optical signals containing information corresponding to the phase differences between each of said exit beams from corresponding ones of said predetermined paths of said first and second measurement legs at said wavelengths;

means for detecting said mixed optical signals and generating electrical interference signals containing information corresponding to the effects of the indices of refraction of the gas and said predetermined medium at said different beam wavelengths and the relative physical path lengths between said first and second measurement legs and their rates of change; and electronic means for analyzing said interference electrical signals to determine the effects of said gas in said measurement legs.

2. The interferometric apparatus of claim 1 wherein said wavelengths of said light beams have an approximate harmonic relationship to each other, said approximate harmonic relationship being expressed as a sequence of ratios, each ratio being comprised of a ratio of low order non-zero integers.

3. The interferometric apparatus of claim 2 wherein said interferometer means comprises means for generating multiple passes along at least one of said measurement legs for said light beams where the number of passes for said light beams are harmonically related in a relationship which is substantially the same as said substantially harmonic relationship between said wavelengths.

4. The interferometric apparatus of claim 3 wherein said means for generating at least two light beams further includes means for generating orthogonally polarized components for each of said light beams.

5. The interferometric apparatus of claim 4 further including means for separating said light beams into pairs of orthogonally polarized components of common wavelength.

6. The interferometric apparatus of claim 5 further including means for spatially separating said orthogonally polarized pairs of components for subsequent downstream use in said interferometer means.

7. The interferometric apparatus of claim 2 wherein the relative precision of relationship of said wavelengths, expressed as said sequence of ratios, is an order of magnitude or more less than the dispersion of the refractive index of said gas, $(n_2-n_1)$ where $n_1$ and $n_2$ are, respectively, the indices of refraction of said gas at said different wavelengths, times the relative precision, $\epsilon$, desired for the measurement of the refractivity $(n_1-1)$ of the gas or of the change in the difference in optical path lengths of said measurement legs due to the gas.

8. The interferometric apparatus of claim 7 further including means for monitoring said relative precision of said approximate harmonic relationship expressed as said sequence of ratios.

9. The interferometric apparatus of claim 8 further including means responsive to said means for monitoring said relative precision of said approximate harmonic relationship for providing a feedback signal to control said means for generating said light beams so that said relative precision of said approximate harmonic relationship is of an order of magnitude or more less than the dispersion of the refractive index of said gas times the relative precision $\epsilon$ desired for the measurement of the refractivity $(n_1-1)$ of the gas or of the change in the difference in optical path lengths of said measurement legs due to the gas.

10. The interferometric apparatus of claim 1 wherein said electronic means is further adapted to determine the difference in physical lengths, L.

11. The apparatus of claim 10 wherein said means for generating at least two light beams having different wavelengths is further structured to generate a third light beam having a wavelength different from either wavelengths of said at least two light beams and wherein said electronic means is configured to receive the intrinsic optical property, the reciprocal dispersive power, $\Gamma$, of the gas, as:

$$\Gamma = \frac{[n_1(\lambda_1) - 1]}{[n_3(\lambda_3) - n_2(\lambda_2)]}, \text{ and}$$

$\lambda_1$, $\lambda_2$, and $\lambda_3$ are the wavelengths of said three light beams and $n_1$, $n_2$, and $n_3$ are indices of refraction and wherein the denominator may be replaced by $[n_3(\lambda_3)-n_1(\lambda_1)]$ or $[n_2(\lambda_2)-n_1(\lambda_1)]$.

12. The interferometric apparatus of claim 11 further including a microlithographic means operatively associated with said interferometer means such that said difference in physical lengths, L, may be used to determine the change in difference in relative distance between predetermined elements of said microlithographic means.

13. The interferometric apparatus of claim 1 wherein said interferometer means comprises at least one differential plane mirror interferometer.

14. The interferometric apparatus of claim 2 further including means for introducing a frequency difference between first and second portions of each of said light beams to generate a set of frequency-shifted light beams such that no two beams of said set of frequency-shifted light beams have the same frequency difference.

15. The interferometric apparatus of claim 14 wherein said interferometer means comprises means for generating multiple passes along said at least one of said measurement legs for said light beams where the number of passes for said light beams are harmonically related in a relationship which is substantially the same as said substantially harmonic relationship between said wavelengths.

16. The interferometric apparatus of claim 15 further including optical means for dividing each beam of said set of frequency-shifted light beams into one or more beams to provide an expanded set of at least three frequency-shifted light beams from said set of frequency-shifted light beams such that the number of frequency-shifted light beams for each wavelength in said expanded set of frequency-shifted light beams is inversely related in accordance with said approximate harmonic relationship and such that each beam of the set of expanded set of frequency-shifted light beams contains two frequency components.

17. The interferometric apparatus of claim 16 wherein said interferometer means introduces phase shifts between said different frequency components of each beam of said expanded set of at least three frequency-shifted light beams to produce said exit beams as a set of phase-shifted, frequency-shifted light beams and aligns and directs said beams of said expanded set of at least three frequency-shifted light beams so that the combined paths through at least one of the measurement legs traversed by each subset of phase-shifted, frequency-shifted light beams are substantially the same where a subset of said phase-shifted, frequency-shifted light beams comprises beams of the phase-shifted, frequency-shifted light beams having the same wavelength, the measurement paths traversed by any two beams of a subset of phase-shifted, frequency-shifted light beams being substantially non-overlapping.

18. The interferometric apparatus of claim 17 wherein the magnitude of said phase shifts introduced into each beam of said expanded set of at least three frequency-shifted light beams is the difference in phase shifts experienced by said beams in traveling along said first and second measurement legs and varies in accordance with the number of passes over respective ones of said first and second measurement legs, the physical lengths of respective ones of said first and second measurement legs, and the respective refractivity of the gas in said at least one of said measurement legs and respective refractivity of the gas and said predetermined medium, the refractivity of the gas in said at least one of said measurement legs for each subset of phase shifted, frequency-shifted light beams being different, one with respect to another, the refractivity of the gas being a function of wavelength.

19. The interferometric apparatus of claim 18 wherein said combining means mixes said two different frequency components of each beam of said set of phase-shifted, frequency-shifted light beams to produce said mixed optical signals as a set of mixed output beams comprised of at least three mixed output beams, each beam of the set of mixed output beams being derived from one beam of the set of phase-shifted, frequency-shifted light beams.

20. The interferometric apparatus of claim 19 wherein said means for detecting comprises a photodetector for generating said electrical interference signals as a set of at least three heterodyne signals from the intensities of said set of mixed output beams, said set of at least three heterodyne signals being characterized by oscillations at heterodyne frequencies related to said frequency differences between said different frequency components of the beams of said expanded set of frequency-shifted light beams, said set of at least three heterodyne signals being further characterized by a set of heterodyne phases, said set of at least three heterodyne signals being comprised of a set of subsets of heterodyne signals, a subset of heterodyne signals being the heterodyne signals generated from a subset of phase-shifted, frequency-shifted light beams.

21. The interferometric apparatus of claim 20 further including means for adding said heterodyne signals of each subset of heterodyne signals to produce a set of sum heterodyne signals, each sum heterodyne signal of said set of sum heterodyne signals having a sum heterodyne frequency equal to the heterodyne frequency of said subset of heterodyne signals added to produce said sum heterodyne signal and a sum heterodyne phase equal to the average of the heterodyne phases of said subset of heterodyne signals added to produce said sum heterodyne signal.

22. The interferometric apparatus of claim 21 wherein said electronic means further includes means for mixing two of said set of sum heterodyne signals to produce a superheterodyne signal, the superheterodyne signal being comprised of a lower frequency sideband having a sideband frequency equal to half the difference of the sum heterodyne frequencies of the sum heterodyne signals mixed to produce said superheterodyne signal and a sideband phase equal to half the difference of the sum heterodyne phases of the sum heterodyne signals mixed to produce the superheterodyne signal, the sideband phase of the lower frequency sideband being substantially null except for differences due to the dispersion of the refractivity of gas and to the dispersion of the predetermined medium in said measurement legs.

23. The interferometric apparatus of claim 22 further including means for monitoring the relative precision of said approximate harmonic relationship expressed as said sequence of ratios.

24. The interferometric apparatus of claim 23 further including means responsive to said means for monitoring said relative precision of said approximate harmonic relationship for providing a feedback signal to control said means for generating said light beams so that said relative precision of said approximate harmonic relationship is of an order of magnitude less than the dispersive power of the gas times the relative precision required for the measurement of the refractivity of the gas or of the change in the differences in the optical path lengths of said measurement legs due to the gas.

25. The interferometric apparatus of claim 19 wherein said means for combining is configured and arranged to produce said mixed optical signals as a set of mixed output beams comprised of at least two mixed output beams, each mixed output beam being generated from one subset of phase-shifted, frequency-shifted light beams.

26. The interferometric apparatus of claim 1 wherein said means for generating at least two light beams having different wavelengths comprises a coherent source of radiation.

27. The interferometric apparatus of claim 26 wherein said coherent source of radiation comprises a laser.

28. The interferometric apparatus of claim 1 further including means for directly receiving said electrical interference signals from said means for detecting and generating said electrical interference signals and converting said electrical interference signals to digital form to reduce phase errors in further downstream calculations.

29. The interferometric apparatus of claim 1 wherein said at least two light beams each have orthogonal polarization states.

30. The interferometric apparatus of claim 29 further including means for introducing a frequency difference(s) between said orthogonal polarization states of said light beams.

31. The interferometric apparatus of claim 30 wherein said means for combining said exit beams are adapted to mix said polarization states of said light beams.

32. The interferometric apparatus of claim 31 wherein said information corresponding to said phase differences in said mixed optical signals are phase shifts related to the differences in round-trip physical length L of said measurement legs occupied by said gas according to the formulae:

$$\varphi_1 = \sum_{i=1}^{i=p_1} \varphi_{1,i} = \sum_{i=1}^{i=p_1} L_i k_1 n_{1i} + \zeta_1,$$

$$\varphi_2 = \sum_{i=1}^{i=p_2} \varphi_{2,i} = \sum_{i=1}^{i=p_2} L_i k_2 n_{2i} + \zeta_2,$$

$$\varphi_3 = \sum_{i=p_2+1}^{i=p_1} \varphi_{3,i} = \sum_{i=p_2+1}^{i=p_1} L_i k_2 n_{2i} + \zeta_3,$$

for the case of $p_1=2p_2$ where the angular wavenumbers $k_j$ are given by $k_j=2\pi/\lambda_j$, $j=1$ and 2, and $n_{ji}$ are the refractive indices of gas in path i of said measurement leg corresponding to wavenumber $k_j$, and $$p_1\lambda_2 \cong p_2\lambda_1; \; p_1,p_2=1,2,3,\ldots, p_1 \neq p_2, \text{ and}$$

the phase offsets $\zeta_l$ comprise all contributions to the phase shifts $\phi_l$ that are not related to said first and second measurement legs.

33. The interferometric apparatus of claim 32 wherein said electrical interference signals comprise heterodyne signals of the form:

$$s_l = A_l \cos[\alpha_l(t)], \; l=1, 2, \text{ and } 3,$$

where the time-dependent arguments $\alpha_l(t)$ are given by $$\alpha_1(t)=2\pi f_1 t+\phi_1,$$

$$\alpha_2(t)=2\pi f_2 t+\phi_2,$$

$$\alpha_3(t)=2\pi f_2 t+\phi_3.$$

34. The interferometric apparatus of claim 33 wherein said electronic means is adapted to receive said heterodyne signals and determine said phase shifts, $\phi_1$, $\phi_2$, and $\phi_3$.

35. The interferometric apparatus of claim 32 further including means for resolving phase redundancy errors in said offsets, $\zeta_l$.

36. The interferometric apparatus of claim 1 further including means for resolving phase redundancy errors in said information.

37. Interferometric method for measuring the effects of the refractive index of a gas in a measurement path, said interferometric method comprising the steps of:

providing an interferometer means comprising a first and second measurement legs, said first and second measurement legs having optical paths structured and arranged such that at least one of them has a variable physical length and at least one of them is at least in part occupied by the gas and one of them is at least in part be occupied by a predetermined medium, the optical path length difference between said first and second measurement legs varying in accordance with the difference between the respective physical lengths of their optical paths and the properties of said gas and said predetermined medium;

generating at least two light beams having different wavelengths;

introducing first and second predetermined portions of each of said light beams into said first and second measurement legs, respectively, of said interferometer means so that beams at one wavelength of said first and second predetermined portions of said light beams travel through at least one of said first and second measurement legs along predetermined optical paths with a different number of passes than beams at the other of said wavelengths to compensate for the relative rates at which the physical path lengths of said first and second measurement legs are changing, said predetermined first and second portions of said light beams emerging from said interferometer means as exit beams containing information about the respective optical path lengths through said first and second measurement legs at said wavelengths;

combining said exit beams to produce mixed optical signals containing information corresponding to the phase differences between each of said exit beams from corresponding ones of said predetermined paths of said first and second measurement legs at said wavelengths;

detecting said mixed optical signals and generating electrical interference signals containing information corresponding to the effects of the indices of refraction of the gas and said predetermined medium at said different beam wavelengths and the relative physical path lengths between said first and second measurement legs and their rates of change; and electronically analyzing said interference electrical signals to determine the effects of said gas in said measurement legs.

38. The interferometric method of claim 37 wherein said wavelengths of said light beams have an approximate harmonic relationship to each other, said approximate harmonic relationship being expressed as a sequence of ratios, each ratio being comprised of a ratio of low order non-zero integers.

39. The interferometric method of claim 38 wherein including the step of generating within said interferometer means multiple passes along at least one of said measurement legs for said light beams where the number of passes for said light beams are harmonically related in a relationship which is substantially the same as said substantially harmonic relationship between said wavelengths.

40. The interferometric method of claim 39 wherein said step for generating at least two light beams further includes generating orthogonally polarized components for each of said light beams.

41. The interferometric method of claim 40 further including the step of separating said light beams into pairs of orthogonally polarized components of common wavelength.

42. The interferometric method of claim 41 further including the step of spatially separating said orthogonally polarized pairs of components for subsequent downstream use in said interferometer means.

43. The interferometric method of claim 38 wherein the relative precision of said approximate harmonic relationship expressed as said sequence of ratios is an order of magnitude or more less than the dispersion of the refractive index of said gas, $(n_2-n_1)$, where $n_1$ and $n_2$, are respectively, the indices of refraction of said gas at said different wavelengths, times the relative precision, $\epsilon$, desired for the measurement of the refractivity $(n_1-1)$ of the gas or of the change in the optical path length of at least one of said measurement legs due to the gas.

44. The interferometric method of claim 43 further including the step of monitoring said relative precision of said approximate harmonic relationship expressed as said sequence of ratios.

45. The interferometric method of claim 44 further including a step responsive to said step for monitoring said relative precision of said approximate harmonic relationship for providing a feedback signal to control said light beams so that said relative precision of said approximate harmonic relationship is of an order of magnitude or more less than the dispersion of the refractive index of said gas times the relative precision, $\epsilon$, desired for the measurement of the refractivity $(n_1-1)$ of the gas or of the change in the differences in optical path lengths of said measurement legs due to the gas.

46. The interferometric method of claim 37 wherein said electronically analyzing step further includes determining the differences in physical length, L, of said measurement legs occupied by said gas.

47. The interferometric method of claim 46 wherein said step of generating at least two light beams having different wavelengths further generates a third light beam having a wavelength different from either wavelengths of said at least two light beams and wherein said physical length, L, is calculated with a predetermined value for the reciprocal relative dispersion, $\Gamma$, of said gas where:

$$\Gamma = \frac{[n_1(\lambda_1)-1]}{[n_3(\lambda_3)-n_2(\lambda_2)]}, \text{ and}$$

$\lambda_1$, $\lambda_2$, and $\lambda_3$ are the wavelengths of the three light beams and $n_1$, $n_2$, and $n_3$ are indices of refraction and wherein the denominator may be replaced by $[n_3(\lambda_3)-n_1(\lambda_1)]$ or $[n_2(\lambda_2)-n_1(\lambda_1)]$.

48. The interferometric method of claim 47 further operatively associating a microlithographic means with said interferometer means such that said physical length, L, may be use to determine the relative distance between predetermined elements of said microlithographic means.

49. The interferometric method of claim 37 wherein said interferometer means comprises at least one differential plane mirror interferometer.

50. The interferometric method of claim 38 further including introducing a frequency difference between first and second portions of each of said light beams to generate a set of frequency-shifted light beams such that no two beams of said set of frequency-shifted light beams have the same frequency difference.

51. The interferometric method of claim 50 further including the step of generating within said interferometer means multiple passes along said at least one of said measurement legs for said light beams where the number of passes for said light beams are harmonically related in a relationship which is substantially the same as said substantially harmonic relationship between said wavelengths.

52. The interferometric method of claim 51 further including dividing each beam of said set of frequency-shifted light beams into one or more beams to provide an expanded set of at least three frequency-shifted light beams from said set of frequency-shifted light beams such that the number of frequency-shifted light beams for each wavelength in said expanded set of frequency-shifted light beams is inversely related in accordance with said approximate harmonic relationship and such that each beam of the set of expanded set of frequency-shifted light beams contains two frequency components.

53. The interferometric method of claim 52 introducing within said interferometer means phase shifts between said different frequency components of each beam of said expanded set of at least three frequency-shifted light beams to produce said exit beams as a set of phase-shifted, frequency-shifted light beams and aligns and directs said beams of said expanded set of at least three frequency-shifted light beams so that the combined paths through at least one of the measurement legs traversed by each subset of phase-shifted, frequency-shifted light beams are substantially the same where a subset of said phase-shifted, frequency-shifted light beams comprises beams of the phase-shifted, frequency-shifted light beams having the same wavelength, the measurement paths traversed by any two beams of a subset of phase-shifted, frequency-shifted light beams being substantially non-overlapping.

54. The interferometric method of claim 53 wherein the magnitude of said phase shifts introduced into each beam of said expanded set of at least three frequency-shifted light beams is the difference in phase shifts experienced by said beams in traveling along said first and second measurement legs and varies in accordance with the number of passes over respective ones of said first and second measurement legs, the physical lengths of respective ones of said first and second measurement legs, and the respective refractivity of the gas in said at least one of said measurement legs and respective refractivity of said predetermined medium of said measurement legs, the refractivity of the gas in said at least one of said measurement legs for each subset of phase shifted, frequency-shifted light beams being different, one with respect to another, the refractivity of the gas being a function of wavelength.

55. The interferometric method of claim 54 wherein said combining step mixes said two different frequency components of each beam of said set of phase-shifted, frequency-shifted light beams to produce said mixed optical signals as a set of mixed output beams comprised of at least three mixed output beams, each beam of the set of mixed output beams being derived from one beam of the set of phase-shifted, frequency-shifted light beams.

56. The interferometric method of claim 55 wherein said detecting step comprises photodetecting to generate said electrical interference signals as a set of at least three heterodyne signals from the intensities of said set of mixed output beams, said set of at least three heterodyne signals being characterized by oscillations at heterodyne frequencies related to said frequency differences between said different frequency components of the beams of said expanded set of frequency-shifted light beams, said set of at least three heterodyne signals being further characterized by a set of heterodyne phases, said set of at least three heterodyne signals being comprised of a set of subsets of heterodyne signals, a subset of heterodyne signals being the heterodyne signals generated from a subset of phase-shifted, frequency-shifted light beams.

57. The interferometric method of claim 56 further including adding said heterodyne signals of each subset of heterodyne signals to produce a set of sum heterodyne signals, each sum heterodyne signal of said set of sum heterodyne signals having a sum heterodyne frequency equal to the heterodyne frequency of said subset of heterodyne signals added to produce said sum heterodyne signal and a sum heterodyne phase equal to the average of the heterodyne phases of said subset of heterodyne signals added to produce said sum heterodyne signal.

58. The interferometric method of claim 57 wherein said electronically analyzing step further includes mixing two of said set of sum heterodyne signals to produce a superheterodyne signal, the superheterodyne signal being comprised of a lower frequency sideband having a sideband frequency equal to half the difference of the sum heterodyne frequencies of the sum heterodyne signals mixed to produce said superheterodyne signal and a sideband phase equal to half the difference of the sum heterodyne phases of the sum heterodyne signals mixed to produce the superheterodyne signal, the sideband phase of the lower frequency sideband being substantially null except for differences due to the dispersion of the refractivity of gas and to the dispersion of the predetermined medium in the measurement legs.

59. The interferometric method of claim 58 further including monitoring the relative precision of said approximate harmonic relationship expressed as said sequence of ratios.

60. The interferometric method of claim 59 further including the step, responsive to said step of monitoring said relative precision of said approximate harmonic relationship, of providing a feedback signal to control said light beams so that said relative precision of said approximate harmonic relationship is of an order of magnitude less than the dispersive power of the gas times the relative precision required for the measurement of the refractivity of the gas or of the change in the differences in optical path lengths of said measurement legs.

61. The interferometric method of claim 55 wherein said step of combining produces said mixed optical signals as a set of mixed output beams comprised of at least two mixed output beams, each mixed output beam being generated from one subset of phase-shifted, frequency-shifted light beams.

62. The interferometric method of claim 37 wherein said step of generating at least two light beams having different wavelengths comprises using a coherent source of radiation.

63. The interferometric method of claim 62 wherein said coherent source of radiation comprises a laser.

64. The interferometer method of claim 37 further including the step of directly receiving said electrical interference signals from said detecting step and converting said electrical interference signals to digital form to reduce phase errors in further downstream calculations.

65. The interferometric method of claim 37 further comprising the step of introducing orthogonal polarization states for each of said light beams.

66. The interferometric method of claim 65 further including the step of introducing a frequency difference(s) between said orthogonal polarization states of said light beams.

67. The interferometric method of claim 66 wherein said step of combining said exit beams mixes said polarization states of said light beams.

68. The interferometric method of claim 67 wherein said information corresponding to said phase differences in said mixed optical signals are phase shifts related to the round-trip physical length L of said measurement leg occupied by said gas according to the formulae:

$$\varphi_1 = \sum_{i=1}^{i=p_1} \varphi_{1,i} = \sum_{i=1}^{i=p_1} L_i k_1 n_{1i} + \zeta_1,$$

$$\varphi_2 = \sum_{i=1}^{i=p_2} \varphi_{2,i} = \sum_{i=1}^{i=p_2} L_i k_2 n_{2i} + \zeta_2,$$

$$\varphi_3 = \sum_{i=p_2+1}^{i=p_1} \varphi_{3,i} = \sum_{i=p_2+1}^{i=p_1} L_i k_2 n_{2i} + \zeta_3,$$

for the case of $p_1=2p_2$ where the angular wavenumbers $k_j$ are given by $k_j=2\pi/\lambda_j$, j=1 and 2, and $n_{ji}$ are the refractive indices of gas in path i of said at least one of said measurement legs corresponding to wavenumber $k_j$, and $p_1\lambda_2 \cong p_2\lambda_1$; $p_1,p_2$=1, 2, 3, . . . , $p_1 \neq p_2$, and the phase offsets $\zeta_l$ comprise all contributions to the phase shifts $\phi_l$ that are not related to the measurement legs.

69. The interferometric method of claim 68 wherein said electrical interference signals comprise heterodyne signals of the form:

$s_l = A_l \cos[\alpha_l(t)]$, l=1, 2, and 3, where the time-dependent arguments $\alpha_l(t)$ are given by $\alpha_1(t) = 2\pi f_1 t + \phi_1$, $\alpha_2(t) = 2\pi f_2 t + \phi_2$, $\alpha_3(t) = 2\pi f_2 t + \phi_3$.

70. The interferometric method of claim 69 wherein said electronically analyzing step receives said heterodyne signals and determines said phase shifts, $\phi_1$, $\phi_2$, and $\phi_3$.

71. The interferometric method of claim 68 further including the step of resolving phase redundancy errors in said offsets, $\zeta_l$.

72. The interferometric method of claim 37 further including the step of resolving phase redundancy errors in said information.

73. The interferometric apparatus of claim 1 further including a microlithographic means operatively associated with said interferometric apparatus for fabricating wafers, said microlithographic means comprising:

at least one stage for supporting a wafer;

an illumination system for imaging spatially patterned radiation onto the wafer; and a positioning system for adjusting the position of said at least one stage relative to the imaged radiation;

wherein said interferometric apparatus is adapted to measure the position of the wafer relative to the imaged radiation.

74. The interferometric apparatus of claim 1 further including a microlithographic means operatively associated with said interferometric apparatus for use in fabricating integrated circuits on a wafer, said microlithographic means comprising:

at least one stage for supporting a wafer;

an illumination system including a radiation source, a mask, a positioning system, a lens assembly, and predetermined portions of said interferometric apparatus, said microlithographic means being operative such that the source directs radiation through said mask to produce spatially patterned radiation, said positioning system adjusts the position of said mask relative to radiation from said source, said lens assembly images said spatially patterned radiation onto the wafer, and said interferometric apparatus measures the position of said mask relative to said radiation from said source.

75. The interferometric apparatus of claim 1 further including microlithographic apparatus operatively associated with said interferometric apparatus for fabricating integrated circuits comprising first and second components, said first and second components being moveable relative to one another and said interferometric apparatus, said first and second components being connected with said first and second measurement legs, respectively, moving in concert therewith, such that said interferometric apparatus measures the position of said first component relative to said second component.

76. The interferometric apparatus of claim 1 further including a beam writing system operatively associated with said interferometric apparatus for use in fabricating a lithography mask, said beam writing system comprising:

a source for providing a write beam to pattern a substrate;

at least one stage for supporting a substrate;

a beam directing assembly for delivering said write beam to the substrate; and a positioning system for positioning said at least one stage and said beam directing assembly relative to one another, said interferometric apparatus being adapted to measure the position of said at least one stage relative to said beam directing assembly.

77. The interferometric apparatus of claim 1 wherein said wavelengths have a non-harmonic relationship with respect to one another.

78. The interferometric apparatus of claim 1 wherein said electronic means further includes phase analyzing means for receiving said electrical interference signals and generating initial electrical phase signals containing information corresponding to the effects of the indices of refraction of the gas and said predetermined medium at said different beam wavelengths and the difference in physical path lengths of said measurement legs occupied by said gas and its rate of change.

79. The interferometric apparatus of claim 78 wherein said electronic means further includes multiplying means for multiplying said initial phase signals by factors corresponding to the ratios of said wavelengths and the number of round trip passes experienced by said beams in traveling through said interferometer means to generate modified phase signals.

80. The interferometric apparatus of claim 79 wherein said electronic means further includes means for receiving said modified phase signals and selectively adding and subtracting them to generate sum and difference phase signals containing information corresponding to the effects of the index of refraction of the gas at said different beam wavelengths and the difference in the physical path lengths of said measurement legs occupied by said gas and its rate of change.

81. The interferometric apparatus of claim 80 wherein said electronic means further includes means for receiving said sum and difference phase signals and at least one of said initial phase signals to determine the differences in physical length, L, of said measurement leg(s) occupied by said gas.

82. The interferometric apparatus of claim 81 further including means for resolving redundancies among said initial phase and said sum and difference phase signals.

83. The interferometric apparatus of claim 79 wherein said wavelengths are non-harmonically related.

84. The interferometric apparatus of claim 79 wherein said wavelengths of said light beams have an approximate harmonic relationship to each other, said approximate harmonic relationship being expressed as a sequence of ratios, each ratio being comprised of a ratio of low order non-zero integers.

85. The interferometric apparatus of claim 29 further including means for introducing frequency differences between said orthogonal polarization states of said light beams such that at least two of said light beams have different frequencies between their respective polarization states and a single photodetector for generating phase signals from at least two of said exit beams.

86. The interferometric apparatus of claim 1 wherein the relative precision of relationship of said wavelengths, expressed as said sequence of ratios, is the order of or greater than approximately one-tenth of the dispersion of the refractive index of said gas, $(n_2-n_1)$, where $n_1$ and $n_2$ are, respectively, the indices of refraction of said gas at said different wavelengths, times the relative precision, $\epsilon$, desired for the measurement of the refractivity $(n_1-1)$ of the gas or of the change in the differences of the optical path lengths of said measurement legs due to the gas.

87. The interferometric method of claim 37 further including the steps of:
supporting a wafer on at least one moveable stage;
imaging spatially patterned radiation onto the wafer;
adjusting the position of said at least one stage relative to the imaged radiation; and
measuring the position of the wafer relative to the imaged radiation.

88. The interferometric method of claim 37 further including the steps of:
supporting a wafer on at least moveable stage;
directing a source of radiation through a mask and lens assembly to produce spatially patterned radiation,
adjusting the position of said mask relative to radiation from said source, said lens assembly imaging said spatially patterned radiation onto the wafer, and measuring the position of said mask relative to said radiation from said source.

89. The interferometric method of claim 37 further including the steps of providing a microlithographic apparatus for fabricating integrated circuits comprising first and second components, said first and second components being moveable relative to one another, said first and second components being connected with said first and second measurement legs, respectively, moving in concert therewith, such that the position of said first component relative to said second component is measured.

90. The interferometric method of claim 37 further including the steps of:
providing a pattern of radiation with a write beam source;
supporting a substrate on at least one stage;
directing said write beam such that said pattern of radiation impinges onto the substrate; and
positioning said at least one stage and said write beam of radiation relative to one another, and
measuring the position of said at least one stage relative to said write beam.

91. The interferometric method of claim 37 wherein said wavelengths have a non-harmonic relationship with respect to one another.

92. The interferometric method of claim 37 wherein said step of electronically analyzing further includes the step of receiving said electrical interference signals and extracting the phase therefrom to generate initial electrical phase signals containing information corresponding to the effects of the indices of refraction of the gas and said predetermined medium at said different beam wavelengths and the difference in physical path lengths of said measurement legs occupied by said gas and their relative rates of change.

93. The interferometric method of claim 92 wherein said step of electronically analyzing further includes the step of multiplying said initial phase signals by factors corresponding to the ratios of said wavelengths and the number of round trip passes experienced by said beams in traveling through said interferometer means to generate modified phase signals.

94. The interferometric method of claim 93 wherein said step of electronically analyzing further includes the step of receiving said modified phase signals and selectively adding and subtracting them to generate sum and difference phase signals containing information corresponding to the effects of the indices of refraction of the gas and said predetermined medium at said different beam wavelengths and the difference in physical path lengths of said measurement legs occupied by said gas and their relative rates of change.

95. The interferometric method of claim 94 wherein said step of electronically analyzing further includes the step of receiving said sum and difference phase signals and at least one of said initial phase signals to determine the difference in physical lengths, L, of said measurement legs occupied by said gas.

96. The interferometric method of claim 94 further including the step of resolving redundancies among said initial phase and said sum and difference phase signals.

97. The interferometric method of claim 93 wherein said wavelengths are non-harmonically related.

98. The interferometric method of claim 93 wherein said wavelengths of said light beams have an approximate harmonic relationship to each other, said approximate harmonic relationship being expressed as a sequence of ratios, each ratio being comprised of a ratio of low order non-zero integers.

99. The interferometric method of claim 66 further including the step of introducing frequency differences between said orthogonal polarization states of said light beams such that at least two of said light beams have different frequencies between their respective polarization states and using a single photodetector for generating phase signals from at least two of said exit beams.

100. The interferometric for of claim 37 wherein the relative precision of relationship of said wavelengths, expressed as said sequence of ratios, is the order of or greater than approximately one-tenth of the dispersion of the refractive index of said gas, $(n_2-n_1)$, where $n_1$ and $n_2$ are, respectively, the indices of refraction of said gas at said different wavelengths, times the relative precision, $\epsilon$, desired for the measurement of the refractivity $(n_1-1)$ of the gas or of the change in the differences in optical path lengths of said measurement legs due to the gas.

* * * * *